(12) United States Patent
Adcock et al.

(10) Patent No.: US 8,937,069 B2
(45) Date of Patent: Jan. 20, 2015

(54) SUBSTITUTED PYRROLO[2,3-B]PYRAZINE COMPOUNDS AND THEIR USE

(71) Applicant: Novartis AG, Basel (CH)

(72) Inventors: Claire Adcock, Horsham (GB); Catherine Leblanc, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/739,302

(22) Filed: Jan. 11, 2013

(65) Prior Publication Data

US 2013/0184282 A1    Jul. 18, 2013

Related U.S. Application Data

(60) Provisional application No. 61/586,546, filed on Jan. 13, 2012.

(51) Int. Cl.
| A61K 31/4985 | (2006.01) |
| C07D 487/04 | (2006.01) |
| A61K 45/06 | (2006.01) |

(52) U.S. Cl.
CPC .......... *C07D 487/04* (2013.01); *A61K 31/4985* (2013.01); *A61K 45/06* (2013.01)
USPC .......................................... 514/249; 544/350

(58) Field of Classification Search
CPC ........................... A61K 31/4985; C07D 487/04
USPC ........................................... 514/249; 544/350
See application file for complete search history.

(56) References Cited

U.S. PATENT DOCUMENTS

| 3,960,876 A | 6/1976 | Curran |
| 2008/0027039 A1 | 1/2008 | Arakawa et al. |
| 2008/0064871 A1 | 3/2008 | Kazuyuki et al. |
| 2008/0280041 A1 | 11/2008 | Nishino et al. |
| 2008/0305169 A1 | 12/2008 | Miki et al. |
| 2013/0184282 A1 | 7/2013 | Adcock |

FOREIGN PATENT DOCUMENTS

| EP | 558062 | 9/1993 |
| EP | 753528 | 1/1997 |
| EP | 0976732 | 2/2000 |
| EP | 1400518 | 3/2004 |
| EP | 1475368 | 11/2004 |
| EP | 1820515 | 8/2007 |
| WO | WO 92/20642 | 11/1992 |
| WO | WO 95/09872 | 4/1995 |
| WO | WO 96/35713 | 11/1996 |
| WO | WO 98/18796 | 5/1998 |
| WO | WO 00/33838 | 6/2000 |
| WO | WO 00/78724 | 12/2000 |
| WO | WO 01/17959 | 3/2001 |
| WO | WO 01/19788 | 3/2001 |
| WO | WO 01/34602 | 5/2001 |
| WO | WO 01/49675 | 7/2001 |
| WO | WO 01/58441 | 8/2001 |
| WO | WO 03/039544 | 5/2003 |
| WO | WO 2004/083207 | 9/2004 |
| WO | WO 2004/099159 | 11/2004 |
| WO | WO 2005/020926 | 3/2005 |
| WO | WO 2005/051386 | 6/2005 |
| WO | WO 2005/063766 | 7/2005 |
| WO | WO 2006/122156 | 11/2006 |
| WO | WO 2007/017096 | 2/2007 |
| WO | WO 2007/024944 | 3/2007 |
| WO | WO 2007/088019 | 8/2007 |
| WO | WO 2008/154221 | 12/2008 |
| WO | WO 2010/008864 | 1/2010 |
| WO | WO 2010/009208 | 1/2010 |

(Continued)

OTHER PUBLICATIONS

Paetzel et al., Journal of Heterocyclic Chemistry 29(5):1067-1068, 1992.
Cosmao et. al., Canadian Journal of Chemistry 60(22):2785-2791, 1982.
Armand et al. Canadian Journal of Chemistry 56(13):1804-1816, 1978.
Armand et al., Compte Rendus des Seanees de l' Academic des Sciences, Serir C: Sciences Chimiques 281(13):547-549, 1975.
Vinot et al., Bulletin de la Societe Chimique de France (1973), (II, Pt. 2), 3100-3102.

(Continued)

*Primary Examiner* — Douglas M Willis
(74) *Attorney, Agent, or Firm* — Rona Nardone

(57) ABSTRACT

The present invention provides compounds of formula (Ia) and (Ib) which activate the IP receptor, processes for preparing them, pharmaceutical compositions comprising said compounds and uses thereof. Activating the IP receptor signaling pathway is useful to treat many forms of PAH, pulmonary fibrosis and exert beneficial effects in fibrotic conditions of various organs in animal models and in patients.

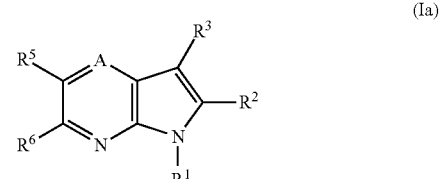

(Ia)

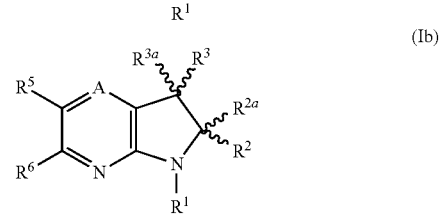

(Ib)

9 Claims, No Drawings

(56) References Cited

FOREIGN PATENT DOCUMENTS

| | | |
|---|---|---|
| WO | WO 2010/020366 | 2/2010 |
| WO | WO 2011/111880 | 9/2011 |
| WO | WO 2012/007539 | 1/2012 |
| WO | WO 2013/105057 | 7/2013 |
| WO | WO 2013/105058 | 7/2013 |
| WO | WO 2013/105061 | 7/2013 |
| WO | WO 2013/105063 | 7/2013 |
| WO | WO 2013/105065 | 7/2013 |
| WO | WO 2013/105066 | 7/2013 |

OTHER PUBLICATIONS

E. Kelly et al., "NaF and Guanine Nucleotides Modulate Adenylate Cyclase Activity in NG108-15 Cells by Interacting with Both $G_s$ and $G_i$" Br J Pharmacol. 100(2):223-230 Jun. 1990.

Kuwano et al., "2-(4-[(5,6-Diphenylpyrazin-2-yl)(isopropyl)amino]butoxy}-N-(methylsulfonyl)acetamide (MS-304), an Orally Available and Long-Acting Prostacyclin Receptro Agonist Prodrug" *Journal of Pharmacology and Experimental Therapeutics* 322(3):1181-1188, 2007.

Driscoll et al., "Medical Therapy for Pulmonary Arterial Hypertension" *Expert Opinion on Pharmacotherapy*, 9(1):65-81.

SUBSTITUTED PYRROLO[2,3-B]PYRAZINE COMPOUNDS AND THEIR USE

CROSS-REFERENCE TO RELATED APPLICATIONS

This application is the U.S. National Stage patent application, which claims the benefit of priority to U.S. Provisional Application Ser. No. 61/586,546, filed on Jan. 13, 2012, which is incorporated herein by reference in its entirety.

BACKGROUND OF THE INVENTION

Prostacyclin (or PGI2) is a member of the family of lipid molecules known as eicosanoids. It is a potent vasodilator, antiproliferative, anti-thrombotic agent that mediates its effects as an agonist of the IP receptor. The IP receptor is a G-protein coupled receptor that, upon activation by prostacyclin, stimulates the formation of cyclic adenosine monophosphate (cAMP). Prostacyclin counteracts the vasoconstrictor and pro-thrombotic activity of endothelin.

Pulmonary arterial hypertension (PAH) is a life-threatening disease characterized by a progressive pulmonary vasculopathy leading to right ventricular hypertrophy. Exogenous administration of an agonist of the IP receptor has become an important strategy in the treatment of PAH. (See, e.g., Tuder et al., Am. J. Respir. Crit. Care. Med., 1999, 159: 1925-1932; Humbert et al, J. Am. Coll. Cardiol., 2004, 43:13 S-24S; Rosenzweig, Expert Opin. Emerging Drugs, 2006, 11:609-619; McLaughlin et al, Circulation, 2006, 114:1417-1431; Rosenkranz, Clin. Res. Cardiol., 2007, 96:527-541; Driscoll et al, Expert Opin. Pharmacother., 2008, 9:65-81.).

The prostacyclin analogue epoprostenol (flolan) is at least as effective as transplantation in terms of survival. Despite this, it is not used as frontline therapy due to significant tolerability, convenience and cost issues. Instead, patients with PAH are often treated first with either endothelin receptor antagonists (e.g. bosentan) and/or PDE5 inhibitors (e.g. sildenafil), which are better tolerated but can have limited efficacy. Prostacyclin analogues are used mainly as add-on treatment as severity of the disease progresses and tolerability and convenience become less of an issue.

Two key issues prevent current prostacyclin analogues being used as frontline therapy in PAH. Firstly, they are very unstable with an extremely short half-life, meaning they must be constantly infused via an in-dwelling intra venous (i.v.) catheter that is both inconvenient for the patient and also associated with a significant risk of infection and sepsis. Secondly, they are associated with significant side effects including nausea, jaw pain, headache and other side effects associated with systemic hypotension.

One solution to these issues is iloprost, which is available as a nebulised formulation that has reduced tolerability issues, but the short half life results in a 6-9 times daily dosing regime. More recently, researchers made efforts to generate stable, orally available IP receptor agonists. These ligands would improve patient convenience and compliance, but high levels of systemic drug is required to achieve pharmacodynamic effects in the lung; thus, possibly generating similar side effects to those observed with i.v. flolan.

The present invention describes stable, highly selective IP receptor agonists that are suitable for oral and inhaled delivery. The present invention offers a significant improvement over existing prostacyclin analogues and enables their use in less-severe patients. In addition, long term activation of the IP receptor has been shown to reverse remodeling associated with PAH; therefore, earlier intervention with the present invention may have significant effects on disease progression and potentially may show reversal.

In addition, pharmaceutical research has considerable interest in developing IP receptor agonists for the treatment of pulmonary fibrosis. IP deficient mice have been shown to be more susceptible to bleomycin-induced lung fibrosis than wild-type animals (Lovgren A K et al. (2006) *Am J Physiol Lung Cell Mol. Physiol.* 291:L144-56), and the IP receptor agonist iloprost increases survival in bleomycin-treated mice (Zhu et al (2010) Respir Res. 11(1):34).

Furthermore, IP receptor signaling has been shown to exert beneficial effects in fibrotic conditions of various organs in animal models and in patients. Benefits of IP receptor agonist were shown for fibrosis of the heart, lung, skin, pancreas and liver, and in systemic sclerosis. (Gayraud M (2007) *Joint Bone Spine.* 74(1):e1-8; Hirata Y et al (2009) *Biomed Pharmacother.* 63(10):781-6; Kaneshige T et al (2007) *J Vet Med. Sci.* 69(12):1271-6; Sahsivar M O et al (2009) *Shock* 32(5): 498-502; Sato N et al (2010) *Diabetes* 59(4):1092-100; Shouval D S et al (2008) *Clin Exp Rheumatol.* 26(3 Suppl 49): 5105-7; Spargias K et al (2009) *Circulation.* 120(18):1793-9; Stratton R et al (2001) *J Clin Invest.* 108(2):241-50; Takenaka M et al (2009) Prostaglandins Leukot Essent Fatty Acids. 80(5-6):263-7; Watanabe M et al (2009) *Am J. Nephrol.* 30(1):1-11; Yano T et al (2005) *Am J Pathol.* 166(5):1333-42; Zardi E M et al (2007) *Expert Opin Biol Ther.* 7(6):785-90; Zardi E M et al (2006) *In Vivo* 20(3):377-80; Rehberger P et al (2009) *Acta Derm Venereol.* 89(3):245-9). Fibrotic conditions can occur in most organs secondary to chronic inflammation indications throughout the body and are likely to share common causes. Therefore, antifibrotic agents such as IP receptor agonists of the present invention are of potential benefit in all indications that are associated with fibrotic tissue remodeling.

There is considerable interest in developing agonists of the IP receptor for use in the treatment of other diseases, such as atherothrombosis, preeclampsia. It is highly desirable to develop stable, inhaled agonists of the IP receptor, which may lead to improved management of PAH.

BRIEF SUMMARY OF THE INVENTION

The invention pertains to the compounds, methods for using them, and uses thereof as described herein. Examples of compounds of the invention include the compounds according to any of Formula I, or a pharmaceutically acceptable salt thereof, and the compounds of the examples.

DETAILED DESCRIPTION OF THE INVENTION

In a first aspect, there is provided a compound represented by formula

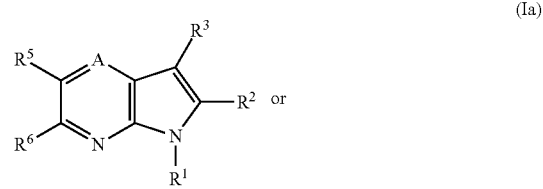

(Ia)

3
-continued

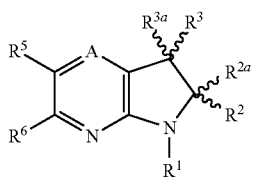

(Ib)

or a pharmaceutically acceptable salt thereof, wherein
A is N or CR';
R' is H, $C_1$-$C_8$ alkyl optionally substituted by one or more halogen atoms;
$R^1$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —($C_2$-$C_4$ alkyl)-$NR^{19}R^{21}$ and $C_3$-$C_7$ cycloalkyl; or
$R^1$ is —X—Y; or
$R^1$ is —W—$R^7$—X—Y; or
$R^1$ is —S(O)$_2$—X—Y; or
$R^1$ is —S(O)$_2$—W—$R^7$—X—Y;
$R^2$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; $C_1$-$C_4$ alkoxy; —($C_0$-$C_4$ alkyl)-$NR^{19}R^{21}$ and $C_3$-$C_7$ cycloalkyl; or
$R^2$ is —X—Y; or
$R^2$ is —W—$R^7$—X—Y; or
$R^2$ is —S(O)$_2$—X—Y; or
$R^2$ is —S(O)$_2$—W—$R^7$—X—Y;
$R^{2a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or
$R^2$ and $R^{2a}$ taken together are oxo;
wherein one of $R^1$ and $R^2$ is —X—Y, —W—$R^7$—X—Y, —S(O)$_2$—X—Y; or —S(O)$_2$—W—$R^7$—X—Y;
$R^3$ is independently selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —OH; OR';
—($C_0$-$C_4$alkyl)-$NR^{19}R^{21}$; CN; halogen; —($C_0$-$C_4$alkyl)-$C_6$-$C_{14}$aryl; —($C_0$-$C_4$alkyl)-4 to 14 membered heteroaryl; —C(=O)H; —C(=O)OH; —C(=O)$NR^{19}R^{21}$ and $C_3$-$C_7$ cycloalkyl, wherein the aryl and heteroaryl are optionally substituted by one or more substituents independently selected from OH, $C_1$-$C_4$ alkyl, $C_1$-$C_4$ alkoxy, halogens and $C_1$-$C_4$ haloalkyl;
$R^{3a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or
$R^3$ and $R^{3a}$ taken together are oxo;
$R^5$ and $R^6$ are independently selected from —($C_0$-$C_4$ alkyl)-$C_6$-$C_{14}$ aryl and —($C_0$-$C_4$ alkyl)-4 to 14 membered heteroaryl, wherein the aryl and heteroaryl are each optionally substituted by one or more Z substituents;
W is $C_1$-$C_8$ alkylene optionally substituted by hydroxy, halogens or $C_1$-$C_4$ alkyl;
X is $C_1$-$C_8$ alkylene optionally substituted by hydroxy, halogens or $C_1$-$C_4$ alkyl;
Y is carboxy, $C_1$-$C_4$-alkoxycarbonyl, tetrazolyl, —C(=O)$NR^{19}R^{21}$ or —CONH—S(O)$_q$—$R^x$, wherein
$R^x$ is phenyl, benzyl or —$NR^{19}R^{21}$;
q is 0, 1 or 2;
$R^7$ is a divalent moiety represented by —O—, —S—, —NHC(O)—, —CH$_2$=CH$_2$—, —$C_6$-$C_{14}$ aryl-D-; -3 to 14 membered heterocyclyl-D-, wherein the heterocyclyl contains at least one heteroatom selected from N, O and S, wherein D is O, S, NH or not present;

4

Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$ alkoxy, $NR^{18}(SO_2)R^{21}$, $(SO_2)NR^{19}R^{21}$, $(SO_2)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclyl, wherein the heterocyclyl contains at least one heteroatom selected from N, O and S;
$R^{18}$ is independently H or $C_1$-$C_6$ alkyl;
$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; —($C_1$-$C_4$ alkyl)-carboxy; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclyl, the heterocyclyl including one or more heteroatoms selected from N, O and S, optionally substituted by one or more groups selected from halogen, oxo, $C_1$-$C_6$ alkyl and C(O)$C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl;
wherein the alkyl groups are optionally substituted by one or more halogen atoms, OH, $C_1$-$C_4$ alkoxy, C(O)$NH_2$, C(O)NH$C_1$-$C_6$ alkyl or C(O)N($C_1$-$C_6$ alkyl)$_2$; or
$R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; S(O)$_2$-aryl; S(O)$_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and C(O)O$C_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Various embodiments of the invention are described herein. It will be recognized that features specified in each embodiment may be combined with other specified features to provide further embodiments.

DEFINITIONS

Terms used in the specification have the following meanings:

"Optionally substituted" means the group referred to can be substituted at one or more positions by any one or any combination of the radicals listed thereafter.

"Optionally substituted by one or more Z groups" denotes that the relevant group may include one or more substituents, each independently selected from the groups included within the definition of Z. Thus, where there are two or more Z group substituents, these may be the same or different.

"Halo" or "halogen", as used herein, may be fluorine, chlorine, bromine or iodine.

"$C_1$-$C_8$-Alkyl", as used herein, denotes straight chain or branched alkyl having 1-8 carbon atoms. If a different number of carbon atoms is specified, such as $C_6$ or $C_3$, then the definition is to be amended accordingly, such as "$C_1$-$C_4$-

Alkyl" will represent methyl, ethyl, propyl, isopropyl, butyl, isobutyl, sec-butyl and tert-butyl.

"$C_1$-$C_8$-Alkoxy", as used herein, denotes straight chain or branched alkoxy having 1-8 carbon atoms. If a different number of carbon atoms is specified, such as $C_6$ or $C_3$, then the definition is to be amended accordingly, such as "$C_1$-$C_4$-Alkoxy" will represent methoxy, ethoxy, propoxy, isopropoxy, butoxy, isobutoxy, sec-butoxy and tert-butoxy.

"$C_1$-$C_4$-Haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.

The term "alkylene" is a straight or branched alkylene (divalent alkyl chain) having 1 to 8 carbon atoms, for example, methylene, ethylene, 1-methylethylene, 2-methylethylene, trimethylene, tetramethylene, pentamethylene, hexamethylene, heptamethylene, and octamethylene.

"$C_3$-$C_{15}$ Cycloalkyl", as used herein, denotes a carbocyclic group having 3- to 15-ring carbon atoms that is saturated or partially saturated, such as a $C_3$-$C_8$-cycloalkyl. Examples of $C_3$-$C_{15}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl and bicyclodecyl. If a different number of carbon atoms is specified, such as $C_6$, then the definition is to be amended accordingly.

"aryl" or "$C_6$-$C_{15}$-Aromatic carbocyclic group", as used herein, denotes an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriyl or anthrylene. If a different number of carbon atoms is specified, such as $C_m$, then the definition is to be amended accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings containing at least one ring heteroatom selected from the group consisting of nitrogen, oxygen and sulphur, which may be saturated, partially saturated or unsaturated (aromatic). The heterocyclyl includes single ring groups, fused ring groups and bridged groups. Examples of such heterocyclyl include, but are not limited to, furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahyrofuran, tetrahydrothiophene, tetrahydrothiopyran, tetrahydropyran, 1,4-dioxane, 1,4-oxathiane, indazole, quinoline, indazole, indole, 8-aza-bicyclo[3.2.1]octane, 2,3-dihydrobenzofuran or thiazole.

"Heteroaryl" is a subset of heterocyclyl, wherein the completely unsaturated (aromatic). Examples of such groups are pyridine and pyrazine.

The term "hydroxy" or "hydroxyl" includes groups with an —OH.

The term "heteroatom" includes atoms of any element other than carbon or hydrogen. Preferred heteroatoms are nitrogen, oxygen, sulfur and phosphorus. In one embodiment, "heteroatom" includes nitrogen, sulfur and oxygen.

The term "carboxy" refers to carboxylic acid.

The term "alkoxycarboxy" refers to an ester.

The term "carbamoyl" is —C(O)NH$_2$. The terms "monoalkylcarbamoyl" and "dialkylcarbamoyl" are carbamoyl, wherein the hydrogen or hydrogens on the nitrogen are substituted with $C_1$-$C_8$ alkyl as described above.

In an embodiment (i) of the first aspect,
wherein one of $R^1$ and $R^2$ is —X—Y, —W—$R^7$—X—Y, —S(O)$_2$—X—Y; or —S(O)$_2$—W—$R^7$—X—Y;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is carboxy, $C_1$-$C_4$-alkoxycarbonyl, tetrazolyl, —C(=O)NR$^{19}$R$^{21}$ or —CONH—S(O)$_q$—R$^x$,
wherein R$^x$ is phenyl, benzyl or —NR$^{19}$R$^{21}$;
q is 2;
R$^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and
R$^{19}$ and R$^{21}$ are each independently H; $C_1$-$C_8$ alkyl.

In an embodiment (ii) of the first aspect,
wherein one of $R^1$ and $R^2$ is —X—Y or —W—$R^7$—X—Y;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is carboxy, $C_1$-$C_4$-alkoxycarbonyl, tetrazolyl, —C(=O)NR$^{19}$R$^{21}$ or —CONH—S(O)$_q$—R$^x$, wherein R$^x$ is phenyl, benzyl or —NR$^{19}$R$^{21}$;
q is 2;
R$^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and
R$^{19}$ and R$^{21}$ are each independently H; $C_1$-$C_8$ alkyl.

In an embodiment (iii) of the first aspect,
one of $R^1$ and $R^2$ is —X—Y or —W—$R^7$—X—Y;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is —C(O)OH; and
R$^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

In an embodiment (iv) of the first aspect,
one of $R^1$ and $R^2$ is —(CH$_2$)$_m$—C(O)OR", or —(CH$_2$)$_m$—R$^7$—(CH$_2$)$_n$—C(O)OR";
m is 1, 2, 3, 4, 5, 6, 7 or 8;
n is 0, 1, 2 or 3;
R" is H or $C_1$-$C_4$ alkyl optionally substituted by one or more halogen atoms; and
R$^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

In an embodiment (v) of the first aspect,
one of $R^1$ and $R^2$ is —(CH$_2$)$_m$—C(O)OR";
m is 3, 4, 5, 6, 7 or 8; and
R" is H or $C_1$-$C_4$ alkyl optionally substituted by one or more halogen atoms.

In an embodiment (vi) of the first aspect,
one of $R^1$ and $R^2$ is —$(CH_2)_m$—C(O)OR";
R" is H; and
m is 4, 5 or 6.

In an embodiment (vii) of the first aspect,
one of $R^1$ and $R^2$ is

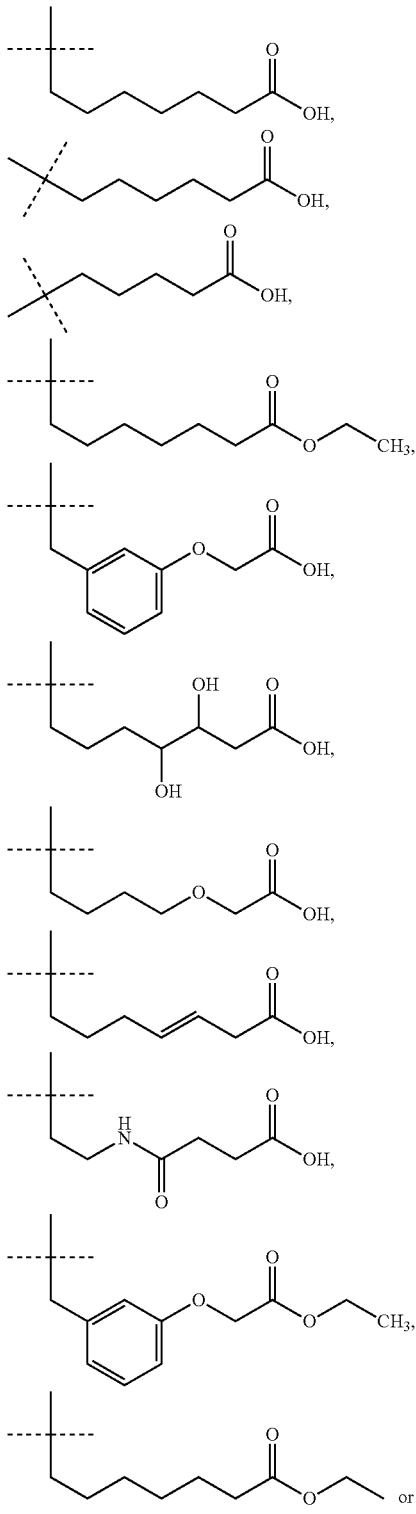

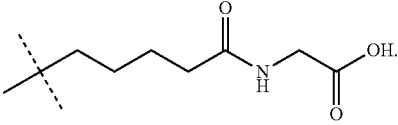

In an embodiment (viii) of the first aspect,
$R^2$ is H, $C_1$-$C_8$ alkyl optionally substituted by one or more halogen atoms, $C_1$-$C_4$ alkoxy, $C_3$-$C_7$cycloalkyl, OH, or OR';
$R^{2a}$ is H; or
$R^2$ and $R^{2a}$ together are oxo;
R' is H, $C_1$-$C_4$ alkyl.

In an embodiment (ix) of the first aspect,
$R^2$ is H, $C_1$-$C_8$ alkyl optionally substituted by one or more halogen atoms, $C_1$-$C_4$ alkoxy, $C_3$-$C_7$cycloalkyl, OH, or OR'.

In an embodiment (x) of the first aspect,
$R^2$ is H, $C_1$-$C_4$ alkyl optionally substituted by one or more halogen atoms, or $C_3$-$C_7$cycloalkyl.

In an embodiment (xi) of the first aspect,
$R^2$ is H.

In an embodiment (xii) of the first aspect,
$R^3$ and $R^{3a}$ are independently selected from H; $C_1$-$C_4$ alkyl optionally substituted by one or more halogen atoms or OH; —C(=O)H and OH; or $R^3$ and $R^{3a}$ taken together are oxo.

In an embodiment (xiii) of the first aspect,
$R^5$ and $R^6$ are independently selected from $C_6$-$C_{14}$ aryl and 5 to 6 membered heteroaryl, wherein the heteroaryl contains at least one heteroatom selected from N, O and S, wherein the aryl and heteroaryl are each optionally substituted by one or more Z substituents.

In an embodiment (xiv) of the first aspect,
$R^5$ and $R^6$ are independently selected from phenyl; 2-pyridyl, 3-pyridyl, or 4-pyridyl,
wherein the phenyl, 2-pyridyl, 3-pyridyl, and 4-pyridyl are each optionally substituted by one or more Z substituents.

In an embodiment (xv) of the first aspect,
$R^5$ and $R^6$ are independently selected from phenyl optionally substituted by OH, $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; $NR^{19}R^{21}$; $C(O)OR^{19}$; $C(O)R^{19}$; $SR^{19}$; $OR^{19}$; CN; $NO_2$; and halogen.

In an embodiment (xvi) of the first aspect,
$R^5$ and $R^6$ are independently selected from phenyl optionally substituted by $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; and halogen.

In an embodiment (xvii) of the first aspect,
$R^5$ and $R^6$ are independently selected from phenyl optionally substituted by $C_1$-$C_4$ alkoxy or halogen, and $C_1$-$C_4$ alkyl optionally substituted by one or more halogen atoms.

In an embodiment (xviii) of the first aspect,
$R^5$ and $R^6$ are independently selected from phenyl optionally substituted by methyl, ethyl, trifluoromethyl, methoxy or halogen.

In an embodiment (ixx) of the first aspect, $R^5$ is
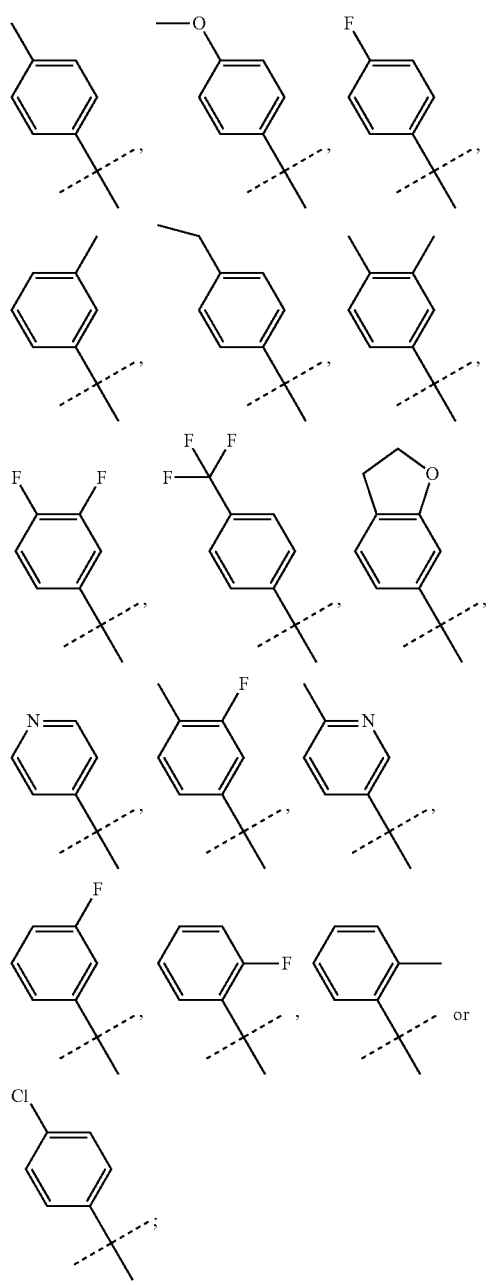
and $R^6$ is
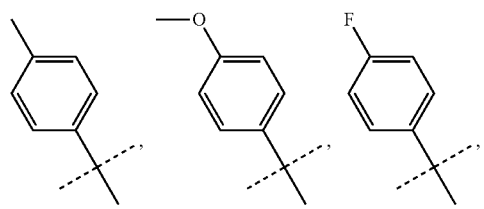
In an embodiment (xx) of the first aspect, A is N.
In an embodiment (xxi) of the first aspect, A is CR'.
In an embodiment (xxii) of the first aspect, R' is H.
In an embodiment (xxiii) of the first aspect, formula Ib has the following stereochemistry:
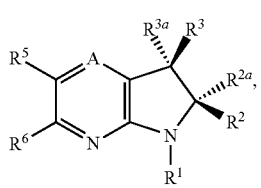
(Ib')
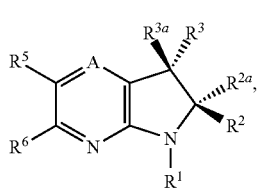
(Ib")
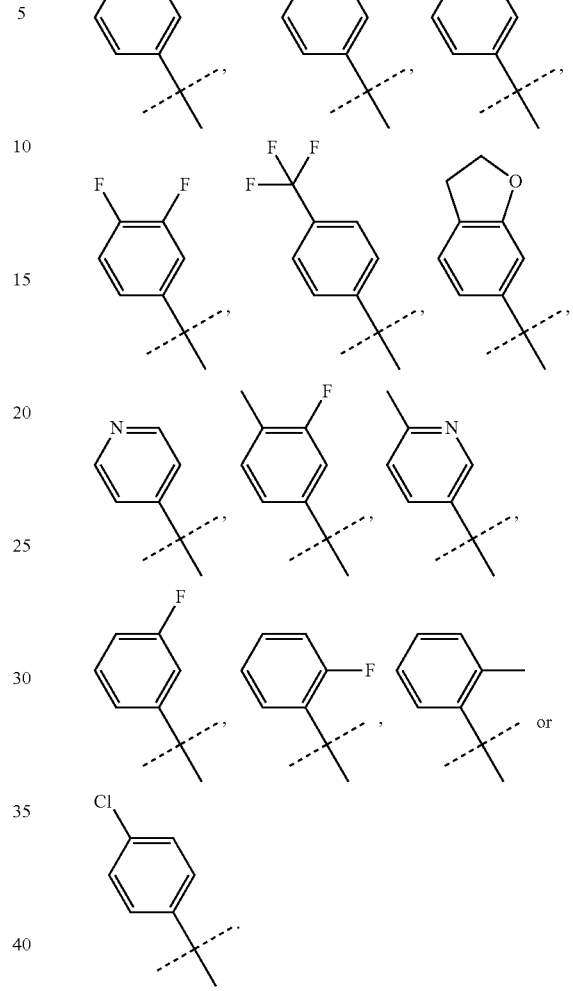

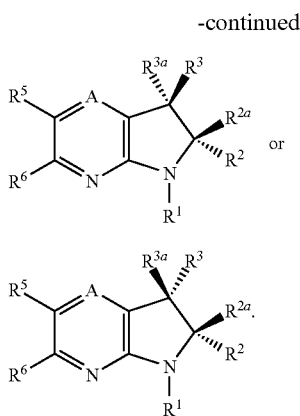

(Ib''')

(Ib'''')

In an embodiment (xxiv) of the first aspect, the compound is selected from 7-(6-cyclopropyl-2,3-di-p-tolyl-5H-pyrrolo[2,3-b]pyrazin-5-yl)heptanoic acid; ethyl 7-(6-cyclopropyl-2,3-di-p-tolyl-5H-pyrrolo[2,3-b]pyrazin-5-yl)heptanoate;

7-(6-isopropyl-2,3-di-p-tolyl-pyrrolo[2,3-b]pyrazin-5-yl)-heptanoic acid;

ethyl 7-(6-isopropyl-2,3-di-p-tolyl-5H-pyrrolo[2,3-b]pyrazin-5-yl)heptanoate;

7-(2,3-di-p-tolyl-pyrrolo[2,3-b]pyrazin-5-yl)-heptanoic acid ethyl ester;

7-(2,3-di-p-tolyl-pyrrolo[2,3-b]pyrazin-5-yl)-heptanoic acid;

7-(7-formyl-2,3-di-p-tolyl-5H-pyrrolo[2,3-b]pyrazin-5-yl)heptanoic acid;

7-(7-(hydroxymethyl)-2,3-di-p-tolyl-5H-pyrrolo[2,3-b]pyrazin-5-yl)heptanoic acid;

ethyl 7-(7-(hydroxymethyl)-2,3-di-p-tolyl-5H-pyrrolo[2,3-b]pyrazin-5-yl)heptanoate;

ethyl 7-(7-((isopropylamino)methyl)-2,3-di-p-tolyl-5H-pyrrolo[2,3-b]pyrazin-5-yl)heptanoate;

7-(7-((isopropylamino)methyl)-2,3-di-p-tolyl-5H-pyrrolo[2,3-b]pyrazin-5-yl)heptanoic acid;

7-(6-methoxy-2,3-di-p-tolyl-pyrrolo[2,3-b]pyrazin-5-yl)-heptanoic acid;

ethyl 7-(2,3-di-p-tolyl-6,7-dihydro-5H-pyrrolo[2,3-b]pyrazin-5-yl)heptanoate;

5-(2,3-di-p-tolyl-5H-pyrrolo[2,3-b]pyrazin-6-yl)-pentanoic acid;

2-(5-(2,3-di-p-tolyl-5H-pyrrolo[2,3-b]pyrazin-6-yl)pentanamido)acetic acid;

7-(6-methyl-2,3-di-p-tolyl-5H-pyrrolo[2,3-b]pyrazin-5-yl)heptanoic acid;

7-(6-cyclopropyl-2,3-diphenyl-pyrrolo[2,3-b]pyrazin-5-yl)-heptanoic acid;

7-(6-cyclopropyl-2-(4-methoxy-phenyl)-3-(p-tolyl)-5H-pyrrolo[2,3-b]pyrazin-5-yl)heptanoic acid;

7-(2,3-bis(4-chlorophenyl)-6-cyclopropyl-5H-pyrrolo[2,3-b]pyrazin-5-yl)heptanoic acid;

7-(6-cyclopropyl-2-(4-ethylphenyl)-3-(p-tolyl)-5H-pyrrolo[2,3-b]pyrazin-5-yl)heptanoic acid;

7-(6-cyclopropyl-2,3-di-m-tolyl-5H-pyrrolo[2,3-b]pyrazin-5-yl)heptanoic acid;

7-(6-cyclopropyl-3-(4-ethylphenyl)-2-(p-tolyl)-5H-pyrrolo[2,3-b]pyrazin-5-yl)heptanoic acid;

7-(6-cyclopropyl-3-(4-methoxyphenyl)-2-(p-tolyl)-5H-pyrrolo[2,3-b]pyrazin-5-yl)heptanoic acid;

7-(6-cyclopropyl-3-(m-tolyl)-2-(p-tolyl)-5H-pyrrolo[2,3-b]pyrazin-5-yl)heptanoic acid;

7-(6-cyclopropyl-2-(m-tolyl)-3-(p-tolyl)-5H-pyrrolo[2,3-b]pyrazin-5-yl)heptanoic acid;

7-(6-(2-Hydroxyethyl)-2,3-dip-tolyl-5H-pyrrolo[2,3-b]pyrazin-5-yl)heptanoic acid;

5-(6-Cyclopropyl-2,3-dip-tolyl-5H-pyrrolo[2,3-b]pyrazin-5-yl)pentanoic acid;

6-(6-Cyclopropyl-2,3-dip-tolyl-5H-pyrrolo[2,3-b]pyrazin-5-yl)hexanoic acid;

7-(7-(Methoxymethyl)-2,3-dip-tolyl-5H-pyrrolo[2,3-b]pyrazin-5-yl)heptanoic acid;

7-(6-oxo-2,3-dip-tolyl-6,7-dihydro-5H-pyrrolo[2,3-b]pyrazin-5-yl)heptanoic acid;

7-(2,3-Dip-tolyl-6-(trifluoromethyl)-5H-pyrrolo[2,3-b]pyrazin-5-yl)heptanoic acid; and 7-(6,7-Diethyl-2,3-di-p-tolyl-5H-pyrrolo[2,3-b]pyrazin-5-yl)heptanoic acid;

or a pharmaceutically acceptable salt thereof.

In a second aspect, the invention provides a compound as defined in the first aspect, or a pharmaceutically acceptable salt thereof, as defined anywhere herein for use as a medicament.

Activating the IP receptor has been shown to have a beneficial effect or treat the following diseases or disorders: PAH is selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septal defect (ASD), ventricular septal defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH); Raynaud's phenomenon, including Raynaud's disease and Raynaud's syndrome; fibrotic diseases, including pulmonary fibrosis, systemic sclerosis/scleroderma, hepatic fibrosis/cirrhosis, renal fibrosis; thrombotic diseases associated with excessive platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, preeclampsia, inflammation, prophylaxis against unwanted side effects of COX-1, COX-2 and non-selective COX inhibitors, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

Hence, in a third aspect of the invention, there is provided a compound as defined in the first aspect, or a pharmaceutically acceptable salt thereof, for use in the treatment of a disorder selected from the aforementioned diseases and disorders.

In an embodiment of the third aspect of the invention, there is provided a compound as defined in the first aspect, or a pharmaceutically acceptable salt thereof, for use in the treatment of PAH as described above.

In a fourth aspect of the present invention, there is provided the use of a compound as defined in the first aspect and in any of the aforementioned embodiments, or a pharmaceutically acceptable salt thereof, for the manufacture of a medicament for the treatment of pulmonary arterial hypertension.

An embodiment of the fourth aspect of the present invention provides for the use of a compound as defined in the first aspect and in any of the aforementioned embodiments, or a pharmaceutically acceptable salt thereof, for the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

In a fifth aspect, the present invention provides a method for the prevention or treatment of an IP receptor mediated condition or disease, particularly PAH, comprising administering an effective amount of at least one compound as described herein to a subject in need of such treatment. Such IP receptor mediated conditions or diseases are selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

Other IP receptor mediated conditions or diseases are selected from platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

As used herein, the term "pharmaceutically acceptable salts" refers to salts that retain the biological effectiveness and properties of the compounds of this invention and, which typically are not biologically or otherwise undesirable. In many cases, the compounds as defined in the first aspect are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate trifluoroacetate and xinafoate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, 1-hydroxy-2-naphtoic acid and sulfosalicylic acid.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, acetone or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds as defined in the first aspect, including their salts, can also be obtained in the form of their hydrates, or include other solvents used for their crystallization.

Compounds as defined in the first aspect that contain groups capable of acting as donors and/or acceptors for hydrogen bonds may be capable of forming co-crystals with suitable co-crystal formers. These co-crystals may be prepared from compounds as defined in the first aspect by known co-crystal forming procedures. Such procedures include grinding, heating, co-subliming, co-melting, or contacting in solution compounds as defined in the first aspect with the co-crystal former under crystallization conditions and isolating co-crystals thereby formed. Suitable co-crystal formers include those described in WO 2004/078163. Hence the invention further provides co-crystals comprising a compound of as defined in the first aspect.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds as defined in the first aspect into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Since the compounds as defined in the first aspect are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

Compounds as defined in the first aspect are either obtained in the free form, as a salt thereof, or as prodrug derivatives thereof.

When both a basic group and an acid group are present in the same molecule, the compounds as defined in the first aspect may also form internal salts, e.g., zwitterionic molecules.

The present invention also provides pro-drugs of the compounds as defined in the first aspect that converts in vivo to the compounds as defined in the first aspect. A pro-drug is an active or inactive compound that is modified chemically through in vivo physiological action, such as hydrolysis, metabolism and the like, into a compound of this invention following administration of the prodrug to a subject. The suitability and techniques involved in making and using prodrugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds as defined in the first aspect include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{125}$I respectively. The invention includes various isotopically labeled compounds as defined herein, for example those into which radioactive isotopes, such as $^3$H, $^{13}$C, and $^{14}$C, are present. Such isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound as defined in the first aspect. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds as defined in the first aspect can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Synthesis

Generally, compounds according to Formula I, or a pharmaceutically acceptable salt thereof, can be synthesized by the routes described in Schemes 1-5 and the Examples.

Scheme 1:

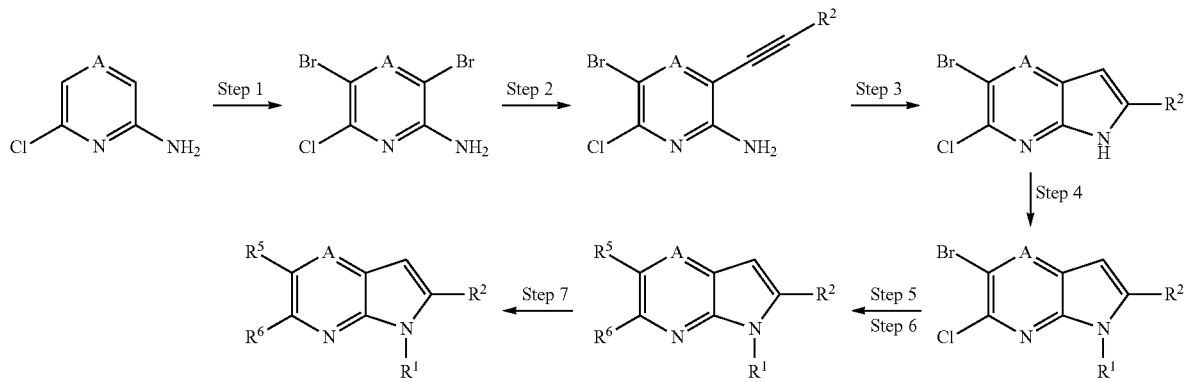

Scheme 1 begins with a Step 1 bromination. Step 2 is a Sonogashira coupling. Step 3 is a cyclisation. Step 4 is an alkylation. Steps 5 and 6 are subsequent Suzuki reactions. Step 7 is an ester hydrolysis if required. A, $R^1$, $R^2$, $R^5$ and $R^6$ are as defined in embodiment 1 of the consistory clauses.

Scheme 2:

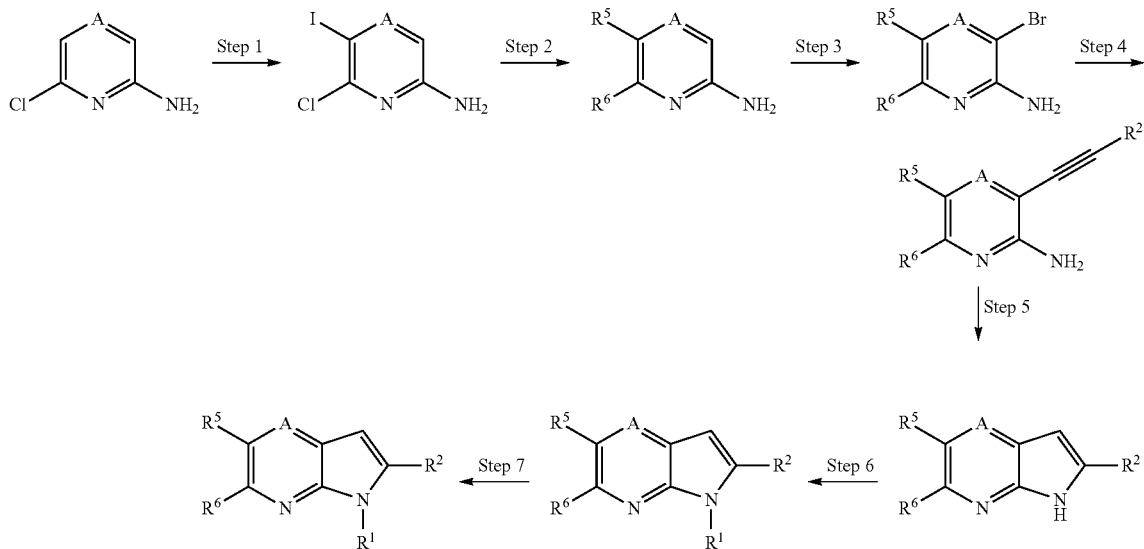

Scheme 2 begins with a Step 1 iodination. Step 2 is a Suzuki coupling. Step 3 is a bromination. Step 4 is a Sonogashira coupling. Step 5 is a cyclisation. Step 6 is an alkylation. Step 7 is an ester hydrolysis if required. A, $R^1$, $R^2$, $R^5$ and $R^6$ are as defined in embodiment 1 of the consistory clauses.

Scheme 3 begins with a Step 1 iodination. Step 2 is a Suzuki coupling. Step 3 is a bromination. Step 4 is a Sonogashira coupling. Step 5 is a cyclisation. Step 6 is an alkylation. Step 7 is either a Vilsmeyer formylation followed by reductive amination; or oxidation and then coupling; or reduction followed by an alkylation if required; or bromination followed by an alkylation, or suzuki coupling or Grignard, Step 8 is an ester hydrolysis if required. A, $R^1$, $R^2$, $R^3$, $R^5$ and $R^6$ are as defined in embodiment 1 of the consistory clauses.

Scheme 3:

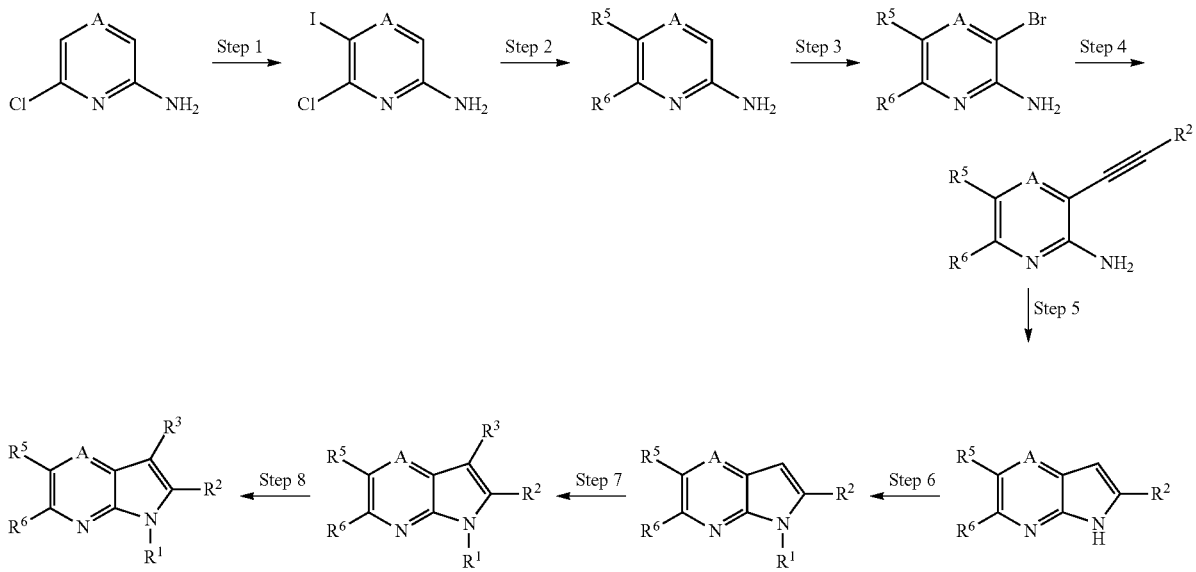

Scheme 4:

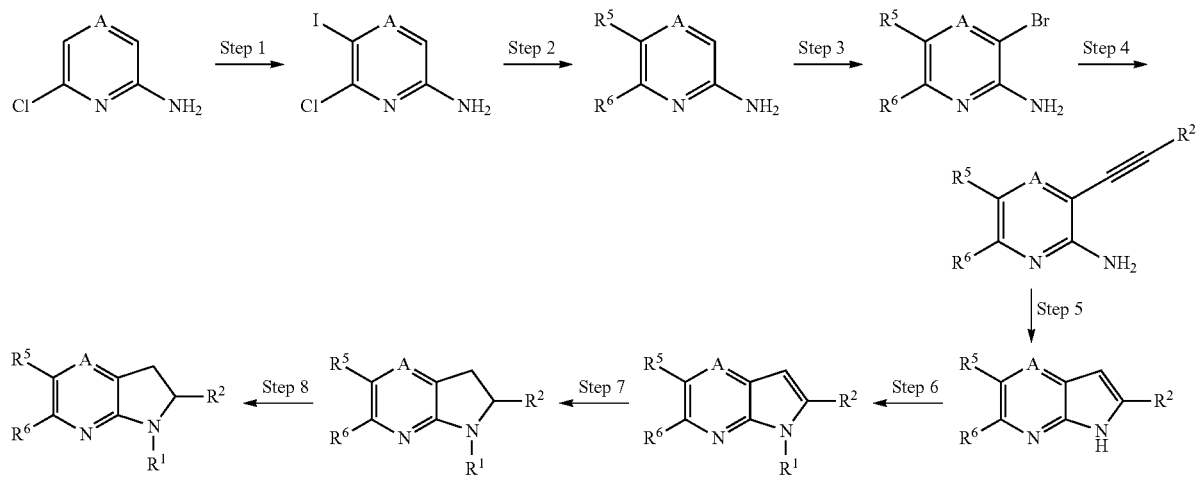

Scheme 4 begins with a Step 1 iodination. Step 2 is a Suzuki coupling. Step 3 is a bromination. Step 4 is a Sonogashira coupling. Step 5 is a cyclisation. Step 6 is an alkylation. Step 7 is a hydrogenation, Step 8 is an ester hydrolysis if required.

Scheme 5:

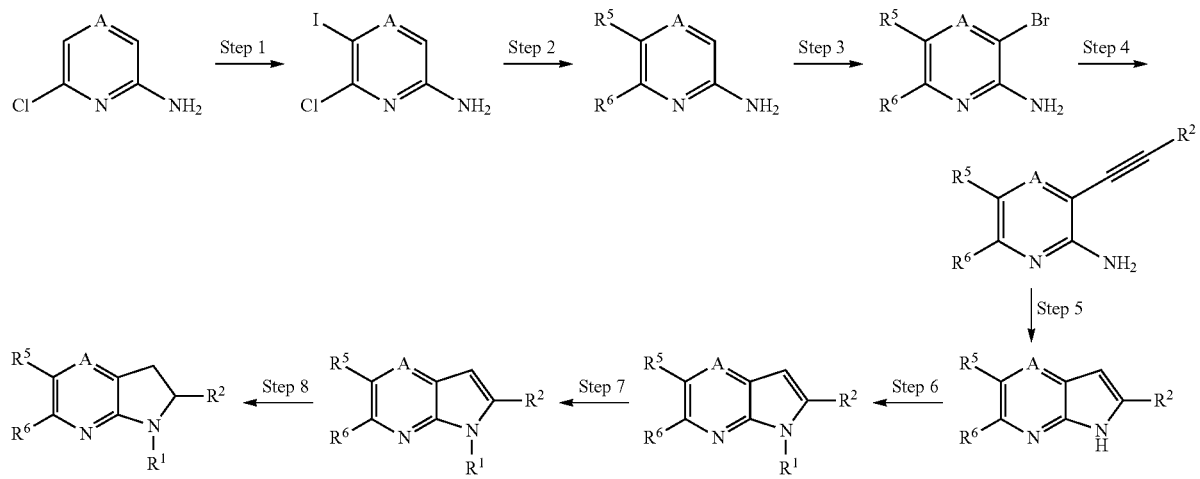

Scheme 5 begins with a Step 1 iodination. Step 2 is a Suzuki coupling. Step 3 is a bromination. Step 4 is a Sonogashira coupling. Step 5 is a cyclisation. Step 6 is an alkylation. Step 7 is an ester hydrolysis if required. Step 8 is a bromination (NBS) followed by a hydrogenation.

The skilled person will appreciate that the general synthetic routes detailed above show common reactions to transform the starting materials as required. The specific reaction conditions are not provided, but these are well known to those skilled in the art and appropriate conditions considered to be within the skilled person's common general knowledge.

The starting materials are either commercially available compounds or are known compounds and can be prepared from procedures described in the organic chemistry art.

Compounds as defined in the first aspect, in free form, may be converted into salt form, and vice versa, in a conventional manner understood by those skilled in the art. The compounds in free or salt form can be obtained in the form of hydrates or solvates containing a solvent used for crystallisation. Compounds as defined in the first aspect can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

Compounds as defined in the first aspect or a pharmaceutically acceptable salt thereof can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound as defined in the first aspect into another compound as defined in the first aspect. Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, $5^{th}$ Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons, $4^{th}$ Edition (2006).

Pharmacological Activity

The compounds disclosed herein activate the IP receptor and are useful in the treatment of several diseases and disorders, and in the amelioration of symptoms thereof.

Without limitation, these include the following:

Pulmonary Arterial Hypertension (PAH)

PAH has a multifactorial pathobiology. Vasoconstriction, remodeling of the pulmonary vessel wall, and thrombosis contribute to increased pulmonary vascular resistance in PAH (Humbert et al, J. Am. Coll. Cardiol., 2004, 43:13 S-24S.). The compounds as defined in the first aspect disclosed herein are useful in the treatment of pulmonary arterial hypertension (PAH) and symptoms thereof. PAH shall be understood to encompass the following forms of pulmonary arterial hypertension described in the 2003 World Health Organization (WHO) clinical classification of pulmonary arterial hypertension: idiopathic PAH (BPAH); familial PAH (FPAH); PAH associated with other conditions (APAH), such as PAH associated with collagen vascular disease, PAH associated with congenital systemic-to-pulmonary shunts, PAH associated with portal hypertension, PAH associated with HTV infection, PAH associated with drugs or toxins, or PAH associated with Other; and PAH associated with significant venous or capillary involvement. Idiopathic PAH refers to PAH of undetermined cause. Familial PAH refers to PAH for which hereditary transmission is suspected or documented. PAH associated with collagen vascular disease shall be understood to encompass PAH associated with scleroderma, PAH associated with CREST (calcinosis cutis, Raynaud's phenomenon, esophageal dysfunction, sclerodactyl), and telangiectasias) syndrome, PAH associated with systemic lupus erythematosus (SLE), PAH associated with rheumatoid arthritis, PAH associated with Takayasu's arteritis, PAH associated with polymyositis, and PAH associated with dermatomyositis. PAH associated with congenital systerruc-to-pulmonary shunts shall be understood to encompass PAH associated with atrial septal defect (ASD), PAH associated with ventricular septal defect (VSD) and PAH associated with patent ductus arteriosus.

PAH associated with drugs or toxins shall be understood to encompass PAH associated with ingestion of a minorex, PAH associated with ingestion of a fenfluramine compound (e.g., PAH associated with ingestion of fenfluramine or PAH associated with ingestion of dexfenfluramine), PAH associated with ingestion of certain toxic oils (eg, PAH associated with ingestion of rapeseed oil), PAH associated with ingestion of pyrrolizidine alkaloids (e.g, PAH associated with ingestion of bush tea) and PAH associated with ingestion of monocrotaline. PAH associated with Other shall be understood to encompass PAH associated with a thyroid disorder, PAH associated with glycogen storage disease, PAH associated with Gaucher disease, PAH associated with hereditary hemorrhagic telangiectasia, PAH associated with a hemoglobinopathy, PAH associated with a myeloproliferative disorder, and PAH associated with splenectomy. PAH associated with significant venous or capillary involvement shall be understood to encompass PAH associated with pulmonary veno-occlusive disease (PVOD) and PAH associated with pulmonary capillary hemangiomatosis (PCH). (See, e.g, Simonneau et al, J. Am. Coll. Cardiol., 2004, 43:5 S-12S; McGoon et al., Chest, 2004, 126:14 S-34S; Rabinovitch, Annu Rev. Pathol. Mech. Dis., 2007, 2:369-399; McLaughlin et al, Circulation, 2006, 114:1417-1431; Strauss et al, Clin. Chest. Med., 2007, 28:127-142; Taichman et al., Clin. Chest. Med., 2007, 28:1-22.).

Evidence for the association of PAH with scleroderma and the beneficial effect of an agonist of the IP receptor on PAH is given by Badesch et al (Badesch et al, Ann. Intern. Med., 2000, 132:425-434). Evidence for the association of PAH with the collagen vascular diseases mixed connective tissue disease (MCTD), systemic lupus erythematosus (SLE), Sjogren's syndrome and CREST syndrome and the beneficial effect of an agonist of the IP receptor on PAH is given by Humbert et al. (Eur. Respir. J., 1999, 13:1351-1356). Evidence for the association of PAH with CREST syndrome and the beneficial effect of an agonist of the IP receptor on PAH is given by Miwa et al. (Int. Heart J., 2007, 48:417-422). Evidence for the association of PAH with SLE and the beneficial effect of an agonist of the IP receptor on PAH is given by Robbins et al (Chest, 2000, 117:14-18). Evidence for the association of PAH with HIV infection and the beneficial of an agonist of the IP receptor on PAH is given by Aguilar et al. (Am. J. Respir. Crit. Care Med., 2000, 162:1846-1850). Evidence for the association of PAH with congenital heart defects (including ASD, VSD and patent ductus arteriosus) and the beneficial effect of an agonist of the IP receptor on PAH is given by Rosenzweig et al. (Circulation, 1999, 99:1858-1865).

Evidence for the association of PAH with fenfluramine and with dexfenfluramine, anorexigens, is given by Archer et al. (Am. J. Respir. Crit. Care Med., 1998, 158: 1061-1067). Evidence for the association of PAH with hereditary hemorrhagic telangiectasia is given by McGoon et al. (Chest, 2004, 126:14-34). Evidence for the association of PAH with splenectomy is given by Hoeper et al. (Ann. Intern. Med., 1999, 130:506-509). Evidence for the association of PAH with portal hypertension and the beneficial effect of an agonist of the IP receptor on PAH is given by Hoeper et al. (Eur. Respir. J., 2005, 25:502-508).

Symptoms of PAH include dyspnea, angina, syncope and edema (McLaughlin et al., Circulation, 2006, 114:1417-1431). The compounds as defined in the first aspect disclosed herein are useful in the treatment of symptoms of PAH.

Antiplatelet Therapies (Conditions Related to Platelet Aggregation)

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction, the heart muscle does not receive enough oxygen-rich blood as a result of a blockage in the coronary blood vessels. If taken while an attack is in progress or immediately afterward (preferably within 30 min), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs. Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes. Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

There is evidence that an IP receptor agonist will inhibit platelet aggregation and thus be a potential treatment as an antiplatelet therapy (see, e.g., Moncada et al., Lancet, 1977, 1: 18-20). It has been shown that genetic deficiency of the IP receptor in mice leads to an increased propensity towards thrombosis (Murata et al, Nature, 1997, 388:678-682).

IP receptor agonists can be used to treat, for example, claudication or peripheral artery disease as well as cardiovascular complications, arterial thrombosis, atherosclerosis, vasoconstriction caused by serotonin, ischemia-reperfusion injury, and restenosis of arteries following angioplasty or stent placement. (See, e.g., Fetalvero et al, Prostaglandins Other Lipid Mediat., 2007, 82:109-118; Arehart et al, Curr. Med. Chem., 2007, 14:2161-2169; Davi et al, N. Engl. J. Med., 2007, 357:2482-2494; Fetalvero et al, Am. J. Physiol. Heart. Circ. Physiol., 2006, 290:H1337-H1346; Murata et al, Nature, 1997, 388:678-682; Wang et al, Proc. Natl. Acad. Sci. USA, 2006, 103:14507-14512; Xiao et al, Circulation, 2001, 104:2210-2215; McCormick et al, Biochem. Soc. Trans., 2007, 35:910-911; Arehart et al, Circ. Res., 2008, Mar. 6.).

IP receptor agonists can also be used alone or in combination with thrombolytic therapy, for example, tissue-type plasminogen activator (t-PA), to provide cardioprotection following MI or postischemic myocardial dysfunction or protection from ischemic injury during percutaneous coronary intervention, and the like, including complications resulting therefrom. IP receptor agonists can also be used in antiplatelet therapies in combination with, for example, alpha-tocopherol (vitamin E), echistatin (a disintegrin) or, in states of hypercoagulability, heparin. (See, e.g., Chan., J. Nutr., 1998, 128: 1593-1596; Mardla et al, Platelets, 2004, 15:319-324; Bernabei et al, Ann. Thorac. Surg., 1995, 59:149-153; Gainza et al, J. Nephrol., 2006, 19:648-655.)

The IP receptor agonists disclosed herein may provide beneficial improvement in microcirculation to patients in need of antiplatelet therapy by antagonizing the vasoconstrictive products of the aggregating platelets in, for example and not limited to the indications described above.

Accordingly, in some embodiments, the present invention provides methods for reducing platelet aggregation in a patient in need thereof, comprising administering to the patient a composition comprising an IP receptor agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising an IP receptor agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising an IP receptor agonist disclosed herein at a time where such risk exists.

Atherosclerosis

Atherosclerosis is a complex disease characterized by inflammation, lipid accumulation, cell death and fibrosis. It is the leading cause of mortality in many countries, including the United States. Atherosclerosis, as the term is used herein, shall be understood to encompass disorders of large and medium-sized arteries that result in the progressive accumulation within the intima of smooth muscle cells and lipids.

It has been shown that an agonist of the IP receptor can confer protection from atherosclerosis, such as from atherothrombosis (Arehart et al, Curr. Med. Chem., 2007, 14:2161-2169; Stitham et al, Prostaglandins Other Lipid Mediat., 2007, 82:95-108; Fries et al, Hematology Am. Soc. Hematol. Educ. Program, 2005:445-451; Egan et al, Science, 2004, 306:1954-1957; Kobayashi et al, J. Clin. Invest, 2004, 114: 784-794; Arehart et al, Circ. Res., 2008, Mar. 6). It has been shown that defective IP receptor signaling appears to accelerate atherothrombosis in humans, i e that an agonist of the IP receptor can confer protection from atherothrombosis in humans (Arehart et al, Circ. Res., 2008, Mar. 6.)

The compounds as defined in the first aspect disclosed herein are useful in the treatment of atherosclerosis, and the treatment of the symptoms thereof. Accordingly, in some embodiments, the present invention provides methods for treating atherosclerosis in a patient in need of the treatment, comprising administering to the patient a composition comprising an IP receptor agonist disclosed herein. In further embodiments, methods are provided for treating a symptom of atherosclerosis in a patient in need of the treatment, comprising administering to the patient a composition comprising an IP receptor agonist disclosed herein.

Asthma

Asthma is a lymphocyte-mediated inflammatory airway disorder characterised by airway eosinophilia, increased mucus production by goblet cells, and structural remodeling of the airway wall. The prevalence of asthma has dramatically increased worldwide in recent decades. It has been shown that genetic deficiency of the IP receptor in mice augments allergic airway inflammation (Takahashi et al, Br J Pharmacol, 2002, 137:315-322). It has been shown that an agonist of the IP receptor can suppress not only the development of asthma when given during the sensitization phase, but also the cardinal features of experimental asthma when given during the challenge phase (Idzko et al, J. Clin. Invest., 2007, 117:464-72, Nagao et al, Am. J. Respir. Cell Mol. Biol., 2003, 29:314-320), at least in part through markedly interfering with the function of antigen-presenting dendnuc cells within the airways (Idzko et al., J. Clin. Invest., 2007, 117:464-472; Zhou et al, J. Immunol., 2007, 178:702-710; Jaffar et al., J. Immunol., 2007, 179:6193-6203; Jozefowski et al, Int. Immunopharmacol., 2003, 3:865-878). These cells are crucial for both the initiation and the maintenance phases of allergic asthma, as depletion of airway dendritic cells during secondary challenge in sensitized mice abolished all characteristic features of asthma, an effect that could be completely restored by adoptive transfer of wild-type dendritic cells (van Rijt et al., J. Exp. Med., 2005, 201:981-991). It has also been shown that an agonist of the IP receptor can inhibit proinflammatory cytokine secretion by human alveolar macrophages (Raychaudhuri et al., J. Biol. Chem., 2002, 277:33344-33348). The compounds as defined in the first aspect disclosed herein are useful in the treatment of asthma, and the treatment of the symptoms thereof. Accordingly, in some embodiments, the present invention provides methods for treating asthma in a patient in need of the treatment, comprising administering to the patient a composition comprising IP receptor agonist disclosed herein.

In further embodiments, methods are provided for treating a symptom of asthma in a patient in need of the treatment, comprising administering to the patient a composition comprising IP receptor agonist disclosed herein.

Chronic Obstructive Pulmonary Disease

Activation of the IP-receptor may also be beneficial in chronic obstructive pulmonary disease (COPD). Taprostene, an IP-receptor agonist, suppressed the generation of the $CD8^+$ T cell chemoattractants CXCL9 and CXCL10 from human airway epithelial cells in vitro. (Ayer, L. M., S. M. Wilson, S. L. Traves, D. Proud, M. A. Giembycz. 2008. J. Pharmacol. Exp. Ther. 324: 815-826.) Beraprost, an IP-receptor agonist, protected rats against the development of experimental cigarette smoke-induced emphysema, possibly by means of a concerted inhibitory action on alveolar epithelial cell apoptosis, oxidative burden, matrix metalloproteinase expression, and proinflammatory cytokine generation. (Chen, Y, M Hanaoka, P. Chen, Y. Droma, N. F. Voelkel, K. Kubo. 2009. Am. J. Physiol. 296: L648-L656.)

In further embodiments, methods are provided for treating COPD in a patient in need of the treatment, comprising administering to the patient a composition comprising IP receptor agonist disclosed herein.

Hyperglycemia

Although hyperglycemia is the major cause for the pathogenesis of diabetic complications such as diabetic peripheral neuropathy (DPN), diabetic nephropathy (DN) and diabetic retinopathy (DR), enhanced vasoconstriction and platelet aggregation in diabetic patients has also been implicated to play a role in disease progression (Cameron et al., Naunyn Schmiedebergs Arch. Pharmacol., 2003, 367:607-614). Agonists of the IP receptor promote vasodilation and inhibit platelet aggregation. Improving microvascular blood flow is able to benefit diabetic complications (Cameron, Diabetologia, 2001, 44:1973-1988).

It has been shown that an agonist of the IP receptor can prevent and reverse motor and sensory peripheral nerve conduction abnormalities in streptozotocin-diabetic rats (Cotter et al., Naunyn Schmiedebergs Arch. Pharmacol., 1993, 347: 534-540). Further evidence for the beneficial effect of an agonist of the IP receptor in the treatment of diabetic peripheral neuropathy is given by Hotta et al. (Diabetes, 1996, 45:361-366), Ueno et al. (Jpn. J. Pharmacol., 1996, 70:177-182), Ueno et al. (Life Sci., 1996, 59:PL105-PL110), Hotta et al. (Prostaglandins, 1995, 49:339-349), Shindo et al. (Prostaglandins, 1991, 41:85-96), Okuda et al. (Prostaglandins, 1996, 52:375-384), and Koike et al. (FASEB J., 2003, 17:779-781).

Evidence for the beneficial effect of an agonist of the IP receptor in the treatment of diabetic nephropathy is given by Owada et al. (Nephron, 2002, 92:788-796) and Yamashita et al. (Diabetes Res. Clin. Pract., 2002, 57:149-161). Evidence for the beneficial effect of an agonist of the IP receptor in the treatment of diabetic retinopathy is given by Yamagishi et al. (Mol. Med., 2002, 8:546-550), Burnette et al. (Exp. Eye Res., 2006, 83: 1359-1365), and Hotta et al. (Diabetes, 1996, 45:361-366). It has been shown that an agonist of the IP receptor can reduce increased tumor necrosis factor-[alpha] (TNF-[alpha]) levels in diabetic patients, implying that an agonist of the IP receptor may contribute to the prevention of progression in diabetic complications (Fujiwara et al, Exp. Clin. Endocrinol. Diabetes, 2004, 112:390-394).

Evidence that topical administration of an agonist of the IP receptor can result in a decrease in intraocular pressure (IOP) in rabbits and dogs and thereby have beneficial effect in the treatment of glaucoma is given by Hoyng et al (Hoyng et al, Invest. Ophthalmol. Vis. Sci., 1987, 28:470-476).

Agonists of the IP receptor have been shown to have activity for regulation of vascular tone, for vasodilation, and for amelioration of pulmonary hypertension (see, e.g., Strauss et al, Clin Chest Med, 2007, 28:127-142; Driscoll et al, Expert Opin. Pharmacother., 2008, 9:65-81). Evidence for a beneficial effect of an agonist of the IP receptor in the treatment of hypertension is given by Yamada et al. (Peptides, 2008, 29:412-418). Evidence that an agonist of the IP receptor can protect against cerebral ischemia is given by Dogan et al. (Gen. Pharmacol., 1996, 27:1163-1166) and Fang et al (J. Cereb. Blood Flow Metab., 2006, 26:491-501).

Anti-Inflammation

Anti-inflammation agents are prescribed for a variety of conditions. For example, in an inflammatory disease they are used to interfere with and thereby reduce an underlying deleterious.

There is evidence that an IP receptor agonist can inhibit inflammation and thus be a potential treatment as an anti-inflammation therapy. It has been shown that an agonist of the IP receptor can inhibit pro-inflammatory cytokine and chemokine (interleukin-12 (IL-12), tumor necrosis factor-[alpha] (TNF-[alpha]), DL-1[alpha], EL-6, macrophage inflammatory protein-1 alpha (MIP-1[alpha]), monocyte chemoattractant protein-1 (MCP-I)) production and T cell stimulatory function of dendritic cells (Jozefowski et al, Int. Immunopharmacol., 2003, 865-878; Zhou et al, J. Immunol., 2007, 178:702-710; Nagao et al, Am. J. Respir. Cell MoI. Biol., 2003, 29:314-320; Idzko et al, J. Clin. Invest., 2007, 117:464-472). It has been shown that an agonist of the IP receptor can inhibit pro-inflammatory cytokine (TNF-[alpha], IL-1/3, EL-6, granulocyte macrophage stimulating factor (GM-CSF)) production by macrophages (Raychaudhuri et al, J. Biol. Chem., 2002, 277:33344-33348; Czeslick et al, Eur. J. Clin. Invest., 2003, 33:1013-1017; Di Renzo et al, Prostaglandin Leukot. Essent. Fatty Acids, 2005, 73:405-410; Shinomiya et al, Biochem. Pharmacol., 2001, 61:1153-1160). It has been shown that an agonist of the IP receptor can stimulate anti-inflammatory cytokine (DL-IO) production by dendritic cells (Jozefowski et al, Int. Immunopharmacol., 2003, 865-878; Zhou et al, J. Immunol., 2007, 178:702-710). It has been shown that an agonist of the IP receptor can stimulate anti-inflammatory cytokine (DL-10) production by macrophages (Shinomiya et al, Biochem. Pharmacol., 2001, 61: 1153-1160). It has been shown that an agonist of the IP receptor can inhibit a chemokine (CCL 17)-induced chemotaxis of leukocytes (CD4<+>Th2 T cells) (Jaffar et al, J. Immunol., 2007, 179:6193-6203). It has been shown that an agonist of the IP receptor can confer protection from atherosclerosis, such as from atherothrombosis (Arehart et al, Curr. Med. Chem., 2007, 14:2161-2169; Stitham et al, Prostaglandins Other Lipid Mediat., 2007, 82:95-108; Fries et al, Hematology Am. Soc. Hematol. Educ. Program, 2005:445-451; Egan et al, Science, 2004, 306:1954-1957; Kobayashi et al, J. Clin. Invest., 2004, 114:784-794; Arehart et al, Circ. Res., 2008, Mar. 6). It has been shown that an agonist of the IP receptor can attenuate asthma (Idzko et al, J. Clin. Invest., 2007, 117:464-472; Jaffar et al, J. Immunol., 2007, 179:6193-6203; Nagao et al, Am. J. Respir. Cell. MoI. Biol., 2003, 29:314-320). It has been shown that an agonist of the IP receptor can decrease TNF-[alpha] production in type 2 diabetes patients (Fujiwara et al, Exp. Clin. Endocrinol. Diabetes, 2004, 112:390-394; Goya et al, Metabolism, 2003, 52: 192-198). It has been shown that an agonist of the IP receptor can inhibit ischemia-reperfusion injury (Xiao et al, Circulation, 2001, 104:2210-2215). It has been shown that an agonist of the IP receptor can inhibit restenosis (Cheng et al, Science, 2002, 296:539-541). It has been shown that an agonist of the IP receptor can attenuate pulmonary vascular injury and shock in a rat model of septic shock (Harada et al, Shock, 2008, Feb. 21). It has been shown that an agonist of the IP receptor can reduce the serum levels of TNF-[alpha] in vivo in patients with rheumatoid arthritis, and this is associated with improvement in the clinical course of the disease (Gao et al, Rheumatol. Int., 2002, 22:45-51; Boehme et al, Rheumatol. Int., 2006, 26:340-347).

The compounds as defined in the first aspect disclosed herein provide beneficial reduction of inflammation. The compounds as defined in the first aspect disclosed herein provide beneficial reduction of a deleterious inflammatory response associated with an inflammatory disease. Accordingly, in some embodiments, the present invention provides methods for reducing inflammation in a patient in need thereof, comprising administering to the patient a composition comprising an IP receptor agonist disclosed herein. In some embodiments, the present invention provides methods for decreasing IL-12, TNF-[alpha], IL-1 [alpha], IL-IjS, BL-6, MIP-Ia or MCP-I production in a patient in need thereof, comprising administering to the patient a composition comprising an IP receptor agonist disclosed herein. In some embodiments, the present invention provides methods for decreasing TNF-[alpha] production in a patient in need thereof, comprising administering to the patient a composition comprising an IP receptor agonist disclosed herein. In some embodiments, the present invention provides methods for increasing EL-IO production in a patient in need thereof, comprising administering to the patient a composition comprising an IP receptor agonist disclosed herein. In some embodiments, the present invention provides methods for reducing a deleterious inflammatory response associated with an inflammatory disease in a patient in need thereof, comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein, wherein the inflammatory disease is selected from the group consisting of psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, diabetes (including type 1 diabetes and type 2 diabetes), sepsis, chronic obstructive pulmonary disease (COPD), and asthma.

Fibrosis

PGI2 signaling has been shown to play a beneficial role in fibrotic diseases of various organs, including kidney, heart, lung, skin, pancreas and liver, as well as in systemic sclerosis and associated pathologies. It has been shown that an agonist of the IP receptor can ameliorate cardiac fibrosis (Chan E C et al (2010) *J Mol Cell Cardiol.* April 18; Hirata Y et al (2009) *Biomed Pharmacother.* 63(10):781-6; Kaneshige T et al (2007) *J Vet Med. Sci.* 69(12):1271-6). It has been shown that an agonist of the IP receptor can attenuate renal fibrosis (Takenaka M et al (2009) Prostaglandins Leukot Essent Fatty Acids. 80(5-6):263-7). It has been shown that an agonist of the IP receptor can protect against pulmonary fibrosis in a bleomycin model (Zhu Y et al (2010) *Respir Res.* 20; 11(1): 34). It has been shown that an agonist of the IP receptor can suppress the production of connective tissue growth factor, a key mediator of fibrosis, in scleroderma patients (Stratton R et al (2001) *J Clin Invest.* 108(2):241-50). It has been shown that an agonist of the IP receptor can reduce the incidence of digital ulcerations in patients with systemic sclerosis M. Vayssairat (1999) *J Rheumatol* 26:2173-2178. It has been shown that an agonist of the IP receptor can reduce fingertip necrosis in infants with refractory Renaud's phenomenon (Shouval D S et al (2008) *Clin Exp Rheumatol.* 26(3 Suppl 49):5105-7). It has been shown that an agonist of the IP receptor can reduce markers of endothelial activation in patients with systemic sclerosis (Rehberger P et al (2009) *Acta Derm Venereol.* 89(3):245-9.). It has been shown that an agonist of the IP receptor can reduce severity, frequency, and duration of Raynaud's attacks in patients with systemic sclerosis (Torlay et al (1991) *Ann Rheum Dis* 50, 800-804). It has been shown that an agonist of the IP receptor can improve portal hemodynamics in patients with systemic sclerosis and Raynaud's phenomenon (Zardi et al (2006) *In Vivo* 20(3):377-80). It has been shown that an agonist of the IP receptor can inhibit the progression of pancreatic fibrosis in obese Zucker rats (Sato et al (2010) *Diabetes* 59(4):1092-100).

The IP receptor agonists disclosed herein may provide beneficial anti-fibrotic effects to patients suffering from fibrosis of the kidney, heart, lung, skin, pancreas and liver which can be idiopathic or secondary to chronic inflammation and systemic sclerosis, for example, and are not limited to the indications described above.

In addition, there is substantial evidence that an agonist of the IP receptor can improve kidney function in acute and chronic renal failure. It has been shown that an agonist of the IP receptor can restore kidney function in endotoxemia-related acute renal failure (Johannes T et al (2009) *Crit. Care Med.* 37(4):1423-32). It has been shown that an agonist of the IP receptor can improve renal function in a model of renal ischemia/reperfusion injury Sahsivar M O et al (2009) *Shock* 32(5):498-502). It has been shown that an agonist of the IP receptor can prevent contrast agent-induced nephropathy in patients with renal dysfunction undergoing cardiac surgery (Spargias K et al (2009) *Circulation* 3; 120(18):1793-9.) It has been shown that an agonist of the IP receptor can improve renal function, reduce inflammation and sclerotic changes of the kidney in a model for diabetic nephropathy Watanabe M et al (2009) Am J. Nephrol. 2009; 30(1):1-11).

The IP receptor agonists disclosed herein may provide beneficial improvement of renal function in patients with acute and chronic kidney injury and nephropathies secondary to dye-contrast agents, ischemia-reperfusion injury, systemic inflammation and diabetes for example, and are not limited to the indications described above.

There is considerable evidence for a causal role of Prostacyclin deficiency in the development of preeclampsia (Mills J L et al (1999) *JAMA* 282: 356-362; Walsh S W (2004) *Prostaglandins Leukot Essent Fatty Acids* 70: 223-232). The administration of an agonist of the IP receptor has been shown to lower blood pressure in a rat model of preeclampsia (Zlatnik M G et al (1999) *Am J Obstet. Gynecol.* 180(5):1191-5).

The IP receptor agonists disclosed herein may provide beneficial improvement of hemodynamics in patients with preeclampsia.

The IP receptor agonist disclosed herein may provide beneficial treatment of cystic fibrosis.

The IP receptor agonists disclosed herein may provide chemoprevention. Chemoprevention is the practice of using of drugs, vitamins, or nutritional supplements to reduce the risk of developing, or having a recurrence of cancer. Oral iloprost (Ventavis), an analogue of prostacyclin, shows promise as a chemopreventive agent for lung cancer. Data supporting IP receptor agonist chemoprevention was presented by Paul Bunn Jr. MD, who is the executive Director of the International Association for the Study of Lung Cancer at the American Association for Cancer Research 102nd Annual Meeting showed that it significantly improved endobronchial dysplasia in former smokers.

PGI2 and other IP receptor agonists, including the compounds as defined in the first aspect, are also useful as co-therapeutic agents for use in combination with second agents, such as organic nitrates and NO-donors, such as sodium nitroprusside, nitroglycerin, isosorbide mononitrate, isosorbide dinitrate, molsidomine or SIN-1, and inhalational NO; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil; NO-independent, but haem-dependent stimulators of guanylate cyclase, such as in particular the compounds described in WO 00/06568, WO 00/06569, WO 02/42301 and WO 03/095451; NO- and haem-independent activators of guanylate cyclase, such as in particular the compounds described in WO 01/19355, WO 01/19776, WO 01/19778, WO 01/19780, WO 02/070462 and WO 02/070510; compounds which inhibit human neutrophilic elastase, such as sivelestat or DX-890 (Reltran); compounds inhibiting the signal transduction cascade, such as tyrosine kinase and/or serine/threonine kinase inhibitors, in particular imatinib, gefitinib, erlotinib, sorafenib and sunitinib; compounds influencing the energy metabolism of the heart, for example and preferably etomoxir, dichloroacetate, ranolazine or trimetazidine; antithrombotic agents, for example and preferably from the group comprising platelet aggregation inhibitors, anticoagulants or profibrinolytic substances; active substances for lowering blood pressure, for example and preferably from the group comprising calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists, particularly in the treatment of PAH or diseases and disorders such as those mentioned hereinbefore, e.g., as potentiators of therapeutic activity of such drugs or as a means of reducing required dosaging or potential side effects of such drugs.

In particular, an embodiment of this invention is a pharmaceutical combination comprising the compounds as defined in the first aspect, or a pharmaceutically acceptable salt thereof, and a second agent wherein the second agent is a PDEV inhibitor or neutral endopeptidase inhibitor.

The compounds as defined in the first aspect, or a pharmaceutically acceptable salt thereof, may be mixed with a second agent in a fixed pharmaceutical composition or it may be administered separately, before, simultaneously with or after the other drug substance.

Accordingly, the invention includes as a further aspect a combination of an IP receptor activity with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the IP receptor agonist and the further drug substance may be in the same or different pharmaceutical composition.

Suitable antibiotics include macrolide antibiotics, e.g., tobramycin (TOBIT™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of IP receptor agonist with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl]tetrahydro-N,N-dimethyl-2H-pyran-4-aminium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, for example corticosteroids. Suitable steroids include budesonide, beclamethasone (e.g. dipropionate), butixocort (e.g. propionate), CHF5188, ciclesonide, dexamethasone, flunisolide, fluticasone (e.g. propionate or furoate), GSK-685698, GSK-870086, LAS40369, methyl prednisolone, mometasone (e.g. furoate), prednisolone, rofleponide, and triamcinolone (e.g. acetonide). In certain preferred embodiments the steroid is long-acting corticosteroids such as budesonide, ciclesonide, fluticasone or mometasone.

Suitable second active ingredients include $\beta_2$-agonists. Suitable $\beta_2$-agonists include arformoterol (e.g. tartrate), albuterol/salbutamol (e.g. racemate or single enantiomer such as the R-enantiomer, or salt thereof especially sulfate), AZD3199, bambuterol, BI-171800, bitolterol (e.g. mesylate), carmoterol, clenbuterol, etanterol, fenoterol (e.g. racemate or single enantiomer such as the R-enantiomer, or salt thereof especially hydrobromide), flerbuterol, formoterol (e.g. racemate or single diastereomer such as the R,R-diastereomer, or salt thereof especially fumarate or fumarate dihydrate), GSK-159802, GSK-597901, GSK-678007, indacaterol (e.g. racemate or single enantiomer such as the R-enantiomer, or salt thereof especially maleate, acetate or xinafoate), LAS100977, metaproterenol, milveterol (e.g. hydrochloride), naminterol, olodaterol (e.g. racemate or single enantiomer such as the R-enantiomer, or salt thereof especially hydrochloride), PF-610355, pirbuterol (e.g. acetate), procaterol, reproterol, salmefamol, salmeterol (e.g. racemate or single enantiomer such as the R-enantiomer, or salt thereof especially xinafoate), terbutaline (e.g. sulphate) and vilanterol (or a salt thereof especially trifenatate. In certain preferred embodiments the $\beta_2$-agonist is an ultra-long-acting $\beta_2$-agonist such as indacaterol, or potentially carmoterol, LAS-100977, milveterol, olodaterol, PF-610355 or vilanterol. A preferred embodiment one of the second active ingredients is indacaterol (i.e. (R)-5-[2-(5,6-diethyl-indan-2-ylamino)-1-hydroxyethyl]-8-hydroxy-1H-quinolin-2-one) or a salt thereof. This is a $\beta_2$-adrenoceptor agonist that has an especially long duration of action (i.e. over 24 hours) and a short onset of action (i.e. about 10 minutes). This compound is prepared by the processes described in international patent applications WO 2000/75114 and WO 2005/123684. It is capable of forming acid addition salts, particularly pharmaceutically acceptable acid addition salts. A preferred salt of (R)-5-[2-(5,6-diethyl-indan-2-ylamino)-1-hydroxyethyl]-8-hydroxy-1H-quinolin-2-one is the maleate salt. Another preferred salt is (R)-5-[2-(5,6-diethyl-indan-2-ylamino)-1-hydroxyethyl]-8-hydroxy-1H-quinolin-2-one acetate. Another preferred salt is (R)-5-[2-(5,6-diethyl-indan-2-ylamino)-1-hydroxyethyl]-8-hydroxy-1H-quinolin-2-one xinafoate.

Suitable bronchodilatory drugs include anticholinergic or antimuscarinic agents, such as aclidinium (e.g. bromide), BEA-2108 (e.g. bromide), BEA-2180 (e.g. bromide), CHF-5407, darifenacin (e.g. bromide), darotropium (e.g. bromide), glycopyrrolate (e.g. racemate or single enantiomer, or salt thereof especially bromide), dexpirronium (e.g. bromide), iGSK-202405, GSK-203423, GSK-573719, GSK-656398, ipratropium (e.g. bromide), LAS35201, LAS186368, otilonium (e.g. bromide), oxitropium (e.g. bromide), oxybutynin, PF-3715455, PF-3635659, pirenzepine, revatropate (e.g. hydrobromide), solifenacin (e.g. succinate), SVT-40776, TD-4208, terodiline, tiotropium (e.g. bromide), tolterodine (e.g. tartrate), and trospium (e.g. chloride). In certain preferred embodiments the muscarinic antagonists is long-acting muscarinic antagonist such as darotropium bromide, glycopyrrolate or tiotropium bromide.

Suitable dual anti-inflammatory and bronchodilatory drugs include dual beta-2 adrenoceptor agonist/muscarinic antagonists such as GSK-961081 (e.g. succinate). and those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Accordingly, the invention includes as a further aspect a combination of IP receptor agonist with agents that inhibit ALK5 and/or ALK4 phosphorylation of Smad2 and Smad3.

Accordingly, the invention includes as a further aspect a combination of IP receptor agonist with second agents that are Rho-kinase inhibitors.

Accordingly, the invention includes as a further aspect a combination of IP receptor agonist with second agents that are tryptophan hydroylase 1 (TPH1) inhibitors.

Accordingly, the invention includes as a further aspect a combination of IP receptor agonist with second agents that are multi-kinase inhibitors, such as imatinib mysilate, Gleevec. Imatinib functions as a specific inhibitor of a number of tyrosine kinase enzymes. It occupies the TK active site, leading to a decrease in activity. TK enzymes in the body include the insulin receptor. Imatinib is specific for the TK domain in the Abelson proto-oncogene, c-kit and PDGF-R (platelet-derived growth factor receptor).

In an embodiment of this invention, the IP receptor agonist of this invention are dosed in combination with a second active agent selected from phosphodiesterase V inhibitors, neutral endopeptidase 1 inhibitors, THP1 inhibitors, multi-kinase inhibitors, endothelin antagonist, diuretic, aldosteron receptor blocker, and endothelin receptor blocker.

In an embodiment of this invention, the IP receptor agonist of this invention are dosed in combination with a second active agent selected from phosphodiesterase V inhibitors, neutral endopeptidase 1 inhibitors, THP1 inhibitors, and multi-kinase inhibitors, such as PDGFR or c-Kit.

In another aspect the invention provides a compound as defined in the first aspect, or a pharmaceutically acceptable salt thereof, for use in the manufacture of a medicament for the treatment of a condition responsive to IP receptor agonist activity, particularly in PAH.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound as defined in the first aspect, in free form or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or antitussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound as defined in the first aspect or a pharmaceutically acceptable salt thereof having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound as defined in the first aspect or a pharmaceutically acceptable salt thereof either dissolved, or suspended, in a vehicle containing water, a co-solvent, such as ethanol or propylene glycol and a stabilizer, which may be a surfactant.

Further aspects of the invention include:
(a) a compound as defined in the first aspect or a pharmaceutically acceptable salt thereof in inhalable form, e.g., in an aerosol or other atomisable composition or in inhalable particulate, e.g., micronised form;
(b) an inhalable medicament comprising a compound as defined in the first aspect or a pharmaceutically acceptable salt thereof in inhalable form;
(c) a pharmaceutical product comprising a compound as defined in the first aspect in inhalable form in association with an inhalation device; and
(d) an inhalation device containing a compound as defined in the first aspect or a pharmaceutically acceptable salt thereof in inhalable form.

Dosages of compounds as defined in the first aspect or a pharmaceutically acceptable salt thereof employed in practicing the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of and their pharmaceutically acceptable salts, hereinafter referred to alternatively as "agents of the invention", are useful as pharmaceuticals. In particular, the compounds are suitable IP receptor agonist and may be tested in the following assays.

Activity of compounds at the IP receptor (IP receptor) is assessed by measuring cAMP accumulation in CHO cells stably expressing the IP receptor (CHO-IP) using the PerkinElmer AlphaScreen assay. This technology measures the endogenous production of cAMP, in a non-radioactive luminescence proximity homogenous assay. A biological reaction occurs between streptavidin coated donor beads, biotinylated cAMP and anti-cAMP acceptor beads, bringing the donor and acceptor beads close enough together so that upon excitation a fluorescence signal is produced. On production of endogenous cAMP, competition between the biotinylated cAMP and cellular-derived cAMP causes a reduction in the fluorescent signal. The reduction in signal is proportional to the amount of cAMP being produced, thus it is possible to quantify the amount of cAMP being produced on stimulation with agonist.

Test and reference compounds are prepared at 100×[final] in 100% DMSO, and diluted 1:3 using a Biomek Fx (Beckman Coulter). This is followed by an intermediate dilution to give 5×[final] in assay buffer (HBSS containing 5 mM HEPES, 0.1% (w/v) BSA). 5 µL of 5×[final] test compounds, reference compounds and buffer/DMSO control are then transferred to a 384-well white OptiPlate, containing 20 µL CHO-IP cell suspension (15,000 cells/well, prepared from frozen), and plate is incubated at room temperature for 1 hour. A cAMP standard curve is constructed for each experiment (concentration range of 10000 nM to 0.001 nM, in assay buffer) and 25 µL of each concentration added to the last two columns of the assay plate. The incubation is terminated by the addition of lysis buffer (dH$_2$O; 0.3% (v v$^{-1}$) Tween-20) containing 20 units mL$^{-1}$ streptavidin coated donor beads and biotinylated cAMP (pre-incubated for 30 minutes) and 20 units mL$^{-1}$ anti-cAMP acceptor beads, which are added to the lysis buffer just before addition to the assay plate. The assay plate is then incubated at room temperature in the dark, for 60 minutes with gentle shaking, and read on the Envision plate reader (Perkin Elmer).

The raw data of the reference compounds, test compounds and controls are converted into cAMP concentrations, using the cAMP standard curve, in GraphPadPrism (GraphPad Software Inc). EC$_{50}$ as well as maximal values of the agonist curves are determined using a 4-parameter logistic equation. The % maximum response values of all test compounds are determined using the top of the treprostinil concentration-response curve.

Compounds of the Examples, herein below, generally have EC$_{50}$ values in the data measurements described above below 5 µM. Table 1 provides a list of representative compounds with their EC$_{50}$ value.

TABLE 1

| Example | EC$_{50}$ (µM) |
|---|---|
| 1 | 0.0017 |
| 1.1 | 0.0575 |
| 1.2 | 0.0018 |
| 1.3 | 0.283 |
| 1.4 | 0.0183 |
| 1.5 | 0.0069 |
| 2.1 | 0.0071 |
| 2.2 | 0.0174 |
| 3 | 0.325 |
| 4.1 | 0.415 |
| 4.2 | 0.0797 |
| 5 | 0.0007 |
| 6 | 0.0018 |
| 7 | 0.32 |
| 8 | 1.25 |
| 9 | 0.0003 |
| 10 | 0.0005 |
| 10.1 | 0.0024 |
| 10.2 | 0.0056 |
| 10.3 | 0.0068 |

TABLE 1-continued

| Example | EC$_{50}$ (µM) |
|---|---|
| 10.4 | 0.0606 |
| 10.5 | 0.0044 |
| 10.6 | 0.0061 |
| 10.7 | 0.0371 |
| 10.8 | 0.0025 |
| 11 | 0.0016 |
| 12 | 0.66 |
| 13 | 0.0024 |
| 14 | 0.0042 |
| 15 | 0.0036 |
| 16 | 0.0030 |
| 17 | 0.0005 |

Preparation of Final Compounds
General Conditions:

Mass spectra were run on LCMS systems using electrospray ionization. These were either Agilent 1100 HPLC/Micromass Platform Mass Spectrometer combinations or Waters Acquity UPLC with SQD Mass Spectrometer. [M+H]$^+$ refers to mono-isotopic molecular weights.

NMR spectra were run on open access Bruker AVANCE 400 NMR spectrometers using ICON-NMR. Spectra were measured at 298K and were referenced using the solvent peak.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings

ABBREVIATIONS

AcOH acetic acid
br broad
BuOH butanol
conc. concentrated
d doublet
DCM dichloromethane
DCE 1,2-dichloroethane
DEAD diethyl azodicarboxylate
DIPEA diisopropylethylamine
DMF N,N-dimethylformamide
DMSO dimethylsulfoxide
Et$_2$O diethyl ether
EtOAc ethyl acetate
EtOH ethanol
h hour(s)
HATU O-(7-azabenzotriazol-1-yl)-N,N,N,N-tetramethyluronium hexafluorophosphate
HPLC high pressure liquid chromatography
KOtBu potassium tert-butoxide
LCMS liquid chromatography and mass spectrometry
MeOH methanol
MeCN acetonitrile
MS mass spectrometry
m multiplet
min minutes
ml milliliter(s)
m/z mass to charge ratio
NBS N-bromosuccinimide
NMR nuclear magnetic resonance
PdCl$_2$(dppf)-CH$_2$Cl$_2$-adduct [1,1-bis(diphenylphosphino)ferrocene]dichloropalladium (II)dichloromethane
Pd(PPh$_3$)$_2$Cl$_2$ bis(triphenylphosphine)palladium(II)dichloride
ppm parts per million
PS polymer supported
Rt retention time
RT room temperature
s singlet
sat. saturated
SCX-2 strong cation exchange (e.g. Isolute® SCX-2 columns from Biotage)
t triplet
tBuOH tert-butanol
TBME methyl-tert-butyl ether
TEA triethylamine
THF tetrahydrofuran Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical LCMS conditions are as follows:
Method 2 minLC_v003
Column Waters BEH C18 50×2.1 mm, 1.7.
Column Temperature 50° C.
Eluents A: H$_2$O, B: acetonitrile, both containing 0.1% TFA
Flow Rate 0.8 ml/min
Gradient 0.20 min 5% B; 5% to 95% B in 1.30 min, 0.25 min 95% B
2 minLowpH
Column: Waters Acquity CSH 1.7 µm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.3 min 5-98% B, 1.3-1.55 min 98% B, 1.55-1.6 min 98-5% B
2 minLowpHv01
Column: Waters Acquity CSH 1.7 µm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.55 min 5-98% B, 1.55-1.75 min 98% B, 1.75-1.8 min 98-5% B
2 minLowpH50v01
Column: Waters Acquity CSH 1.7 µm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 50% B, 0.2-1.55 min 50-98% B, 1.55-1.75 min 98% B, 1.75-1.8 min 98-50% B 10 minLowpH
Column: Waters Acquity CSH 1.7 µm, 2.1×100 mm
Temperature: 50° C.
Mobile Phase: A: Water+0.1% Formic Acid B: Acetonitrile+ 0.1% Formic Acid
Flow rate: 0.7 mL/min
Gradient: 0.0 min 2% B, 0.5-8.0 min 2-98% B, 8.0-9.0 min 98% B, 9.0-9.1 min 98-2% B
Example compounds of the present invention include
Preparation of Final Compounds

EXAMPLE 1

7-(6-Cyclopropyl-2,3-di-p-tolyl-5H-pyrrolo[2,3-b]pyrazin-5-yl)heptanoic acid

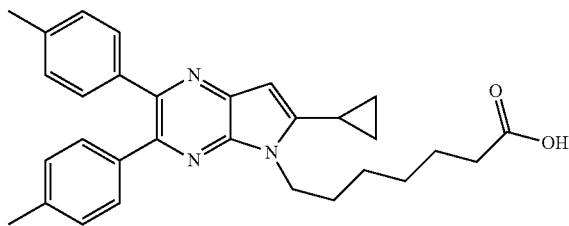 [SMILES: Cc1ccc(-c2nc3cc(C4CC4)n(CCCCCCC(=O)O)c3nc2-c2ccc(C)cc2)cc1]

Step 1: 6-Chloro-5-iodopyrazin-2-amine

A solution of 6-chloropyrazin-2-amine (10.0 g, 77 mmol) in DMSO (100 ml) was treated with 1-iodopyrrolidine-2,5-dione (20.84 g, 93 mmol). The reaction mixture was stirred at RT for 2 days and then added to water (800 ml). The pH was adjusted to pH 8-9 using a sat. NaHCO$_3$ solution and the resulting suspension was filtered, washing with water (×3) and dried under vacuum to afford the titled compound as an orange solid;
LC-MS Rt=0.83 mins; [MeCN+H]$^+$ 296.0, Method 2 min-LowpH.

Step 2: 5,6-Di-p-p-tolylpyrazin-2-amine

A solution of 6-chloro-5-iodopyrazin-2-amine (step 1) (13.74 g, 53.8 mmol) in dioxane (300 ml) was degassed with N$_2$ and treated with p-tolylboronic acid (17.55 g, 129 mmol), K$_2$CO$_3$ (22.30 g, 161 mmol) and PdCl$_2$(dppf)-CH$_2$Cl$_2$-adduct (4.39 g, 5.38 mmol). The orange suspension was stirred at 110° C. for 2 days. After cooling to room temperature the reaction mixture was concentrated under reduced pressure. The crude mixture was absorbed onto silica and purification by chromatography eluting with 0-60% EtOAc in iso-hexane afforded the titled compound as a beige coloured solid;
LC-MS Rt=1.09 mins; [M+H]$^+$ 277.3, Method 2 min-LowpH.

Step 3: 3-Bromo-5,6-di-p-tolylpyrazin-2-amine

A solution of 5,6-di-p-tolylpyrazin-2-amine (step 2) (4.94 g, 17.94 mmol) in DMSO (40 ml) was treated with N-bromosuccinimide (3.19 g, 17.94 mmol). The reaction mixture was stirred at room temperature for 2 hours to give a beige coloured suspension. The suspension was diluted with water (700 ml) and the pH was adjusted to pH 8-9 using a sat. NaHCO$_3$ solution. The suspension was filtered, washed with water (×3) and dried under vacuum to afford the titled compound as a beige coloured solid;
LC-MS Rt=1.39 mins; [M+H]$^+$ 356.3, Method 2 min-LowpH.

Step 4: 3-(Cyclopropylethynyl)-5,6-di-p-tolylpyrazin-2-amine

A solution of 3-bromo-5,6-di-p-tolylpyrazin-2-amine (step 3) (440 mg, 1.24 mmol) in dioxane (5 ml) was degassed with N$_2$ and treated with triethylamine (1.558 ml, 11.18 mmol), ethynylcyclopropane (0.210 ml, 2.484 mmol), copper (I) iodide (71.0 mg, 0.373 mmol) and PdCl$_2$(dppf)-CH$_2$Cl$_2$-adduct (101 mg, 0.124 mmol). After stirring at room temperature for 16 hours, the reaction mixture was concentrated under reduced pressure and dry loaded onto silica using DCM (10 ml). Purification of the crude product by chromatography on silica eluting with 0-20% EtOAc in iso-hexane afforded the titled compound as a beige coloured solid;
LC-MS Rt=1.28 mins; [M+H]$^+$ 340.5, Method 2 min-LowpH.

Step 5: 6-Cyclopropyl-2,3-di-p-tolyl-5H-pyrrolo[2,3-b]pyrazine 3-(Cyclopropylethynyl)-5,6-di-p-tolylpyrazin-2-amine (step 4)(279 mg, 0.822 mmol) in tert-BuOH (10 ml) was treated with potassium tert-butoxide (184 mg, 1.644 mmol) and heated at reflux for 6 hours. The mixture was diluted with water and extracted with DCM (×3). The combined organic extracts were concentrated under reduced pressure and purification of the crude product by chromatography on silica eluting with 0-20% EtOAc in iso-hexane afforded the titled compound as a beige coloured solid;
LC-MS Rt=1.20 mins; [M+H]$^+$ 340.5, Method 2 min-LowpH.

Step 6: Ethyl 7-(6-cyclopropyl-2,3-di-p-tolyl-5H-pyrrolo[2,3-b]pyrazin-5-yl)heptanoate 6-Cyclopropyl-2,3-di-p-p-tolyl-5H-pyrrolo[2,3-b]pyrazine (step 5) (189 mg, 0.557 mmol) in anhydrous DMF (3 ml) degassed with N$_2$ was treated with NaH (60% in mineral oil) (24.50 mg, 0.612 mmol). After stirring at RT for 30 minutes, ethyl 7-bromoheptanoate (0.119 ml, 0.612 mmol) was added and stirring continued for 2 hours. The mixture was diluted with water (50 ml) and the pH was adjusted to pH 1 using 2M HCl. The resulting mixture was extracted with DCM (×3) and the combined organic extracts were concentrated under reduced pressure. Purification of the crude product by chromatography on silica eluting with 0-10% EtOAc in iso-hexane afforded the titled compound as a yellow oil;
Rt 1.47 mins MS m/z 496.5 [M+H]$^+$; Method 2 min-LC_v003
1H NMR (400 MHz, d-DMSO) δ 7.27-7.19 (4H, m), 7.12-7.06 (4H, m), 6.31 (1H, s), 4.39 (2H, t), 4.02 (2H, m), 2.30 (3H, s), 2.30 (3H, s), 2.21 (3H, m), 1.84 (2H, m), 1.49 (2H, m), 1.38-1.27 (4H, br m), 1.17-1.09 (5H, br m), 0.91-0.85 (2H, m).

Step 7: 7-(6-Cyclopropyl-2,3-di-p-tolyl-5H-pyrrolo[2,3-b]pyrazin-5-yl)heptanoic acid Ethyl 7-(6-cyclopropyl-2,3-di-p-tolyl-5H-pyrrolo[2,3-b]pyrazin-5-yl)heptanoate (Step 6) (230 mg, 0.464 mmol) in EtOH (4 ml) was treated with 2M NaOH (0.696 ml, 1.392 mmol) and stirred at room temperature for 16 hours. The reaction mixture was added to water (50 ml) and the pH was adjusted to pH 1 by addition of 2M HCl. The resulting suspension was filtered, washed with water (×3) and dried under vacuum. The resultant residue was dissolved in EtOH (minimal) and excess water added. The resultant aqueous was then extracted with DCM (×3), and the organic solvent removed under reduced pressure. The resultant residue was then taken in diethyl ether, sonicated and the solvent removed under reduced pressure. Further diethyl ether was added, sonicated and the solvent removed under reduced pressure. The resultant residue was dissolved in EtOAc (minimal) and excess iso-hexane was added. The resultant suspension was filtered, the filter cake washed with iso-hexane (×4) and dried to afford the titled compound as a pale yellow solid.

LC-MS Rt=1.32 mins; [M+H]+ 468.6, Method 2 min-LowpH.

$^1$H NMR (400 MHz, DMSO-d6) δ 11.97 (1H, br s), 7.27-7.19 (4H, m), 7.14-7.06 (4H, m), 6.32 (1H, s), 4.40 (2H, t), 2.30 (3H, s), 2.30 (3H, s), 2.20 (1H, m), 2.16 (2H, t), 1.85 (2H, m), 1.48 (2H, m), 1.38-1.29 (4H, br m), 1.14 (2H, m), 0.89 (2H, m)

The compounds of the following tabulated Examples (Table 1) were prepared by a similar method to that of Example 1 from by replacing ethynylcyclopropane (step 4) with the appropriate commercially available alkynes. The acids were prepared analogously to Example 1 steps 1-7 and the esters were prepared analogously to steps 1-6

TABLE 1

| Ex. | Structure | Name | [M + H]+/NMR |
|---|---|---|---|
| 1.1 | 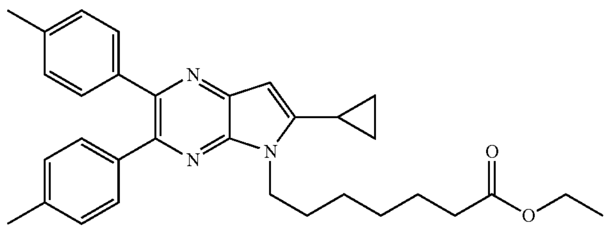 [SMILES: CCOC(=O)CCCCCCn1c(C2CC2)cc2nc(-c3ccc(C)cc3)c(-c3ccc(C)cc3)nc21] | Ethyl 7-(6-cyclopropyl-2,3-di-p-tolyl-5H-pyrrolo[2,3-b]pyrazin-5-yl)heptanoate | LCMS: Rt 1.47 mins MS m/z 496.5 [M + H]+: Method 2minLowpH1H 1H NMR(400 MHz, d-DMSO) δ 7.27-7.19 (4H, m), 7.12-7.06 (4H, m), 6.31 (1H, s), 4.39 (2H, t), 4.02 (2H, m), 2.30 (3H, s), 2.30 (3H, s), 2.21 (3H, m), 1.84 (2H, m), 1.49 (2H, m), 1.38-1.27 (4H, br m), 1.17-1.09 (5H, br m), 0.91-0.85 (2H, m). |
| 1.2 | 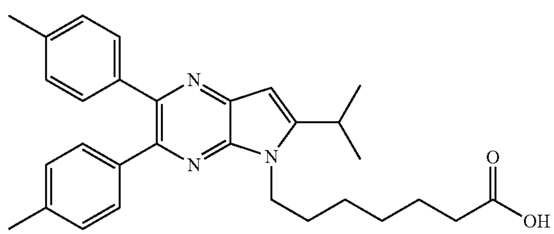 [SMILES: Cc1ccc(-c2nc3cc(C(C)C)n(CCCCCCC(=O)O)c3nc2-c2ccc(C)cc2)cc1] | 7-(6-Isopropyl-2,3-di-p-tolyl-pyrrolo[2,3-b]pyrazin-5-yl)-heptanoic acid | LC-MS Rt 1.28 mins MS m/z 470.5 [M + H]+; Method 2minLC_v003 1H NMR (400MHz, d-DMSO) δ 11.94 (1H, br s), 7.24 (4H, m), 7.11 (4H, m), 6.51 (1H, s), 4.28 (2H, t), 3.27 (1H, br m), 2.30 (3H, s), 2.30 (3H, s), 2.16 (2H, t), 1.79 (2H, br m), 1.47 (2H, br m), 1.37 (3H, d), 1.35 (3H, d), 1.32 (4H, br m) |
| 1.3 | 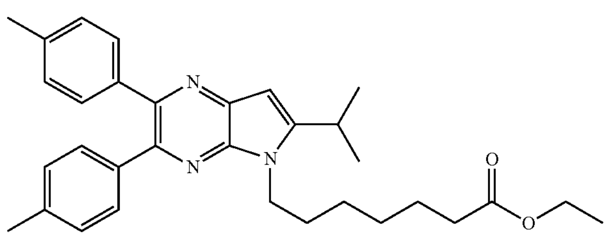 [SMILES: CCOC(=O)CCCCCCn1c(C(C)C)cc2nc(-c3ccc(C)cc3)c(-c3ccc(C)cc3)nc21] | Ethyl 7-(6-iso propyl-2,3-di-p-tolyl-5H-pyrrolo[2,3-b]pyrazin-5-yl) heptano ate | LC-MS Rt 1.46 mins MS m/z 497.8/499.3 [M + H]+; Method 2minLC_v003 1H NMR (400 MHz, d-DMSO) δ 7.24 (4H, m), 7.11 (4H, m), 6.51 (1H, s), 4.28 (2H, t), 4.02 (2H, q), 3.28 (1H, br m), 2.30 (3H, s), 2.30 (3H, s), 2.22 (2H, t), 1.79 (2H, br m), 1.49 (2H, br m), 1.37 (3H, d), 1.36 (3H, s), 1.34-1.28 (4H, br m), 1.15 (3H, t). |

EXAMPLE 1.4

7-(2,3-Di-p-tolyl-pyrrolo[2,3-b]pyrazin-5-yl)-heptanoic acid ethyl ester

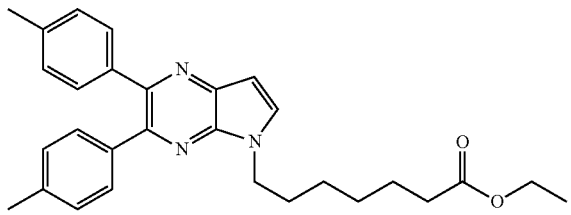 [SMILES: CCOC(=O)CCCCCCn1ccc2nc(-c3ccc(C)cc3)c(-c3ccc(C)cc3)nc21]

The titled compound was prepared from 2,3-di-p-tolyl-5H-pyrrolo[2,3-b]pyrazine (Intermediate A) analogously to ethyl 7-(6-cyclopropyl-2,3-di-p-tolyldi-p-tolyl-5H-pyrrolo[2,3-b]pyrazin-5-yl)heptanoate (Example 1 step 6);

LC-MS Rt=1.44 mins; [M+H]$^+$ 456.4, Method 2 min-LC_v003.

$^1$H NMR (400 MHz, d-DMSO) δ 7.99 (1H, m), 7.26 (4H, m), 7.12 (4H, m), 6.69 (1H, d), 4.29 (2H, t), 4.01 (2H, q), 2.31 (3H, s), 2.31 (3H, s), 2.22 (2H, t), 1.85 (2H, br m), 1.49 (2H, br m), 1.36-1.22 (4H, br m), 1.15 (3H, t).

EXAMPLE 1.5

7-(2,3-Di-p-tolyl-pyrrolo[2,3-b]pyrazin-5-yl)-heptanoic acid

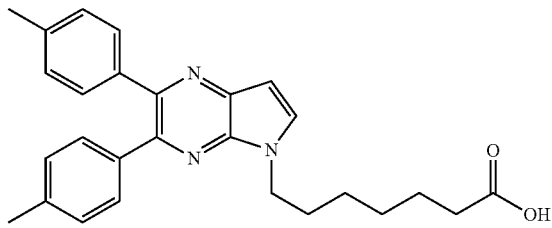 [SMILES: Cc1ccc(-c2nc3ccn(CCCCCCC(=O)O)c3nc2-c2ccc(C)cc2)cc1]

The titled compound was prepared from 7-(2,3-di-p-tolyl-pyrrolo[2,3-b]pyrazin-5-yl)-heptanoic acid ethyl ester (Intermediate B) analogously to 7-(6-cyclopropyl-2,3-di-p-tolyldi-p-tolyl-5H-pyrrolo[2,3-b]pyrazin-5-yl)heptanoic acid (Example 1 step 7);

LC-MS Rt=1.28 mins; [M+H]$^+$ 429.4, Method 2 min-LC_v003.

1H NMR (400 MHz, d-DMSO) δ 11.97 (1H, br s), 7.99 (1H, d), 7.30-7.22 (4H, m), 7.15-7.08 (4H, m), 6.69 (1H, d), 4.30 (2H, t), 2.31 (3H, s), 2.31 (3H, s), 2.16 (2H, t), 1.86 (2H, m), 1.47 (2H, m), 1.36-1.22 (4H, br m)

EXAMPLE 2.1

7-(7-Formyl-2,3di-p-tolyl-5H-pyrrolo[2,3-b]pyrazin-5-yl)heptanoic acid

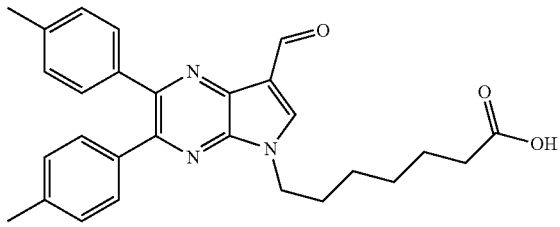 [SMILES: Cc1ccc(-c2nc3c(C=O)cn(CCCCCCC(=O)O)c3nc2-c2ccc(C)cc2)cc1]

The titled compound was prepared from ethyl 7-(7-formyl-2,3di-p-tolyl-5H-pyrrolo[2,3-b]pyrazin-5-yl)heptanoate (Intermediate C) analgously to 7-(6-cyclopropyl-2,3-di-p-tolyl-5H-pyrrolo[2,3-b]pyrazin-5-yl)heptanoic acid (Example 1 step 7);

LC-MS Rt=1.22 mins; [M+H]$^+$ 456.5, Method 2 min-LowpH.

$^1$H NMR (400 MHz, DMSO-d6) δ 11.96 (1H, s), 10.12 (1H, s), 8.84 (1H, s), 7.32-7.27 (4H, m), 7.17-7.13 (4H, m), 4.39 (2H, t), 2.32 (3H, s), 2.31 (3H, s), 2.17 (2H, t), 1.92 (2H, m), 1.48 (2H, m), 1.40-1.23 (4H, br m)

EXAMPLE 2.2

7-(7-(Hydroxymethyl)-2,3-di-p-tolyl-5H-pyrrolo[2,3-b]pyrazin-5-yl)heptanoic acid

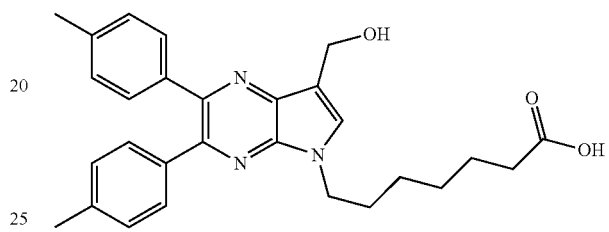

7-(7-Formyl-2,3-di-p-tolyl-5H-pyrrolo[2,3-b]pyrazin-5-yl)heptanoic acid (Example 2.1) (42 mg, 0.092 mmol) in EtOH (1 ml) was degassed with N$_2$ and treated with sodium borohydride (5.23 mg, 0.138 mmol). After stirring at RT for 16 hours, the mixture was added to water (30 ml) and the pH was adjusted to pH 1 using 2M HCl. The aqueous portion was extracted with DCM (×3) and the combined extracts were concentrated under reduced pressure. The crude product was triturated with EtOAc/iso-hexane to afford the titled compound as an orange solid;

LC-MS Rt=1.18 mins; [M+H]$^+$ 458.6, Method 2 min-LowpH.

$^1$H NMR (400 MHz, DMSO-d6) δ 11.83 (1H, br s), 7.89 (1H, s), 7.29-7.21 (4H, br m), 7.15-7.09 (4H, m), 4.97 (1H, br m), 4.73 (2H, m), 4.27 (2H, m), 2.31 (3H, s), 2.31 (3H, s), 2.14 (2H, m), 1.84 (2H, m), 1.47 (2H, m), 1.37-1.22 (4H, br m)

EXAMPLE 3

Ethyl 7-(7-(hydroxymethyl)-2,3-di-p-tolyl-5H-pyrrolo[2,3-b]pyrazin-5-yl)heptanoate

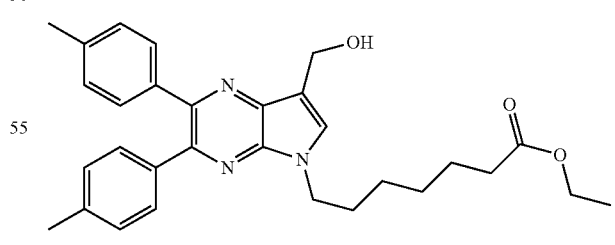

Ethyl 7-(7-Formyl-2,3-di-p-tolyl-5H-pyrrolo[2,3-b]pyrazin-5-yl)heptanoate (Intermediate C) (47 mg, 0.097 mmol) in EtOH (2 ml) was degassed with N$_2$ treated with sodium borohydride (5.52 mg, 0.146 mmol) was added. After stirring at RT for 3 hours, the mixture was diluted with water (30 ml) and the pH was adjusted to pH 1 using 2M HCl. The aqueous portion was extracted with DCM (×3) and the combined extracts were concentrated under reduced pressure. Purification of the crude product by chromatography on silica eluting with 0-40% EtOAc in iso-hexane afforded the titled compound as an orange oil;

LC-MS Rt=1.32 mins; [M+H]⁺ 486.6, Method 2 min-LowpH.

¹H NMR (400 MHz, DMSO-d6) δ 7.89 (1H, s), 7.29-7.23 (4H, m), 7.14-7.09 (4H, m), 4.95 (1H, t), 4.72 (2H, d), 4.27 (2H, t), 4.02 (2H, m), 2.31 (3H, s), 2.31 (3H, s), 2.23 (2H, t), 1.84 (2H, m), 1.49 (2H, m), 1.37-1.22 (4H, br m), 1.51 (3H, t).

EXAMPLE 4.1

Ethyl 7-(7-((isopropylamino)methyl)-2,3-di-p-tolyl-5H-pyrrolo[2,3-b]pyrazin-5-yl)heptanoate

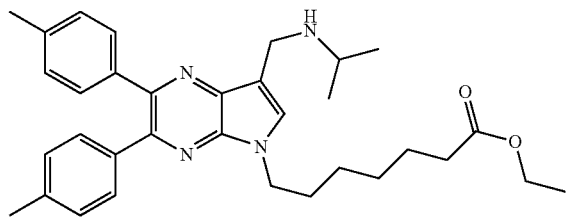 [SMILES: CCOC(=O)CCCCCCn1cc(CNC(C)C)c2nc(-c3ccc(C)cc3)c(-c3ccc(C)cc3)nc21]

Ethyl 7-(7-formyl-2,3-di-p-tolyl-5H-pyrrolo[2,3-b]pyrazin-5-yl)heptanoate (Intermediate C)(50 mg, 0.103 mmol) in DCE (1 ml) was treated with iso-propylamine (0.027 ml, 0.310 mmol) and stirred at RT for 30 minutes. Sodium triacetoxyborohydride (65.7 mg, 0.310 mmol) was added and stirring continued at RT for 16 hours. The mixture was extracted with DCM (30 ml) and the organic extract was washed with water (×2) and concentrated under reduced pressure to afford the titled compound as an orange oil;

LC-MS Rt=1.06 mins; [M+H]⁺ 527.7, Method 2 min-LowpH.

¹H NMR (400 MHz, DMSO-d6): δ 8.61 (1H, br m), 8.12 (1H, s), 7.30-7.25 (4H, m), 7.16-7.11 (4H, m), 4.35-4.28 (4H, m), 4.02 (2H, m), 2.31 (3H, s), 2.31 (3H, s), 2.26-2.20 (3H, m), 1.86 (2H, m), 1.49 (2H, m), 1.36-1.23 (10H, br m), 1.15 (3H, t).

EXAMPLE 4.2

7-(7-((Isopropylamino)methyl)-2,3-di-p-tolyl-5H-pyrrolo[2,3-b]pyrazin-5-yl)heptanoic acid

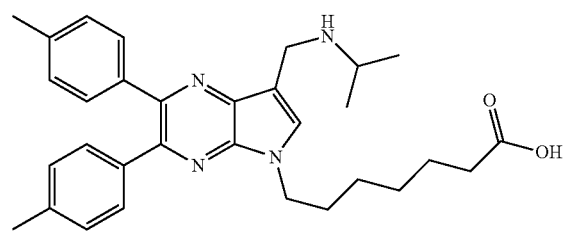 [SMILES: Cc1ccc(-c2nc3c(CNC(C)C)cn(CCCCCCC(=O)O)c3nc2-c2ccc(C)cc2)cc1]

Ethyl 7-(7-((isopropylamino)methyl)-2,3-di-p-tolyldi-p-tolyl-5H-pyrrolo[2,3-b]pyrazin-5-yl)heptanoate (Example 4.1) (53 mg, 0.101 mmol) in EtOH (1 ml) was treated with 2M NaOH (0.151 ml, 0.302 mmol) and stirred at RT for 16 hours. The solvent was removed under reduced pressure and the crude product was dissolved in water and the pH was adjusted to pH 1 using 2M HCl. The mixture was extracted with DCM (×3) and the combined organic extracts were concentrated under reduced pressure to afford an orange solid. The solid was suspended in diethyl ether, sonicated and then filtered, rinsing the filter-cake with diethyl ether (×3). The resultant solid was dried under atmosphere to afford the titled compound as an orange solid.

LC-MS Rt=0.95 mins; [M+H]⁺ 499.7, Method 2 min-LowpH.

¹H NMR (400 MHz, DMSO-d6) δ 11.95 (1H, br s), 8.77 (1H, br m), 8.16 (1H, s), 7.31-7.26 (4H, m), 7.17-7.12 (4H, m), 4.39-4.31 (4H, m), 3.39 (1H, m), 2.32 (3H, s), 2.32 (3H, s), 2.17 (2H, t), 1.87 (2H, m), 1.47 (2H, m), 1.37-1.25 (10H, br m)

EXAMPLE 5

7-(6-Methoxy-2,3-di-p-tolyl-pyrrolo[2,3-b]pyrazin-5-yl)-heptanoic acid

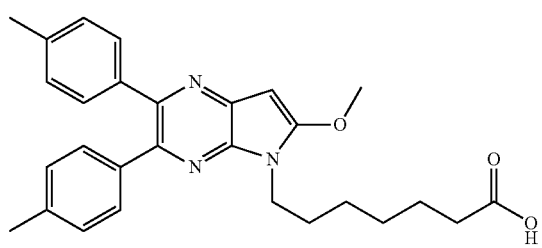 [SMILES: COc1cc2nc(-c3ccc(C)cc3)c(-c3ccc(C)cc3)nc2n1CCCCCCC(=O)O]

Step 1: Ethyl 7-(7-bromo-2,3-di-p-tolyl-5H-pyrrolo [2,3-b]pyrazin-5-yl)heptanoate 7-(2,3-Di-p-tolyl-pyrrolo[2,3-b]pyrazin-5-yl)-heptanoic acid ethyl ester (Intermediate B) (135 mg, 0.296 mmol) in DCM (5 ml) was treated with N-bromosuccinimide (52.7 mg, 0.296 mmol) and the reaction mixture was stirred at room temperature for 16 hours. The mixture was diluted with DCM (50 ml) and washed with water (×2), brine (×1) and the organic solvent was removed under reduced pressure. Purification of the crude product by chromatography on silica using a gradient from 0-10% EtOAc in iso-hexane afforded the titled compound as an orange oil;

LC-MS Rt=1.62 mins; [M+H]⁺ 536.4, Method 2 min-LowpH.

Step 2: 7-(6-Methoxy-2,3-di-p-tolyl-pyrrolo[2,3-b]pyrazin-5-yl)-heptanoic acid

A mixture comprising ethyl 7-(7-bromo-2,3-di-p-tolyl-5H-pyrrolo[2,3-b]pyrazin-5-yl)heptanoate (step 1) (50 mg, 0.094 mmol) in anhydrous MeOH (1 ml) was degassed with N₂ and treated with sodium (10.75 mg, 0.468 mmol). After stirring at room temperature for 30 minutes, the mixture was heated to 120° C. using microwave radiation for 1 hour. The mixture was diluted with water (20 ml) and the pH was adjusted to pH1 using 2M HCl. The aqueous was extracted with DCM (×3) and the combined organic extracts were concentrated under reduced pressure. Purification of the crude product by chromatography on silica eluting with 0-100% EtOAc in iso-hexane followed by 10% MeOH in EtOAc afforded the titled compound as an orange solid;

LC-MS Rt=1.29 mins; [M+H]⁺ 458.4, Method 2 minLC_v003

¹H NMR (400 MHz, DMSO-d6) δ 11.96 (1H, br s), 7.22 (4H, m), 7.09 (4H, m), 5.95 (1H, s), 4.12 (2H, m), 4.10 (3H, s), 2.29 (3H, s), 2.29 (3H, s), 2.15 (2H, t), 1.75 (2H, br m), 1.46 (2H, br m), 1.35-1.23 (4H, br m)

EXAMPLE 6

Ethyl 7-(2,3-di-p-tolyl-6,7-dihydro-5H-pyrrolo[2,3-b]pyrazin-5-yl)heptanoate

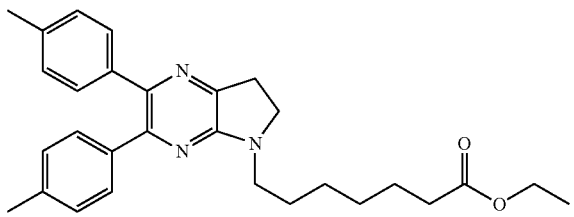 [SMILES: CCOC(=O)CCCCCCN1CCc2nc(-c3ccc(C)cc3)c(-c3ccc(C)cc3)nc21]

7-(2,3-Di-p-tolyl-pyrrolo[2,3-b]pyrazin-5-yl)-heptanoic acid ethyl ester (Intermediate B) (35 mg, 0.077 mmol) in dry EtOH (1 ml) under nitrogen at RT was treated with ammonium formate (24.22 mg, 0.384 mmol) followed by Pd on carbon (8.18 mg, 7.68 µmol). The resulting black suspension was heated at reflux for 16 hours, overnight. The reaction mixture was cooled to RT and then loaded onto a Celite® (filter material) column. The column was eluted with 1:1 MeOH/DCM and the filtrate concentrated under reduced pressure. The resultant residue was dissolved in DCM (50 ml), washed with water (×2) and the organic solvent removed under reduced pressure. Purification by chromatography on silica eluting with 0-30% EtOAc in iso-hexane afforded the titled compound;

LC-MS Rt 1.36 mins MS m/z 458.4 [M+H]⁺; Method 2 minLC_v003

1H NMR (400 MHz, DMSO-d6) δ 7.15 (2H, d), 7.1-7.05 (4H, m), 7.0 (2H, d), 4.05 (2H, m), 3.65 (2H, m), 3.35 (2H, m), 3.1 (2H, m), 2.3 (3H, s), 2.25 (3H, s), 1.6 (2H, m), 1.5 (2H, m), 1.35-1.2 (6H, m), 1.15 (3H, t).

EXAMPLE 7

5-(2,3-Di-p-tolyl-5H-pyrrolo[2,3-b]pyrazin-6-yl)-pentanoic acid

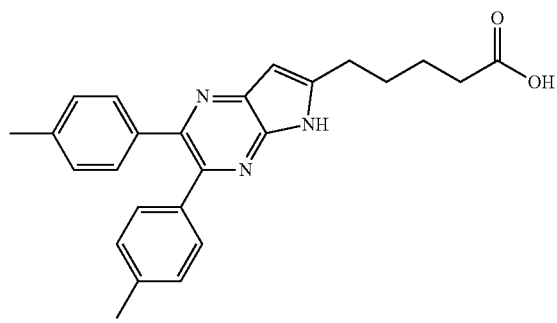 [SMILES: Cc1ccc(-c2nc3cc(CCCCC(=O)O)[nH]c3nc2-c2ccc(C)cc2)cc1]

Step 1: 7-(3-Amino-5,6-di-p-tolylpyrazin-2-yl)hept-6-ynoic acid

3-Bromo-5,6-di-p-tolylpyrazin-2-amine (Example 1, step 3) (200 mg, 0.565 mmol) in anhydrous dioxane (10 ml), degassed with N₂ was treated with triethylamine (0.708 ml, 5.08 mmol), hept-6-ynoic acid (0.179 ml, 1.129 mmol), copper(I) iodide (32.3 mg, 0.169 mmol) and PdCl₂(dppf)-CH₂Cl₂-adduct (46.1 mg, 0.056 mmol). The reaction mixture was stirred at room temperature for 16 hours. The resulting mixture was diluted with DCM (10 ml) and dry loaded onto silica. Purification by chromatography on silica eluting with 0-100% EtOAc in iso-hexane followed by 20% MeOH in EtOAc afforded the titled compound;

LC-MS: Rt 1.25 mins MS m/z 401.3 [M+H]⁺; Method 2 minLC_v003

Step 2: 5-(2,3-Di-p-tolyl-5H-pyrrolo[2,3-b]pyrazin-6-yl)pentanoic acid 7-(3-Amino-5,6-di-p-tolylpyrazin-2-yl)hept-6-ynoic acid (step 1) (137 mg, 0.343 mmol) in tert-BuOH (3 ml) was treated with potassium tert-butoxide (154 mg, 1.372 mmol) and stirred at reflux for 3 hours. The mixture was added to water (50 ml) and extracted with DCM (×3). The organic solvent was removed under reduced pressure and the crude material was dissolved in EtOH (minimal) and excess of water was added. The resulting suspension was sonicated and filtered, rinsing the filter cake with water (×3). Purification of crude product by chromatograpy on silica eluting with 0-1% MeOH in DCM afforded the titled compound; LC-MS Rt 1.10 mins MS m/z 400.2 [M+H]⁺; Method 2 minLC_v003

1H NMR (400 MHz, d-DMSO) δ 12.03 (1H, br s), 11.92 (1H, br s), 7.23 (4H, m), 7.10 (4H, m), 6.41 (1H, m), 2.84 (2H, t), 2.30 (3H, s), 2.30 (3H, s), 2.28 (2H, m), 1.77 (2H, br m), 1.59 (2H, br m)

EXAMPLE 8

2-(5-(2,3-Di-p-tolyl-5H-pyrrolo[2,3-b]pyrazin-6-yl)pentanamido)acetic acid

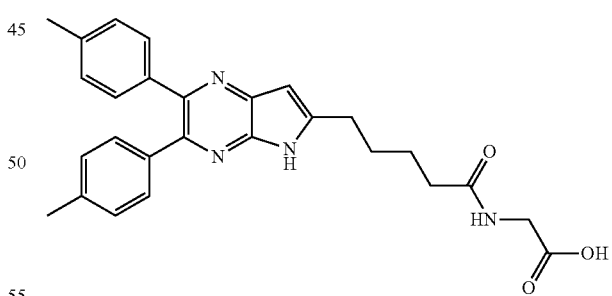

Step 1: Methyl 2-(5-(2,3-di-p-tolyldi-p-tolyl-5H-pyrrolo[2,3-b]pyrazin-6-yl)pentanamido)acetate 5-(2,3-Di-p-tolyl-5H-pyrrolo[2,3-b]pyrazin-6-yl)pentanoic acid (Example 7) (25 mg, 0.063 mmol) in DMF (1 ml) was treated with DIPEA (0.055 ml, 0.313 mmol) and HATU (57.1 mg, 0.150 mmol). After stirring at RT for 15 minutes, the mixture was treated with glycine methyl ester hydrochloride (9.43 mg, 0.075 mmol) and stirred at RT for 2 hours. The resulting mixture was diluted with water and the resultant suspension was sonicated and filtered, rinsing the filter cake with water (×3). Purification of crude product by chromatograpy on silica eluting with 0-50% EtOAc in iso-hexane followed by 10% MeOH in EtOAc afforded the titled compound;

LC-MS Rt 1.10 mins MS m/z 471 [M+H]$^+$; Method 2 minLC_v003

Step 2: 2-(5-(2,3-Di-p-tolyl-5H-pyrrolo[2,3-b]pyrazin-6-yl)pentanamido)acetic acid Methyl 2-(5-(2,3-di-p-tolyldi-p-tolyl-5H-pyrrolo[2,3-b]pyrazin-6-yl)pentanamido)acetate (step 1) (17 mg, 0.036 mmol) in THF (1 ml) and water (0.5 ml) was treated with LiOH. monohydrate (8.12 mg, 0.108 mmol). After stirring at room temperature for 3 hours, the reaction mixture was treated with water (20 ml) and the pH adjusted to pH 2 using 2M HCl. The aqueous portion was extracted with DCM (×3) and the combined organic extracts were concentrated under reduced pressure. Purification by reverse phase (C18) chromatograpy eluting with 0-30% MeCN in water (0.1% TFA) afforded the titled compound;

LC-MS Rt 1.05 mins MS m/z 457.4 [M+H]$^+$; Method 2 minLC_v003

1H NMR (400 MHz, d-DMSO) δ 12.51 (1H, br s), 11.92 (1H, s), 8.16 (1H, m), 7.24 (4H, m), 7.1 (4H, m), 6.41 (1H, m), 3.73 (2H, d), 2.84 (2H, t), 2.30 (3H, s), 2.30 (3H, s), 2.20 (2H, t), 1.76 (2H, br m), 1.59 (2H, br m)

EXAMPLE 9

7-(6-Methyl-2,3-di-p-tolyl-5H-pyrrolo[2,3-b]pyrazin-5-yl)heptanoic acid

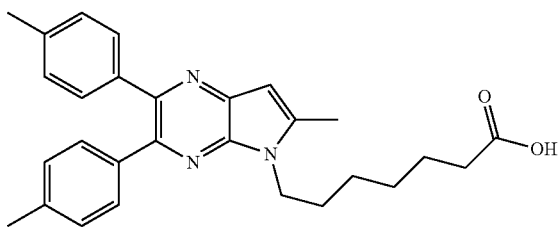 [SMILES: Cc1ccc(-c2nc3cc(C)n(CCCCCCC(=O)O)c3nc2-c2ccc(C)cc2)cc1]

Step 1: 3,5-Dibromo-6-chloropyrazin-2-amine

6-Chloropyrazin-2-amine (100 g, 772 mmol) in MeOH (2000 ml) cooled using a water bath was treated with N-bromosuccinimide (151.2 g, 170 mmol) portionwise over 30 mins, maintaining the reaction temperature between 15-20° C. After stirring for 1.5 hours, the mixture was poured carefully into a stirred vessel of ice-cooled water (4 liters). The resultant suspension was stirred for 2 hours in the ice bath, collected by filtration, rinsing the filter cake with water (800 ml) and dried in a vacuum oven to afford the titled compound;

LC-MS Rt 0.99 mins; Method 2 minLowpH

Step 2: 5-Bromo-6-chloro-3-(3-(trimethylsilyl)prop-1-ynyl)pyrazin-2-amine 3,5-Dibromo-6-chloropyrazin-2-amine (step 1) (400 mg, 1.392 mmol) in dry THF (10 ml) was degassed with nitrogen and treated with trimethyl(prop-2-ynyl)silane (0.218 ml, 1.462 mmol), TEA (0.582 ml, 4.18 mmol), CuI (26.5 mg, 0.139 mmol) and Pd(PPh$_3$)$_2$Cl$_2$ (98 mg, 0.139 mmol). After stirring at room temperature for 2 hours, the reaction mixture was diluted with water (100 ml) and brine and extracted with DCM (×3). The combined organic extracts were concentrated under reduced pressure. Purification of the crude product by chromatography on silica eluting with 0-20% EtOAc in iso-hexane afforded the titled compound;

LC-MS Rt=1.25 mins; [M+H]$^+$ 318/320 Method 2 minLowpH.

Step 3: 2-Bromo-3-chloro-6-methyl-5H-pyrrolo[2,3-b]pyrazine

5-Bromo-6-chloro-3-(3-(trimethylsilyl)prop-1-ynyl)pyrazin-2-amine (step 2) (280 mg, 0.879 mmol) in tert-butanol (4 ml) at RT was treated with KOtBu (217 mg, 1.933 mmol) and heated at 60° C. for 2 hours. The reaction mixture was cooled to room temperature, diluted with water and the pH adjusted to pH 1 using 2M HCl. The aqueous was extracted with DCM (×3) and the organic solvent removed under reduced pressure to afford the titled compound:

LC-MS Rt=0.97 mins; [M+H]$^+$ 246/248: Method 2 minLowpH.

Step 4: 6-Methyl-2,3-di-p-tolyl-5H-pyrrolo[2,3-b]pyrazine

2-Bromo-3-chloro-6-methyl-5H-pyrrolo[2,3-b]pyrazine (step 3) (183 mg, 0.742 mmol) in dioxane (5 ml) was degassed with N$_2$ and treated with p-tolylboronic acid (242 mg, 1.782 mmol), K$_2$CO$_3$ (308 mg, 2.227 mmol) and PdCl$_2$(dppf)-CH$_2$Cl$_2$-adduct (60.6 mg, 0.074 mmol). The reaction mixture was heated at reflux for 3 hours. After cooling to RT, further portions of p-tolyl boronic acid (242 mg, 1.782 mmol) and PdCl$_2$(dppf)-CH$_2$Cl$_2$-adduct (60.6 mg, 0.074 mmol) were added and heating continued at reflux for 2 hours. After cooling to RT, the mixture was diluted with water (50 ml). The resultant suspension was sonicated and filtered, rinsing the filter cake with water (×3). Purification of the crude product by chromatography on silica eluting with 0-30% EtOAc in iso-hexane afforded the titled compound;

LC-MS Rt=1.15 mins; [M+H]$^+$ 314/315 Method 2 minLowpH.

Step 5: 7-(6-Methyl-2,3-di-p-tolyl-5H-pyrrolo[2,3-b]pyrazin-5-yl)heptanoic acid The titled compound was prepared from 6-methyl-2,3-di-p-tolyldi-p-tolyl-5H-pyrrolo[2,3-b]pyrazine (Example 9; Step 4) analogously to 7-(6-cyclopropyl-2,3-di-p-tolyl-5H-pyrrolo[2,3-b]pyrazin-5-yl)heptanoic acid (Example 1 step 6 and step 7);

LC-MS: Rt 1.28 mins MS m/z 442.7/443.4 [M+H]$^+$; Method 2 minLC_v003

$^1$H NMR (400 MHz, DMSO-d6): δ 11.94 (1H, br s), 7.28-7.21 (4H, m), 7.13-7.07 (4H, m), 6.47 (1H, s), 4.25 (2H, t), 2.57 (3H, s), 2.30 (3H, s), 2.30 (3H, s), 2.15 (2H, t), 1.76 (2H, m), 1.46 (2H, m), 1.36-1.25 (4H, br m).

EXAMPLE 10

7-(6-Cyclopropyl-2,3-diphenyl-pyrrolo[2,3-b]pyrazin-5-yl)-heptanoic acid

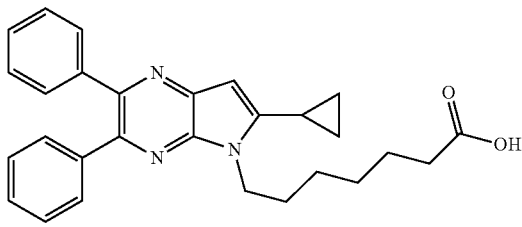 [SMILES: O=C(O)CCCCCCn1c(C2CC2)cc2nc(-c3ccccc3)c(-c3ccccc3)nc21]

Step 1: 7-(6-Cyclopropyl-2,3-diphenyl-pyrrolo[2,3-b]pyrazin-5-yl)-heptanoic acid ethyl ester A mixture comprising 7-(2-bromo-3-chloro-6-cyclopropyl-pyrrolo[2,3-b]pyrazin-5-yl)-heptanoic acid ethyl ester (Intermediate D) (400 mg, 0.933 mmol) in 1,4-dioxane (8 ml) degassed with $N_2$ was treated with phenylboronic acid (120 mg, 0.980 mmol), potassium carbonate (284 mg, 2.052 mmol) and $PdCl_2$(dppf)-$CH_2Cl_2$-adduct (76 mg, 0.093 mmol). The reaction mixture was stirred at 60° C. for 12 hours. After cooling to RT and degassing with $N_2$, phenylboronic acid (171 mg, 1.399 mmol) and $PdCl_2$(dppf)-$CH_2Cl_2$-adduct (76 mg, 0.093 mmol) were added and stirring continued at 110° C. for 24 hours. The mixture was treated with ice-cooled water and the aqueous was extracted with diethyl ether. The organic portion was dried ($Na_2SO_4$) and concentrated under reduced pressure. Purification of the crude product on silica eluting with 5% EtOAc in iso-hexane afforded the titled compound:

HPLC Rt 5.74 mins: MS m/z 428.1

Step 2: 7-(6-Cyclopropyl-2,3-diphenyl-pyrrolo[2,3-b]pyrazin-5-yl)-heptanoic acid 7-(6-Cyclopropyl-2,3-diphenyl-pyrrolo[2,3-b]pyrazin-5-yl)-heptanoic acid ethyl ester (step 1) (250 mg, 0.535 mmol) in THF (6 ml) and water (2 ml) was treated with LiOH.monohydrate (45 mg, 1.069 mmol) and stirred at room temperature for 12 hours followed by heating at 60° C. for 10 hours. The mixture was concentrated under reduced pressure. The residue was dissolved in water and washed with diethyl ether (×1). The aqueous was acidified using citric acid, and extracted with EtOAc. The organic solvent was dried ($Na_2SO_4$) and the solvent was removed under reduced pressure. Purification of the product by chromatography on silica eluting with 1% MeOH in DCM, followed by further purification using preparative HPLC according to the following conditions to afforded the titled compound;

Column: ZORBAX-150*21.2 MM

Mobile phase: A: 10 mmol ammonium acetate in water; B:1:1 MeOH:acetonitrile

Flow rate: 30 ml/min.

| TIME | % B | Flow (ml/min) |
| --- | --- | --- |
| 0.0 | 60.0 | 20.0 |
| 2.0 | 60.0 | 20.0 |
| 10.0 | 90.0 | 20.0 |

LCMS: Rt 1.27 mins MS m/z 440.0 [M+H]$^+$: Method 2 minLowpH

The compounds of the following tabulated Examples (Table 2) were prepared by a similar method to that of Example 10 by replacing phenylboronic acid (steps 1 and 2) with the appropriate commercially available boronic acids.

TABLE 2

| Ex. | Structure | Name | [M + H]$^+$/NMR |
| --- | --- | --- | --- |
| 10.1 | 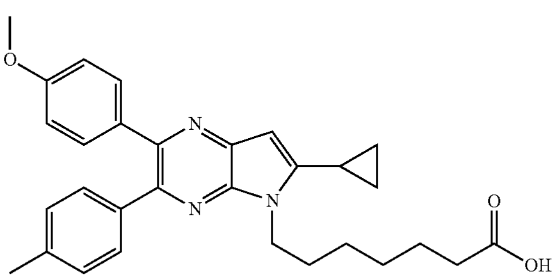 [SMILES: COc1ccc(-c2nc3cc(C4CC4)n(CCCCCCC(=O)O)c3nc2-c2ccc(C)cc2)cc1] | 7-(6-cyclo propyl-2-(4-methoxy phenyl)-3-(p-tolyl)-5H-pyrrolo[2,3-b]pyrazin-5-yl)heptanoic acid | LCMS: Rt 1.28 mins MS m/z 485.4 [M + H]+: Method 2minLowpH |
| 10.2 | 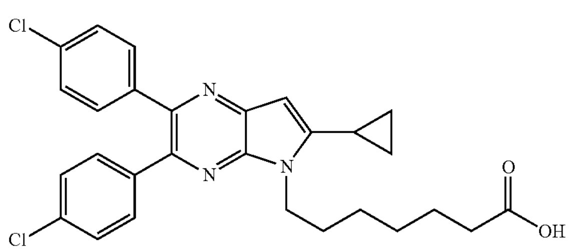 [SMILES: O=C(O)CCCCCCn1c(C2CC2)cc2nc(-c3ccc(Cl)cc3)c(-c3ccc(Cl)cc3)nc21] | 7-(2,3-bis(4-chlorophenyl)-6-cyclo propyl-5H-pyrrolo[2,3-b]pyrazin-5-yl)heptanoic acid | LCMS: Rt 1.42 mins MS m/z 508.3 [M + H]+: Method 2minLowpH |

TABLE 2-continued

| Ex. | Structure | Name | [M + H]+/NMR |
|---|---|---|---|
| 10.3 | 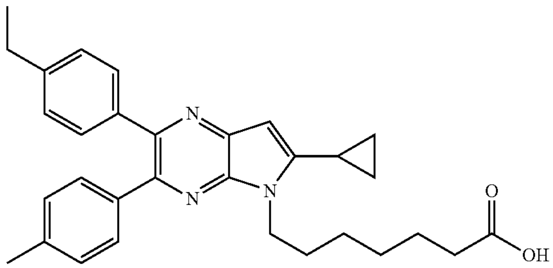 [SMILES: CCc1ccc(-c2nc3cc(C4CC4)n(CCCCCCC(=O)O)c3nc2-c2ccc(C)cc2)cc1] | 7-(6-cyclo propyl-2-(4-ethyl phenyl)-3-(p-tolyl)-5H-pyrrolo[2,3-b]pyraz in-5-yl)hep tanoic acid | LCMS: Rt 1.39 mins MS m/z 483.4 [M + H]+: Method 2minLowpH |
| 10.4 | 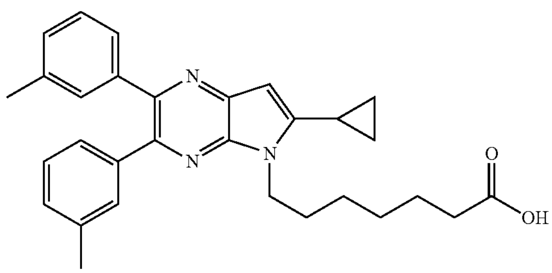 [SMILES: Cc1cccc(-c2nc3cc(C4CC4)n(CCCCCCC(=O)O)c3nc2-c2cccc(C)c2)c1] | 7-(6-cyclo propyl-2,3-di-m-tolyl-5H-pyrrolo [2,3-b]pyrazin-5-yl)hep tanoic acid | LCMS: Rt 1.35 mins MS m/z 469.3 [M + H]+: Method 2minLowpH |
| 10.5 | 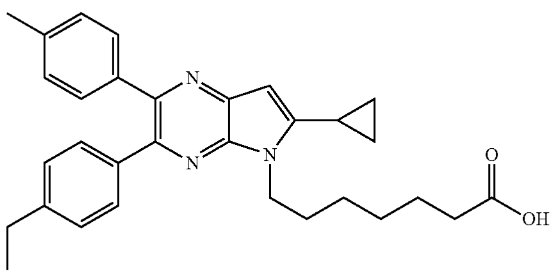 [SMILES: CCc1ccc(-c2nc3c(cc(C4CC4)n3CCCCCCC(=O)O)nc2-c2ccc(C)cc2)cc1] | 7-(6-cyclopropyl-3-(4-ethylphenyl)-2-(p-tolyl)-5H-pyrrolo[2,3-b]pyrazin-5-yl)heptanoic acid | LCMS: Rt 1.36 mins; MS m/z 482.6 [M + H]+; 2minLowpH |
| 10.6 | 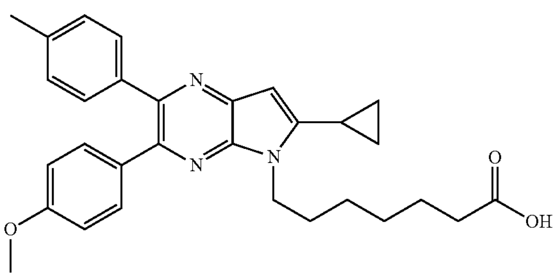 [SMILES: COc1ccc(-c2nc3c(cc(C4CC4)n3CCCCCCC(=O)O)nc2-c2ccc(C)cc2)cc1] | 7-(6-cyclopropyl-3-(4-methoxyphenyl)-2-(p-tolyl)-5H-pyrrolo[2.3-b]pyrazin-5-yl)heptanoic acid | LCMS: Rt 1.25 mins; MS m/z 484.6[M + H]+; 2minLowpH |
| 10.7 | 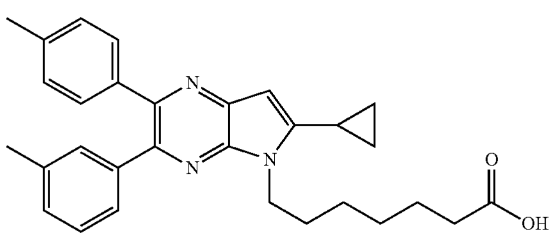 [SMILES: Cc1ccc(-c2nc3cc(C4CC4)n(CCCCCCC(=O)O)c3nc2-c2cccc(C)c2)cc1] | 7-(6-cyclopropyl-3-(m-tolyl)-2-(p-tolyl)-5H-pyrrolo[2,3-b]pyrazin-5-yl)heptanoic acid | LCMS: Rt 1.31 mins; MS m/z 468.6 [M + H]+; 2minLowpH |
| 10.8 | 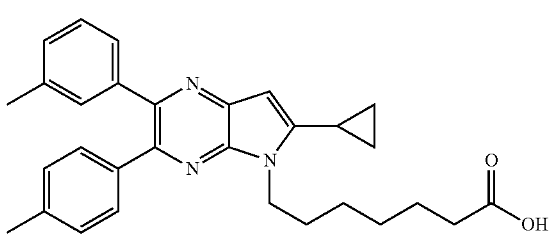 [SMILES: Cc1ccc(-c2nc3c(cc(C4CC4)n3CCCCCCC(=O)O)nc2-c2cccc(C)c2)cc1] | 7-(6-cyclopropyl-2-(m-tolyl)-3-(p-tolyl)-5H-pyrrolo[2,3-b]pyrazin-5-yl)heptanoic acid | LCMS: Rt 1.32 mins; MS m/z 468.6 [M + H]+; 2minLowpH |

EXAMPLE 11

7-(6-(2-Hydroxyethyl)-2,3-di-p-tolyl-5H-pyrrolo[2,3-b]pyrazin-5-yl)heptanoic acid

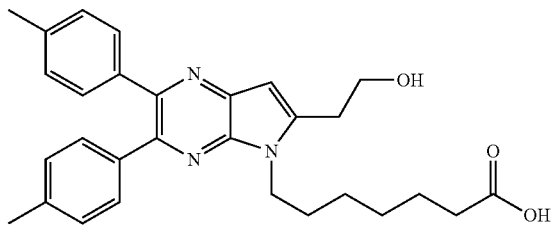 [SMILES: Cc1ccc(-c2nc3cc(CCO)n(CCCCCCC(=O)O)c3nc2-c2ccc(C)cc2)cc1]

Step 1: 4-(3-Amino-5,6-di-p-tolylpyrazin-2-yl)but-3-yn-1-ol

The title compound was prepared analogously to 7-(3-amino-5,6-di-p-tolylpyrazin-2-yl)hept-6-ynoic acid (Ex 7 step 1) by replacing hept-6-ynoic acid with but-3-yn-1-ol;
LCMS: Rt 1.11 mins MS m/z 344 [M+H]+ Method 2 minLowpH

Step 2: 2-(2,3-Di-p-tolyl-5H-pyrrolo[2,3-b]pyrazin-6-yl)ethanol

The title compound was prepared from 4-(3-amino-5,6-di-p-tolylpyrazin-2-yl)but-3-yn-1-ol (step 1) analogously to 5-(2,3-di-p-tolyl-5H-pyrrolo[2,3-b]pyrazin-6-yl)pentanoic acid (Ex 7, step 2);
LCMS: Rt 1.04 mins MS m/z 344 [M+H]+: Method 2 minLowpH

Step 3: 2-(2,3-Dip-tolyl-5H-pyrrolo[2,3-b]pyrazin-6-yl)ethyl acetate 2-(2,3-Di-p-tolyl-5H-pyrrolo[2,3-b]pyrazin-6-yl)ethanol (step 2) (73 mg, 0.213 mmol) in dry THF (2 ml) at RT was treated with DIPEA (0.082 ml, 0.468 mmol) and acetyl chloride (0.018 ml, 0.255 mmol). After stirring for 16 hours at RT, the mixture was added to water (30 ml) and extracted with DCM (×3). The combined organic extracts were passed through a phase separating column and concentrated under reduced pressure. The crude product was purified by chromatography on silica eluting with 0-40% EtOAc/iso-hexane to afford the title compound, 2-(2,3-dip-tolyl-5H-pyrrolo[2,3-b]pyrazin-6-yl)ethyl acetate;
LCMS: Rt 1.15 mins MS m/z 386.6 [M+H]+Method 2 minLowpH
2-(5-Acetyl-2,3-d-ip-tolyl-5H-pyrrolo[2,3-b]pyrazin-6-yl)ethyl acetate was also isolated as a by-product.

Step 4: Ethyl 7-(6-(2-acetoxyethyl)-2,3-di-p-tolyl-5H-pyrrolo[2,3-b]pyrazin-5-yl)heptanoate 2-(2,3-Dip-tolyl-5H-pyrrolo[2,3-b]pyrazin-6-yl)ethyl acetate (step 3) (12 mg, 0.031 mmol) was dissolved in dry DMF (1 ml) at RT and treated with $K_2CO_3$ (12.91 mg, 0.093 mmol) and ethyl 7-bromoheptanoate (0.012 ml, 0.062 mmol). The resulting brown suspension was stirred at RT for 16 hours. The mixture was then heated at 60° C. for 5 hours and after cooling to RT, stirred overnight. The mixture was added to water (30 ml) and extracted with DCM (×3). The combined organic extracts were passed through a phase separating column and concentrated under reduced pressure to afford the title compound;
LCMS: Rt 1.40 mins MS m/z 542.7 [M+H]+; Method 2 minLowpH

Step 5: 7-(6-(2-Hydroxyethyl)-2,3-di-p-tolyl-5H-pyrrolo[2,3-b]pyrazin-5-yl)heptanoic acid Ethyl 7-(6-(2-acetoxyethyl)-2,3-di-p-tolyl-5H-pyrrolo[2,3-b]pyrazin-5-yl)heptanoate (step 4) (17 mg, 0.031 mmol) in EtOH (1 ml) at RT was treated with 2M NaOH (0.047 ml, 0.094 mmol) and stirred at RT for 4 hours. Further 2M NaOH (0.047 ml, 0.094 mmol) was added and the mixture was stirred at RT for 16 hours overnight. Further 2M NaOH (0.047 ml, 0.094 mmol) was added and the orange RM was stirred at RT overnight. The resulting mixture was added to water (30 ml) and the pH was adjusted to pH1 by addition of 2M HCl. The aqueous was extracted with DCM (×4) and the combined extracts were passed through a phase separating column and concentrated under reduced pressure to afford an orange oil. The oil was dissolved in EtOAc and an excess of iso-hexane was added. The resulting suspension was sonicated and removed by filtration. The filtrate was concentrated under reduced pressure and the crude product was dissolved in DCM (minimal) and loaded onto a Si 20 mm×20 mm preparative TLC plate. Using a solvent system of 10% MeOH in DCM (200 ml) the TLC plate was eluted and the appropriate strip of Si on the plate was scrapped off the plate. The Si was suspended in 10% MeOH/DCM and sonicated. The suspension was filtered, rinsing the solid with 10% MeOH/DCM. The filtrate was concentrated under reduced pressure to afford the title compound;
LCMS: Rt 1.16 mins MS m/z 472.1/473.4 [M+H]+Method 2 minLowpH
1H NMR (400 MHz, d-DMSO) δ 11.96 (1H, br s), 7.28-7.20 (4H, br m), 7.14-7.08 (4H, br m), 6.52 (1H, s), 4.91 (1H, br m), 4.29 (2H, m), 3.83 (2H, m), 3.05 (2H, m), 2.30 (3H, s), 2.30 (3H, s), 2.16 (2H, m), 1.81-1.73 (2H, br m), 1.52-1.43 (2H, br m), 1.37-1.27 (4H, br m)

EXAMPLE 12

5-(6-Cyclopropyl-2,3-di-p-tolyl-5H-pyrrolo[2,3-b]pyrazin-5-yl)pentanoic acid

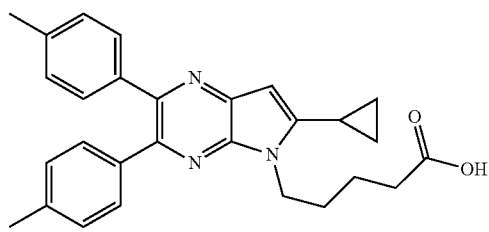 [SMILES: Cc1ccc(-c2nc3cc(C4CC4)n(CCCCC(=O)O)c3nc2-c2ccc(C)cc2)cc1]

The title compound was prepared analogously to Example 1 by replacing ethyl 7-bromoheptanoate (step 6) with ethyl 5-bromopentanoate;
LCMS: Rt 1.42 mins MS m/z 441.5 [M+H]+; Method 2 minLowpHv01
1H NMR (400 MHz, d-DMSO) δ 12.01 (1H, br s), 7.28-7.19 (4H, br m), 7.13-7.07 (4H, br m), 6.32 (1H, s), 4.41 (2H, m), 2.34-2.27 (2H, br m), 2.31 (3H, s), 2.31 (3H, s), 2.23-2.16

(1H, br m), 1.92-1.83 (2H, br m), 1.58-1.49 (2H, br m), 1.16-1.10 (2H, br m), 0.91-0.87 (2H, br m)

EXAMPLE 13

6-(6-Cyclopropyl-2,3-di-p-tolyl-5H-pyrrolo[2,3-b]pyrazin-5-yl)hexanoic acid

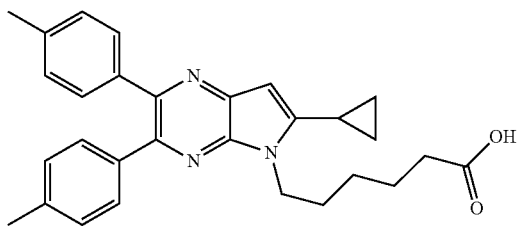 [SMILES: Cc1ccc(-c2nc3cc(C4CC4)n(CCCCCC(=O)O)c3nc2-c2ccc(C)cc2)cc1]

The title compound was prepared analogously to Example 1 by replacing ethyl 7-bromoheptanoate (step 6) with ethyl 6-bromohexanoate;

LCMS: Rt 1.43 mins MS m/z 454.2/455.5 [M+H]+: Method 2 minLowpHv01.

1H NMR (400 MHz, d-DMSO) δ 11.98 (1H, br s), 7.28-7.19 (4H, br m), 7.13-7.07 (4H, br m), 6.32 (1H, s), 4.40 (2H, m), 2.30 (3H, s), 2.30 (3H, s), 2.23-2.17 (3H, br m), 1.90-1.82 (2H, br m), 1.62-1.54 (2H, br m), 1.38-1.29 (2H, br m), 1.16-1.11 (2H, br m), 0.91-0.87 (2H, br m).

EXAMPLE 14

7-(7-(Methoxymethyl)-2,3-di-p-tolyl-5H-pyrrolo[2,3-b]pyrazin-5-yl)heptanoic acid

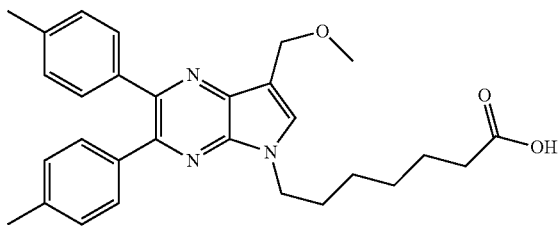 [SMILES: COCc1cn(CCCCCCC(=O)O)c2nc(-c3ccc(C)cc3)c(-c3ccc(C)cc3)nc12]

Ethyl 7-(7-(hydroxymethyl)-2,3-di-p-tolyl-5H-pyrrolo[2,3-b]pyrazin-5-yl)heptanoate (Example 3) (50 mg, 0.103 mmol) in dry DMF (1 ml) under nitrogen was treated with NaH (60% in mineral oil) (4.53 mg, 0.113 mmol) and the resulting mixture was stirred at RT for 15 minutes. Methyl iodide (7.08 μl, 0.113 mmol) was added and stirring continued at RT overnight. The mixture was added to water (30 ml) and the pH was adjusted to pH1 by addition of 2M HCl. The aqueous was extracted with DCM (×3) and the combined organic portions were passed through a phase separating column and concentrated under reduced pressure. The crude product was purified by chromatography on silica eluting with 0-50% EtOAc/iso-hexane. Further purification was carried out by dissolving the product in DCM (minimal) and loading onto a 20 cm×20 cm preparative TLC plate. The plate was run using a solvent system of 67% EtOAc in iso-hexane (300 ml) and the appropriate strip of silica was scrapped off the plate. The Si was suspended in 10% MeOH/DCM and sonicated. The suspension was filtered, rinsing the solid with 10% MeOH/DCM. The filtrate was concentrated under reduced pressure to afford the title compound;

LCMS: Rt 1.43 mins MS m/z 473.8 [M+H]+: Method 2 minLowpHv01

1H NMR (400 MHz, d-DMSO) δ 12.03 (1H, br s), 8.01 (1H, s), 7.29-7.22 (4H, br m), 7.14-7.10 (4H, br m), 4.62 (2H, s), 4.28 (2H, m), 3.31 (3H, s), 2.31 (3H, s), 2.31 (3H, s), 2.14 (2H, m), 1.88-1.82 (2H, br m), 1.49 (2H, br m), 1.36-1.21 (4H, br m)

EXAMPLE 15

7-(6-oxo-2,3-dip-tolyl-6,7-dihydro-5H-pyrrolo[2,3-b]pyrazin-5-yl)heptanoic acid

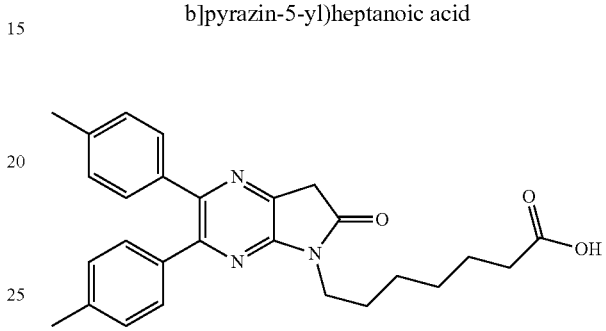

Step 1: 7-(7,7-Dibromo-6-oxo-2,3-di-p-tolyl-6,7-dihydro-5H-pyrrolo[2,3-b]pyrazin-5-yl)heptanoic acid 7-(2,3-Di-p-tolyl-pyrrolo[2,3-b]pyrazin-5-yl)-heptanoic acid (Example 1.5) (90 mg, 0.211 mmol) in tert-butanol (3 ml) and water (0.5 ml) was treated with NBS (112 mg, 0.632 mmol) and the resulting brown mixture was stirred at RT for 18 hours. The mixture was diluted with water (50 ml) and the pH was adjusted to pH 1 using 2M HCl. The aqueous was extracted with DCM (×3), passing the organics through a phase separating column. The organic solvent was removed under reduced pressure to afford the title compound as a mixture with mono-bromo and unbrominated compounds;

LCMS: Rt 1.54 mins MS m/z 602.1 [M+H]+; Method 2 minLowpHv01

Step 2: 7-(6-oxo-2,3-di-p-tolyl-6,7-dihydro-5H-pyrrolo[2,3-b]pyrazin-5-yl)heptanoic acid 7-(7,7-Dibromo-6-oxo-2,3-di-p-tolyl-6,7-dihydro-5H-pyrrolo[2,3-b]pyrazin-5-yl)heptanoic acid (mixture from step 1) (127 mg, 0.211 mmol) in dry THF (5 ml) under nitrogen was treated with 10% Pd(C) (22.48 mg, 0.021 mmol) and the mixture was stirred at RT under an atmosphere of hydrogen for 16 hours. The resulting mixture was filtered through Celite® and washed through with DCM. The filtrate was concentrated under reduced pressure and purification was carried out by chromatography on silica eluting with 0-100% EtOAc in iso-hexane. Further purification was carried out by dissolving the product in DCM (minimal) and loading onto a 20 cm×20 cm preparative TLC plate. The plate was run using a solvent system of 75% EtOAc in iso-hexane (300 ml) and the appropriate strip of Si was scrapped off the plate. The silica was suspended in 10% MeOH/DCM and sonicated. The suspension was filtered, rinsing the solid with 10% MeOH/DCM. The filtrate was concentrated under reduced pressure to afford the title compound;

LCMS: Rt 1.34 mins MS m/z 444.5 [M+H]+Method 2 minLowpHv01

1H NMR (400 MHz, d-DMSO) δ 11.96 (1H, br s), 7.25 (2H, m), 7.20 (2H, m), 7.16-7.09 (4H, br m), 3.83 (2H, m), 3.74 (2H, m), 2.30 (3H, s), 2.29 (3H, s), 2.18 (2H, m), 1.73-1.64 (2H, br m), 1.52-1.44 (2H, br m), 1.36-1.28 (4H, br m)

EXAMPLE 16

7-(2,3-Dip-tolyl-6-(trifluoromethyl)-5H-pyrrolo[2,3-b]pyrazin-5-yl)heptanoic acid

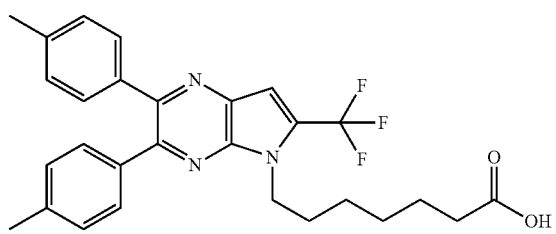 [SMILES: Cc1ccc(-c2nc3cc(C(F)(F)F)n(CCCCCCC(=O)O)c3nc2-c2ccc(C)cc2)cc1]

Step 1: 5,6-Dip-tolyl-3-(3,3,3-trifluoroprop-1-ynyl)pyrazin-2-amine

A solution of 3-bromo-5,6-di-p-tolylpyrazin-2-amine (Ex 1, step 3) (200 mg, 0.565 mmol) in dioxane (4 ml) bubbled with nitrogen was treated with tributyl(3,3,3-trifluoroprop-1-ynyl)stannane (238 mg, 0.621 mmol) and PdCl$_2$(dppf)-CH$_2$Cl$_2$-Adduct (46.1 mg, 0.056 mmol). The resulting mixture was heated at 140° C. for 1 hour using microwave radiation. After cooling to RT, the mixture was concentrated under reduced pressure. The crude residue was dissolved in DCM and loaded onto a 25 g Silica column. Purification by chromatography on silica eluting with 0-5% EtOAc in iso-hexane afford the title compound;

LCMS: Rt 1.51 mins MS m/z 368.5 [M+H]+; Method 2 minLowpHv01

Step 2: 2,3-Di-p-tolyl-6-(trifluoromethyl)-5H-pyrrolo[2,3-b]pyrazine

The title compound was prepared from 5,6-di-p-tolyl-3-(3,3,3-trifluoroprop-1-ynyl)pyrazin-2-amine (step 1) analogously to Ex 1 step 5;

LCMS: Rt 1.45 mins MS m/z 368.3 [M+H]+Method 2 minLowpHv01

Step 3: Ethyl 7-(2,3-dip-tolyl-6-(trifluoromethyl)-5H-pyrrolo[2,3-b]pyrazin-5-yl)heptanoate The title compound was prepared from 2,3-di-p-tolyl-6-(trifluoromethyl)-5H-pyrrolo[2,3-b]pyrazine (step 2) analogously to Ex 1 step 6;

LCMS: Rt 1.73 min MS m/z 524.4 [M+H]+: Method 2 minLowpHv01

Step 4: 7-(2,3-Di-p-tolyl-6-(trifluoromethyl)-5H-pyrrolo[2,3-b]pyrazin-5-yl)heptanoic acid The title compound was prepared from ethyl 7-(2,3-di-p-tolyl-6-(trifluoromethyl)-5H-pyrrolo[2,3-b]pyrazin-5-yl)heptanoate (step 3) analogously to Ex 1 step 7;

LCMS: Rt 1.57 mins MS m/z 496.6 [M+H]+; Method 2 minLowpHv01

EXAMPLE 17

7-(6,7-Diethyl-2,3-di-p-tolyl-5H-pyrrolo[2,3-b]pyrazin-5-yl)heptanoic acid

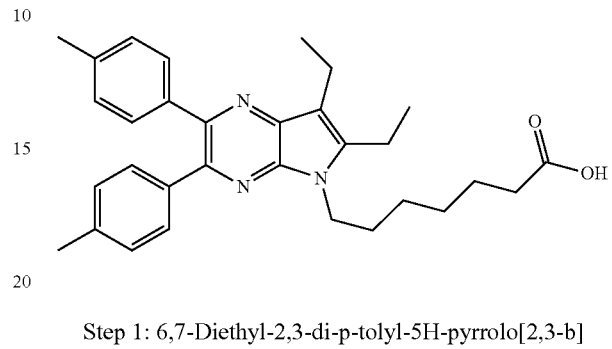

Step 1: 6,7-Diethyl-2,3-di-p-tolyl-5H-pyrrolo[2,3-b]pyrazine

Reference: J Org. Chem., Vol. 63, No. 22, 1998, 7652

A solution of 3-bromo-5,6-di-p-tolylpyrazin-2-amine (Ex 1, step 3) (20 mg, 0.056 mmol) in DMF (1 ml) bubbled with nitrogen was treated with hex-3-yne (0.013 ml, 0.113 mmol), palladium acetate (0.634 mg, 2.82 μmol), lithium chloride (2.393 mg, 0.056 mmol) and K$_2$CO$_3$ (39.0 mg, 0.282 mmol). The resulting mixture was heated at 120° C. for 30 min using microwave radiation. In parallel, a separate identical reaction mixture was prepared and heated thermally at 120° C. for 1 hour. After cooling to RT, the two reaction mixtures were combined in water (50 ml). The aqueous was extracted with EtOAc (×3). The combined organic extracts were washed sequentially with water (×1) and brine (×1), dried (MgSO4), filtered and concentrated under reduced pressure. Purification of the crude product by chromatography on silica eluting with 0-10% EtOAc in iso-hexane afforded the title compound;

LCMS: Rt 1.50 mins MS m/z 356.3 [M+H]+Method 2 minLowpHv01

Step 2: Ethyl 7-(6,7-diethyl-2,3-dip-tolyl-5H-pyrrolo[2,3-b]pyrazin-5-yl)heptanoate A solution of 6,7-diethyl-2,3-dip-tolyl-5H-pyrrolo[2,3-b]pyrazine (step 1) (14 mg, 0.039 mmol) in dry DMF (1 ml) under nitrogen was treated with NaH (1.733 mg, 0.043 mmol). The resulting mixture was stirred at RT for 20 minutes and treated with ethyl 7-bromoheptanoate (8.44 μl, 0.043 mmol). After stirring at RT for 3 hours, the mixture was added to water and the pH was adjusted to pH1 using 2M HCl. The aqueous was extracted with EtOAc (×3) and the combined organic extracts were sequentially washed with water (×1) and brine (×1), dried (MgSO4), filtered and concentrated under reduced pressure to afford the title compound (with trace hydrolysis acid product present);

LCMS: Rt 1.57 mins MS m/z 514.6 [M+H]+Method 2 minLowpH50v01

Step 3: 7-(6,7-Diethyl-2,3-di-p-tolyl-5H-pyrrolo[2,3-b]pyrazin-5-yl)heptanoic acid The title compound was prepared from ethyl 7-(6,7-diethyl-2,3-dip-tolyl-5H-pyrrolo[2,3-b]pyrazin-5-yl)heptanoate (step 2) analogously to Ex 1 step 7;

LCMS: Rt 1.63 mins MS m/z 484.6 [M+H]+Method 2 minLowpHv01

1H NMR (400 MHz, d-DMSO) δ 11.98 (1H, br s), 7.27-7.21 (4H, br m), 7.14-7.08 (4H, br m), 4.26-4.20 (2H, br m), 2.95-2.87 (2H, br m), 2.81-2.74 (2H, br m), 2.31 (3H, s), 2.31 (3H, s), 2.17-2.12 (2H, br m), 1.81-1.73 (2H, br m), 1.52-1.43 (2H, br m), 1.35-1.21 (10H, br m).

Preparation of Intermediates:

Intermediate A 2,3-Di-p-tolyl5H-pyrrolo[2,3-b]pyrazine

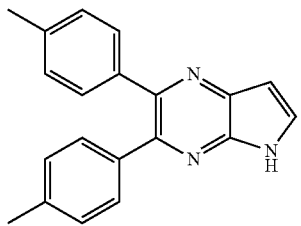 [SMILES: Cc1ccc(-c2nc3cc[nH]c3nc2-c2ccc(C)cc2)cc1]

Step 1: 6-Chloro-5-iodopyrazin-2-amine

A solution of 6-chloropyrazin-2-amine (10.0 g, 77 mmol) in DMSO (100 ml) was treated with 1-iodopyrrolidine-2,5-dione (20.84 g, 93 mmol). The reaction mixture was stirred at RT for 2 days and then added to water (800 ml). The pH was adjusted to pH 8-9 using a sat. NaHCO₃ solution and the resulting suspension was filtered, washing with water (×3) and dried under vacuum to afford the titled compound as an orange solid;

LC-MS Rt=0.83 mins; [MeCN+H]⁺ 296.0, Method 2 min-LowpH.

Step 2: 5,6-Di-p-tolylpyrazin-2-amine

A solution of 6-chloro-5-iodopyrazin-2-amine (step 1) (13.74 g, 53.8 mmol) in dioxane (300 ml) was degassed with N₂ and treated with p-tolylboronic acid (17.55 g, 129 mmol), K₂CO₃ (22.30 g, 161 mmol) and PdCl₂(dppf)-CH₂Cl₂-adduct (4.39 g, 5.38 mmol). The orange suspension was stirred at 110° C. for 2 days. After cooling to room temperature the reaction mixture was concentrated under reduced pressure. The crude mixture was absorbed onto silica and purification by chromatography eluting with 0-60% EtOAc in iso-hexane afforded the titled compound as a beige coloured solid;

LC-MS Rt=1.09 mins; [M+H]⁺ 277.3, Method 2 min-LowpH.

Step 3: 3-Bromo-5,6-di-p-tolylpyrazin-2-amine

A solution of 5,6-di-p-tolylpyrazin-2-amine (step 2) (4.94 g, 17.94 mmol) in DMSO (40 ml), was treated with N-bromosuccinimide (3.19 g, 17.94 mmol). The reaction mixture was stirred at room temperature for 2 hours to give a beige coloured suspension. The suspension was diluted with water (700 ml) and the pH was adjusted to pH 8-9 using a sat. NaHCO₃ solution. The suspension was filtered, washed with water (×3) and dried under vacuum to afford the titled compound as a beige coloured solid;

LC-MS Rt=1.39 mins; [M+H]⁺ 356.3, Method 2 min-LowpH.

Step 4: 5,6-Di-p-tolyl-3-((trimethylsilyl)ethynyl)pyrazin-2-amine

A solution of 3-bromo-5,6-di-p-tolylpyrazin-2-amine (step 3) in dry dioxane (10 ml) was degassed with N₂ and treated with triethylamine (1.062 ml, 7.62 mmol), ethynyltrimethylsilane (0.239 ml, 1.694 mmol), copper(I) iodide (48.4 mg, 0.254 mmol) and PdCl₂(dppf)-CH₂Cl₂-adduct (69.2 mg, 0.085 mmol). After stirring at room temperature for 5 hours, the reaction mixture was added to water (50 ml) and extracted with DCM (×3). The organic extracts were passed through a phase separating column and brine was added to aid separation. The solvent was removed under reduced pressure and purification of the crude product by chromatography on silica eluting with 0-5% EtOAc in iso-hexane afforded the titled compound;

LC-MS Rt=1.50 mins; [M+H]⁺ 372, Method 2 min-LC_v003.

Step 5: 2,3-Di-p-tolyl-5H-pyrrolo[2,3-b]pyrazine 5,6-Di-p-tolyl-3-((trimethylsilyl)ethynyl)pyrazin-2-amine (step 4) (170 mg, 0.458 mmol) in tert-BuOH (5 ml) at RT was treated with potassium tert-butoxide (205 mg, 1.830 mmol) and heated at reflux for 3 hours. After cooling to RT, conc. HCl (0.5 ml, 16.46 mmol) was added and the mixture was heated at reflux for 3 hours and stirred at RT overnight. The mixture was added to water (100 ml) and the pH was adjusted to pH 10 using 2M NaOH. The aqueous portion was extracted with DCM (×3) and the combined organic extracts were passed through a phase separating column. The solvent was removed under reduced pressure and purification of the crude product by chromatography on silica eluting with 0-20% EtOAc in iso-hexane afforded the titled compound;

LC-MS Rt=1.17 mins; [M+H]⁺ 300, Method 2 min-LC_v003.

1H NMR (400 MHz, DMSO-d6) δ 1H NMR (400 MHz, d-DMSO) δ 12.06 (1H, br s), 7.91 (1H, m), 7.25 (4H, m), 7.11 (4H, m), 6.67 (1H, d), 2.30 (3H, s), 2.30 (3H, s)

Intermediate B 7-(2,3-Di-p-tolyl-pyrrolo[2,3-b]pyrazin-5-yl)-heptanoic acid ethyl ester

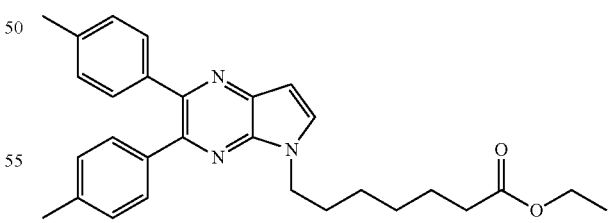

The titled compound was prepared from 2,3-di-p-tolyl-5H-pyrrolo[2,3-b]pyrazine (Intermediate A) analogously to ethyl 7-(6-cyclopropyl-2,3-di-p-tolyl-5H-pyrrolo[2,3-b]pyrazin-5-yl)heptanoate (Example 1 step 6);

LC-MS Rt=1.44 mins; [M+H]⁺ 456, Method 2 min-LC_v003.

¹H NMR (400 MHz, d-DMSO) δ 7.99 (1H, m), 7.26 (4H, m), 7.12 (4H, m), 6.69 (1H, d), 4.29 (2H, t), 4.01 (2H, q), 2.31

(3H, s), 2.31 (3H, s), 2.22 (2H, t), 1.85 (2H, br m), 1.49 (2H, br m), 1.36-1.22 (4H, br m), 1.15 (3H, t).

Intermediate C

Ethyl 7-(7-Formyl-2,3-di-p-tolyl-5H-pyrrolo[2,3-b]pyrazin-5-yl)heptanoate

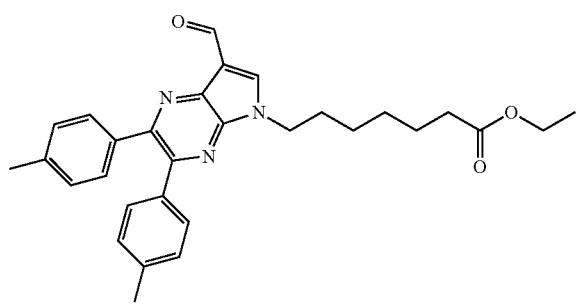 [SMILES: CCOC(=O)CCCCCCn1cc(C=O)c2nc(-c3ccc(C)cc3)c(-c3ccc(C)cc3)nc21]

Step 1: Ethyl 7-(7-formyl-2,3-di-p-tolyl-5H-pyrrolo[2,3-b]pyrazin-5-yl)heptanoate A mixture comprising 7-(2,3-di-p-tolyl-pyrrolo[2,3-b]pyrazin-5-yl)-heptanoic acid ethyl ester (Intermediate B) (479 mg, 1.051 mmol) in anhydrous DMF (1 ml) was degassed with $N_2$ and treated dropwise with $POCl_3$ (0.147 ml, 1.577 mmol). The mixture was stirred at room temperature for 3 hours and treated with a further portion of $POCl_3$ (0.147 ml, 1.577 mmol). After stirring at RT for 16 hours, the mixture was partitioned between water (100 ml) and EtOAc (20 ml) and the pH of the bi-phasic solution was adjusted to pH 8-9 using sat. $NaHCO_3$ solution. The aqueous portion was extracted with EtOAc (×3) and the combined organic extract were washed with water (×1), brine (×1), dried over $MgSO_4$ and filtered and concentrated under reduced pressure to afford the titled compound as a brown oil;

LC-MS Rt=1.37 mins; $[M+H]^+$ 484.6, Method 2 min-LowpH.

Intermediate D 7-(2-Bromo-3-chloro-6-cyclopropyl-pyrrolo[2,3-b]pyrazin-5-yl)-heptanoic acid ethyl ester

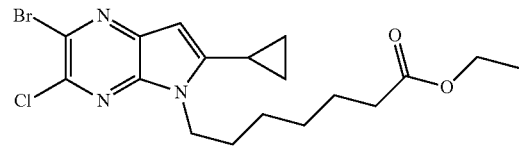 [SMILES: CCOC(=O)CCCCCCn1c(C2CC2)cc2nc(Br)c(Cl)nc21]

Step 1: 2-Bromo-3-chloro-6-cyclopropyl-5H-pyrrolo[2,3-b]pyrazine

The titled compound was prepared from 6-chloropyrazin-2-amine (commercial) analogously to 2-bromo-3-chloro-6-methyl-5H-pyrrolo[2,3-b]pyrazine (Example 9 step 1 to step 3) by replacing trimethyl(prop-2-ynyl)silane (step 2) with ethynylcyclopropane.

Step 2: 7-(2-Bromo-3-chloro-6-cyclopropyl-pyrrolo[2,3-b]pyrazin-5-yl)-heptanoic acid ethyl ester 2-Bromo-3-chloro-6-cyclopropyl-5H-pyrrolo[2,3-b]pyrazine (step 1) (1.0 g, 3.696 mmol) in DMF (10 ml), cooled to 0° C. and degassed with argon, was treated with potassium carbonate (1.53 g, 10.88 mmol) and stirred for 5 minutes. The reaction mixture was then treated with ethyl 7-bromoheptanoate (960 mg, 4.066 mmol) and stirred at room temperature for 16 hours. Saturated aqueous ammonium chloride solution was added slowly at 0° C. and the mixture was extracted with diethyl ether. The organic portion was dried ($Na_2SO_4$), and the solvent was removed under reduced pressure. Purification of the crude product by chromatography on neutral alumina eluting with 0-2% EtOAc in iso-hexane afforded the titled compound;

MS: m/z $[M+H]^+$ 428

HPLC: Rt 5.77 mins

Prophetic Compounds

The following compounds may be prepared according to similar methods as disclosed herein.

| Structure | Name |
|---|---|
| 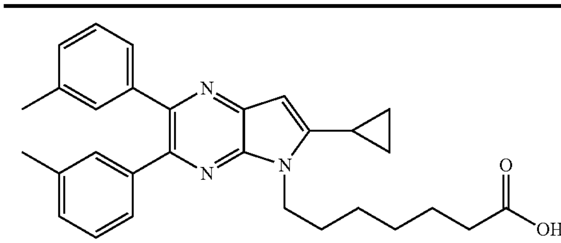 | 7-(6-cyclopropyl-2,3-di-m-tolyl-5H-pyrrolo[2,3-b]pyrazin-5-yl)heptanoic acid |
| 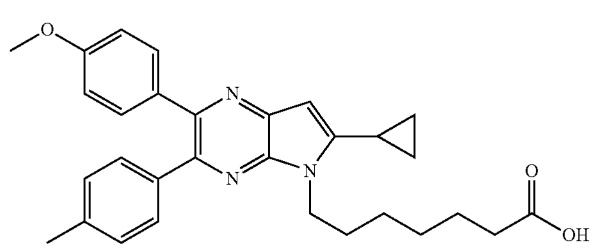 [SMILES: COc1ccc(-c2nc3cc(C4CC4)n(CCCCCCC(=O)O)c3nc2-c2ccc(C)cc2)cc1] | 7-(6-cyclopropyl-2-(4-methoxyphenyl)-3-(p-tolyl)-5H-pyrrolo[2,3-b]pyrazin-5-yl)heptanoic acid |

| Structure | Name |
|---|---|
| 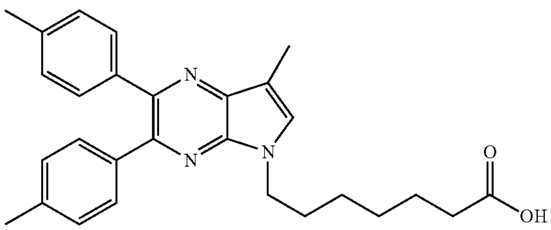 | 7-(7-methyl-2,3-di-p-tolyl-5H-pyrrolo[2,3-b]pyrazin-5-yl)heptanoic acid |
| 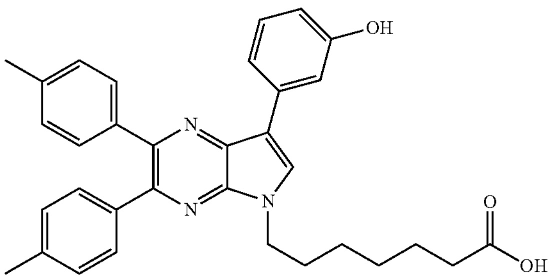 [SMILES: Cc1ccc(-c2nc3c(-c4cccc(O)c4)cn(CCCCCCC(=O)O)c3nc2-c2ccc(C)cc2)cc1] | 7-(7-(3-hydroxyphenyl)-2,3-di-p-tolyl-5H-pyrrolo[2,3-b]pyrazin-5-yl)heptanoic acid |
| 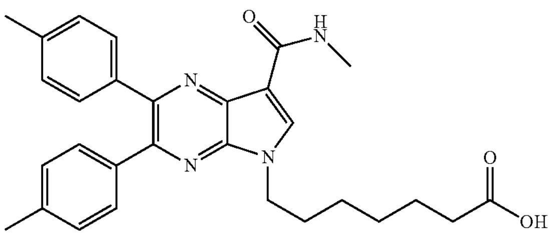 [SMILES: CNC(=O)c1cn(CCCCCCC(=O)O)c2nc(-c3ccc(C)cc3)c(-c3ccc(C)cc3)nc12] | 7-(7-(methylcarbamoyl)-2,3-di-p-tolyl-5H-pyrrolo[2,3-b]pyrazin-5-yl)heptanoic acid |
| 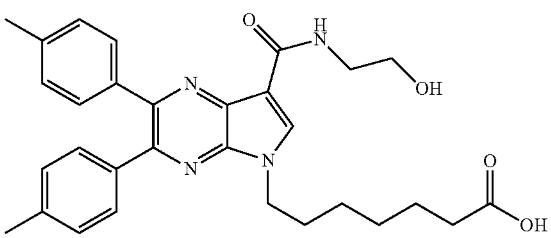 [SMILES: Cc1ccc(-c2nc3c(C(=O)NCCO)cn(CCCCCCC(=O)O)c3nc2-c2ccc(C)cc2)cc1] | 7-(7-((2-hydroxyethyl)carbamoyl)-2,3-di-p-tolyl-5H-pyrrolo[2,3-b]pyrazin-5-yl)heptanoic acid |
| 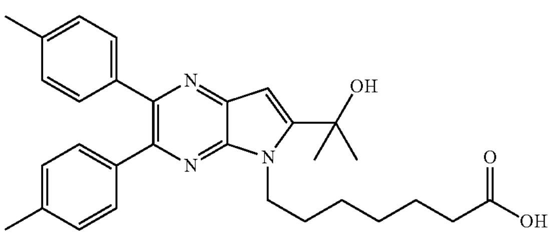 [SMILES: Cc1ccc(-c2nc3cc(C(C)(C)O)n(CCCCCCC(=O)O)c3nc2-c2ccc(C)cc2)cc1] | 7-(6-(2-hydroxypropan-2-yl)-2,3-di-p-tolyl-5H-pyrrolo[2,3-b]pyrazin-5-yl)heptanoic acid |
| 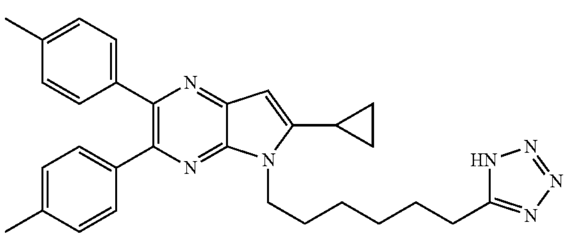 [SMILES: Cc1ccc(-c2nc3cc(C4CC4)n(CCCCCCc4nnn[nH]4)c3nc2-c2ccc(C)cc2)cc1] | 6-Cyclopropyl-5-[6-(1H-tetrazol-5-yl)-hexyl]-2,3-di-p-tolyl-5H-pyrrolo[2,3-b]pyrazine |

-continued

| Structure | Name |
|---|---|
| 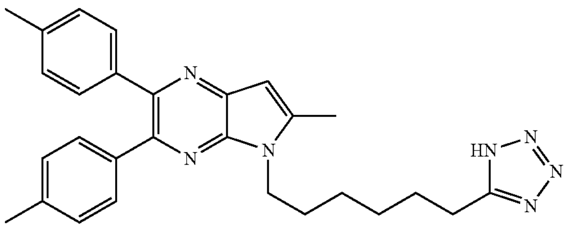 [SMILES: Cc1ccc(-c2nc3cc(C)n(CCCCCCc4nnn[nH]4)c3nc2-c2ccc(C)cc2)cc1] | 6-Methyl-5-[6-(1H-tetrazol-5-yl)-hexyl]-2,3-di-p-tolyl-5H-pyrrolo[2,3-b]pyrazine |
| 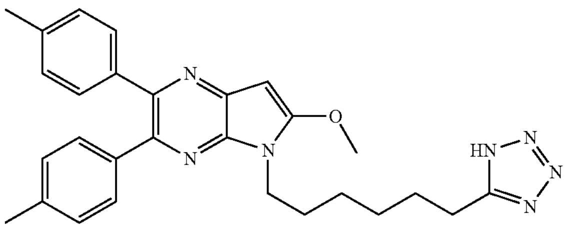 [SMILES: COc1cc2nc(-c3ccc(C)cc3)c(-c3ccc(C)cc3)nc2n1CCCCCCc1nnn[nH]1] | 6-Methoxy-5-[6-(1H-tetrazol-5-yl)-hexyl]-2,3-di-p-tolyl-5H-pyrrolo[2,3-b]pyrazine |
| 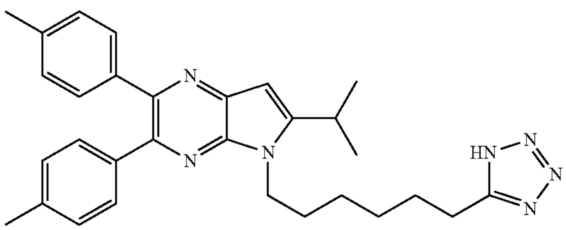 [SMILES: Cc1ccc(-c2nc3cc(C(C)C)n(CCCCCCc4nnn[nH]4)c3nc2-c2ccc(C)cc2)cc1] | 6-Isopropyl-5-[6-(1H-tetrazol-5-yl)-hexyl]-2,3-di-p-tolyl-5H-pyrrolo[2,3-b]pyrazine |
| 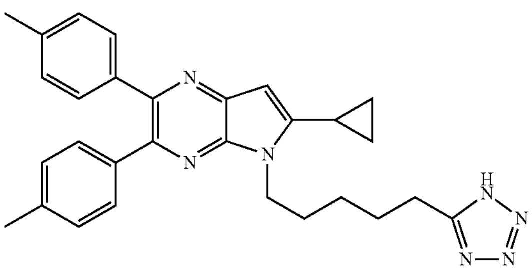 [SMILES: Cc1ccc(-c2nc3cc(C4CC4)n(CCCCCc4nnn[nH]4)c3nc2-c2ccc(C)cc2)cc1] | 6-Cyclopropyl-5-[5-(1H-tetrazol-5-yl)-pentyl]-2,3-di-p-tolyl-5H-pyrrolo[2,3-b]pyrazine |
| 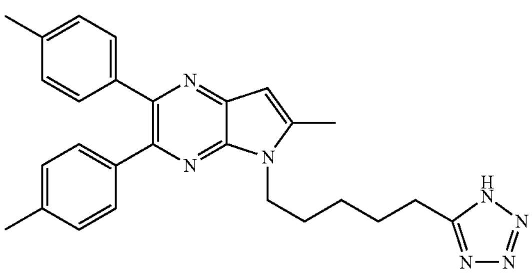 [SMILES: Cc1ccc(-c2nc3cc(C)n(CCCCCc4nnn[nH]4)c3nc2-c2ccc(C)cc2)cc1] | 6-Methyl-5-[5-(1H-tetrazol-5-yl)-pentyl]-2,3-di-p-tolyl-5H-pyrrolo[2,3-b]pyrazine |
| 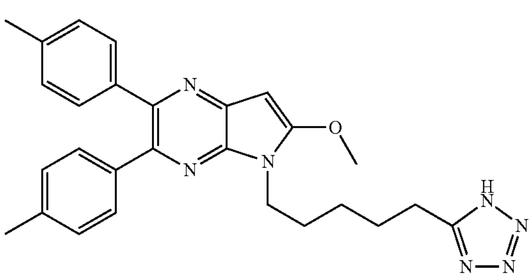 [SMILES: COc1cc2nc(-c3ccc(C)cc3)c(-c3ccc(C)cc3)nc2n1CCCCCc1nnn[nH]1] | 6-Methoxy-5-[5-(1H-tetrazol-5-yl)-pentyl]-2,3-di-p-tolyl-5H-pyrrolo[2,3-b]pyrazine |

-continued

| Structure | Name |
|---|---|
| 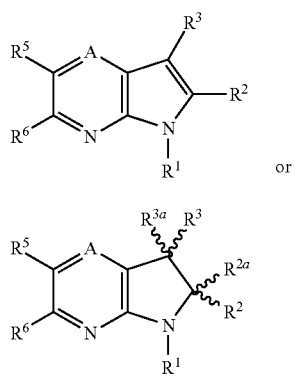 | 6-Isopropyl-5-[6-(1H-tetrazol-5-yl)-pentyl]-2,3-di-p-tolyl-5H-pyrrolo[2,3-b]pyrazine |

CONSISTORY CLAUSES

Embodiment 1

A compound represented by formula (Ia)

(Ib)

or a pharmaceutically acceptable salt thereof, wherein
A is N or CR;
R' is H, $C_1$-$C_8$ alkyl optionally substituted by one or more halogen atoms;
$R^1$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —($C_2$-$C_4$ alkyl)-$NR^{19}R^{21}$ and $C_3$-$C_7$ cycloalkyl; or
$R^1$ is —X—Y; or
$R^1$ is —W—$R^7$—X—Y; or
$R^1$ is —S(O)$_2$—X—Y; or
$R^1$ is —S(O)$_2$—W—$R^7$—X—Y;
$R^2$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; $C_1$-$C_4$ alkoxy; —($C_0$-$C_4$ alkyl)-$NR^{19}R^{21}$ and $C_3$-$C_7$ cycloalkyl; or
$R^2$ is —X—Y; or
$R^2$ is —W—$R^7$—X—Y; or
$R^2$ is —S(O)$_2$—X—Y; or
$R^2$ is —S(O)$_2$—W—$R^7$—X—Y;
$R^{2a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or
$R^2$ and $R^{2a}$ taken together are oxo;
wherein one of $R^1$ and $R^2$ is —X—Y, —W—$R^7$—X—Y, —S(O)$_2$—X—Y; or —S(O)$_2$—W—$R^7$—X—Y;
$R^3$ is independently selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —OH; OR'; —($C_0$-$C_4$alkyl)-$NR^{19}R^{21}$; CN; halogen; —($C_0$-$C_4$alkyl)-$C_6$-$C_{14}$aryl; —($C_0$-$C_4$alkyl)-4 to 14 membered heteroaryl; —C(=O)H; —C(=O)OH; —C(=O)$NR^{19}R^{21}$ and $C_3$-$C_7$ cycloalkyl, wherein the aryl and heteroaryl are optionally substituted by one or more substituents independently selected from OH, $C_1$-$C_4$ alkyl, $C_1$-$C_4$ alkoxy, halogens and $C_1$-$C_4$ haloalkyl;
$R^{3a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or $R^3$ and $R^{3a}$ taken together are oxo;
$R^5$ and $R^6$ are independently selected from —($C_0$-$C_4$ alkyl)-$C_6$-$C_{14}$ aryl and —($C_0$-$C_4$ alkyl)-4 to 14 membered heteroaryl, wherein the aryl and heteroaryl are each optionally substituted by one or more Z substituents;
W is $C_1$-$C_8$ alkylene optionally substituted by hydroxy, halogens or $C_1$-$C_4$ alkyl;
X is $C_1$-$C_8$ alkylene optionally substituted by hydroxy, halogens or $C_1$-$C_4$ alkyl;
Y is carboxy, $C_1$-$C_4$-alkoxycarbonyl, tetrazolyl, —C(=O)$NR^{19}R^{21}$ or —CONH—S(O)$_q$—$R^x$, wherein
$R^x$ is phenyl, benzyl or —$NR^{19}R^{21}$;
q is 0, 1 or 2;
$R^7$ is a divalent moiety represented by —O—, —S—, —NHC(O)—, —$CH_2$=$CH_2$—, —$C_6$-$C_{14}$ aryl-D-; -3 to 14 membered heterocyclyl-D-, wherein the heterocyclyl contains at least one heteroatom selected from N, O and S, wherein D is O, S, NH or not present;
Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclyl, wherein the heterocyclyl contains at least one heteroatom selected from N, O and S;
$R^{18}$ is independently H or $C_1$-$C_6$ alkyl;
$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; —($C_1$-$C_4$ alkyl)-carboxy; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclyl, the heterocyclyl including one or more heteroatoms selected from N, O and S, optionally substituted by one or more groups selected from halogen, oxo, $C_1$-$C_6$ alkyl and C(O)$C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl;

wherein the alkyl groups are optionally substituted by one or more halogen atoms, OH, $C_1$-$C_4$ alkoxy, C(O)NH$_2$, C(O)NH$C_1$-$C_6$ alkyl or C(O)N($C_1$-$C_6$ alkyl)$_2$; or $R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; S(O)$_2$-aryl; S(O)$_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and C(O)O$C_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 2

The compound according to embodiment 1, wherein
wherein one of $R^1$ and $R^2$ is —X—Y, —W—$R^7$—X—Y, —S(O)$_2$—X—Y; or —S(O)$_2$—W—$R^7$—X—Y;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is carboxy, $C_1$-$C_4$-alkoxycarbonyl, tetrazolyl, —C(=O)N$R^{19}R^{21}$ or —CONH—S(O)$_q$—$R^x$, wherein $R^x$ is phenyl, benzyl or —N$R^{19}R^{21}$;
q is 2;
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and
$R^{19}$ and $R^{21}$ are each independently H; $C_1$-$C_8$ alkyl.

Embodiment 3

The compound according to embodiment 1 or 2, wherein
one of $R^1$ and $R^2$ is —X—Y; or —W—$R^7$—X—Y;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is carboxy, $C_1$-$C_4$-alkoxycarbonyl, tetrazolyl, —C(=O)N$R^{19}R^{21}$ or —CONH—S(O)$_q$—$R^x$,
wherein $R^x$ is phenyl, benzyl or —N$R^{19}R^{21}$;
q is 2;
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and
$R^{19}$ and $R^{21}$ are each independently H; $C_1$-$C_8$ alkyl.

Embodiment 4

The compound according to any one of embodiments 1 to 3, wherein
one of $R^1$ and $R^2$ is —X—Y; or —W—$R^7$—X—Y;
W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;
Y is —C(O)OH; and
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

Embodiment 5

The compound according to embodiment 1, wherein
one of $R^1$ and $R^2$ is —(CH$_2$)$_m$—C(O)OR", or —(CH$_2$)$_m$—$R^7$—(CH$_2$)$_n$—C(O)OR";
m is 1, 2, 3, 4, 5, 6, 7 or 8;
n is 0, 1, 2 or 3;
R" is H or $C_1$-$C_4$ alkyl optionally substituted by one or more halogen atoms; and
$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O.

Embodiment 6

The compound according to embodiments 5, wherein
one of $R^1$ and $R^2$ is —(CH$_2$)$_m$—C(O)OR";
m is 3, 4, 5, 6, 7 or 8; and
R" is H or $C_1$-$C_4$ alkyl optionally substituted by one or more halogen atoms.

Embodiment 7

The compound according to any one of embodiments 5 or 6, wherein
one of $R^1$ and $R^2$ is —(CH$_2$)$_m$—C(O)OR";
R" is H; and
m is 4, 5 or 6.

Embodiment 8

The compound according to embodiment 1, wherein
one of $R^1$ and $R^2$ is

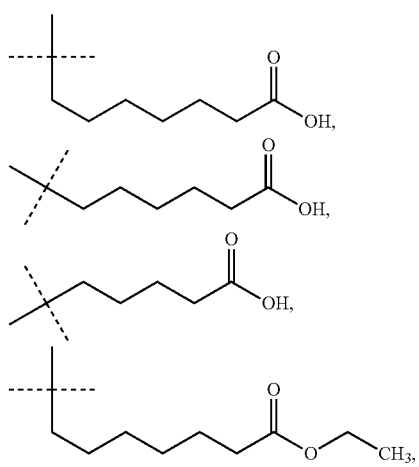

-continued

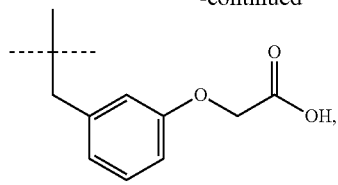

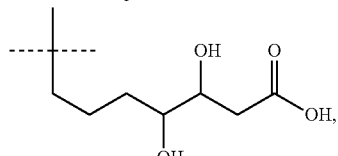

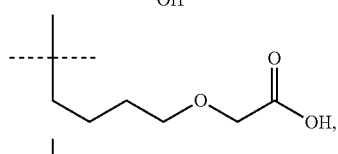

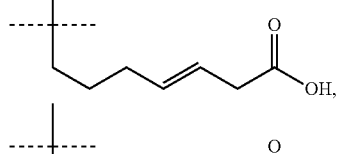

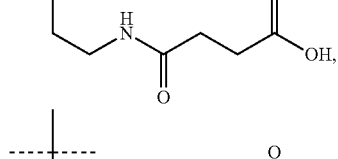

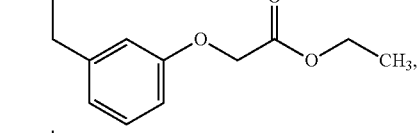

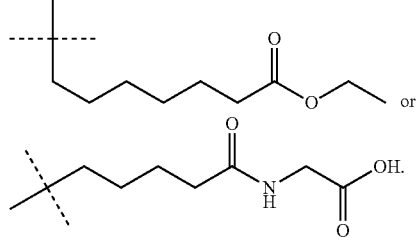

or

Embodiment 9

The compound according to any one of embodiments 1 to 8, wherein
$R^2$ is H, $C_1$-$C_8$ alkyl optionally substituted by one or more halogen atoms, $C_1$-$C_4$ alkoxy, $C_3$-$C_7$cycloalkyl;
if present $R^{2a}$ is H; or
$R^2$ and $R^{2a}$ together are oxo;
R' is H, $C_1$-$C_4$ alkyl.

Embodiment 10

The compound according to embodiment 9, wherein
$R^2$ is H, $C_1$-$C_8$ alkyl optionally substituted by one or more halogen atoms, $C_1$-$C_4$ alkoxy, $C_3$-$C_7$cycloalkyl.

Embodiment 11

The compound according to embodiment 10, wherein
$R^2$ is H, cyclopropyl, isopropyl, methoxy or methyl.

Embodiment 12

The compound according to any one of the preceding embodiments, wherein
$R^3$ and $R^{3a}$ are independently selected from H; $C_1$-$C_4$ alkyl optionally substituted by one or more halogen atoms or OH; —C(=O)H; —($C_0$-$C_4$alkyl)-$NR^{19}R^{21}$ and OH; or $R^3$ and $R^{3a}$ taken together are oxo.

Embodiment 13

The compound according to any one of the preceding embodiments, wherein
$R^3$ and $R^{3a}$ are independently selected from H; $C_1$-$C_4$ alkyl optionally substituted by one or more halogen atoms or OH; —C(=O)H and OH; or $R^3$ and $R^{3a}$ taken together are oxo.

Embodiment 14

The compound according to any one of the preceding embodiments, wherein
$R^5$ and $R^6$ are independently selected from $C_6$-$C_{14}$ aryl and 5 to 6 membered heteroaryl, wherein the heteroaryl contains at least one heteroatom selected from N, O and S, wherein the aryl and heteroaryl are each optionally substituted by one or more Z substituents.

Embodiment 15

The compound according to any one of embodiments 1 to 13, wherein
$R^5$ and $R^6$ are independently selected from phenyl; 2-pyridyl, 3-pyridyl, or 4-pyridyl,
wherein the phenyl, 2-pyridyl, 3-pyridyl, and 4-pyridyl are each optionally substituted by one or more Z substituents.

Embodiment 16

The compound according to any one of the embodiments 1 to 13, wherein
$R^5$ and $R^6$ are independently selected from phenyl optionally substituted by OH, $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; $NR^{19}R^{21}$; $C(O)OR^{19}$; $C(O)R^{19}$; $SR^{19}$; $OR^{19}$; CN; $NO_2$; and halogen.

Embodiment 17

The compound according to any one of embodiments 1 to 13, wherein
$R^5$ and $R^6$ are independently selected from phenyl optionally substituted by $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; and halogen.

Embodiment 18

The compound according to any one of embodiments 1 to 13, wherein
$R^5$ and $R^6$ are independently selected from phenyl optionally substituted by $C_1$-$C_4$ alkoxy or halogen, and $C_1$-$C_4$ alkyl optionally substituted by one or more halogen atoms.

Embodiment 19

The compound according to any one of embodiments 1 to 13, wherein $R^5$ and $R^6$ are independently selected from phenyl optionally substituted by methyl, ethyl, trifluoromethyl, methoxy or halogen.

Embodiment 20

The compound according to any one of embodiments 1 to 13, wherein $R^5$ is

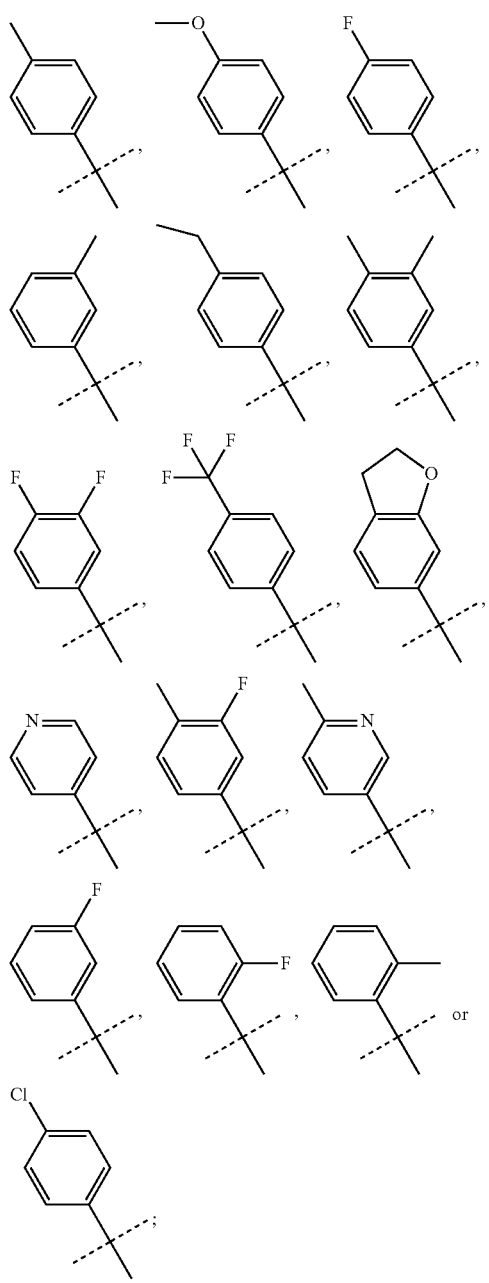

and
$R^6$ is

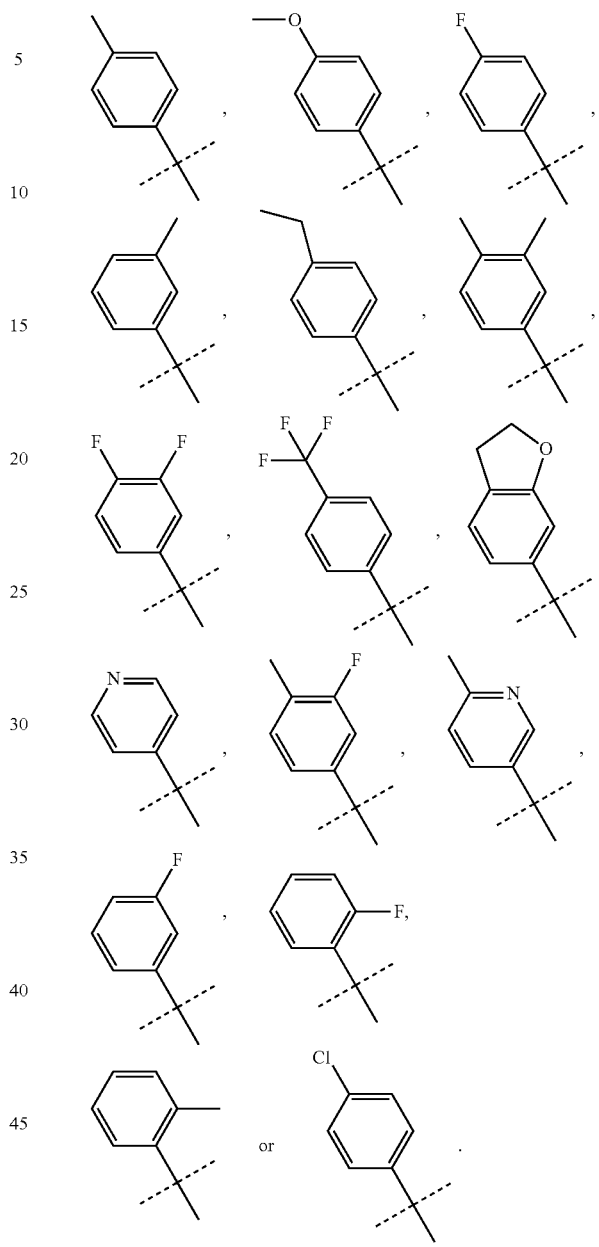

Embodiment 21

The compound according to any proceeding embodiment, wherein A is N.

Embodiment 22

The compound according to embodiment 1 to 21, wherein A is CR'.

Embodiment 23

The compound according to embodiment 22, wherein R' is H.

Embodiment 24

The compound according to any one of embodiments 1 to 23, wherein formula Ib has the following stereochemistry:

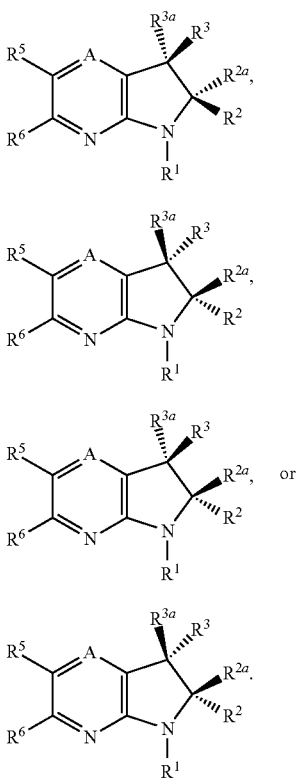

(Ib')

(Ib'')

(Ib''')

(Ib'''')

Embodiment 25

The compound according to any one of embodiments 1 to 23, wherein the compound is represented by formula (Ia)

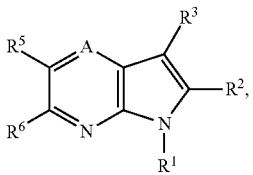

(Ia)

or a pharmaceutically acceptable salt thereof.

Embodiment 26

The compound according to embodiment 1, wherein the compound is represented by formula (Ia)

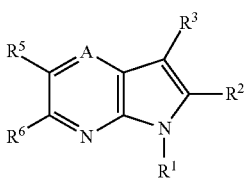

(Ia)

or a pharmaceutically acceptable salt thereof, wherein
A is N or CR;
R' is H, $C_1$-$C_8$ alkyl optionally substituted by one or more halogen atoms;

$R^1$ is —X—Y; or
$R^1$ is —W—$R^7$—X—Y; or
$R^1$ is —S(O)$_2$—X—Y; or
$R^1$ is —S(O)$_2$—W—$R^7$—X—Y;
$R^2$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; $C_1$-$C_4$ alkoxy; —($C_0$-$C_4$ alkyl)-NR$^{19}$R$^{21}$ and $C_3$-$C_7$ cycloalkyl;
$R^3$ is independently selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —OH; OR'; —($C_0$-$C_4$alkyl)-NR$^{19}$R$^{21}$; CN; halogen; —($C_0$-$C_4$alkyl)-$C_6$-$C_{14}$aryl; —($C_0$-$C_4$alkyl)-4 to 14 membered heteroaryl; —C(=O)H; —C(=O)OH; —C(=O)NR$^{19}$R$^{21}$ and $C_3$-$C_7$ cycloalkyl, wherein the aryl and heteroaryl are optionally substituted by one or more substituents independently selected from OH, $C_1$-$C_4$ alkyl, $C_1$-$C_4$ alkoxy, halogens and $C_1$-$C_4$ haloalkyl;
$R^5$ and $R^6$ are independently selected from —($C_0$-$C_4$ alkyl)-$C_6$-$C_{14}$ aryl and —($C_0$-$C_4$ alkyl)-4 to 14 membered heteroaryl, wherein the aryl and heteroaryl are each optionally substituted by one or more Z substituents;
W is $C_1$-$C_8$ alkylene optionally substituted by hydroxy, halogens or $C_1$-$C_4$ alkyl;
X is $C_1$-$C_8$ alkylene optionally substituted by hydroxy, halogens or $C_1$-$C_4$ alkyl;
Y is carboxy, $C_1$-$C_4$-alkoxycarbonyl, tetrazolyl, —C(=O)NR$^{19}$R$^{21}$ or —CONH—S(O)$_q$—R$^x$, wherein R$^x$ is phenyl, benzyl or —NR$^{19}$R$^{21}$;
q is 0, 1 or 2;
$R^7$ is a divalent moiety represented by —O—, —S—, —NHC(O)—, —CH$_2$=CH$_2$—, —$C_6$-$C_{14}$ aryl-D-; -3 to 14 membered heterocyclyl-D-, wherein the heterocyclyl contains at least one heteroatom selected from N, O and S, wherein D is O, S, NH or not present;
Z is independently OH, aryl, O-aryl, benzyl, O-benzyl, $C_1$-$C_6$ alkyl optionally substituted by one or more OH groups or NH$_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogens, $C_1$-$C_6$ alkoxy optionally substituted by $C_1$-$C_4$ alkoxy, NR$^{18}$(SO$_2$)R$^{21}$, (SO$_2$)NR$^{19}$R$^{21}$, (SO$_2$)R$^{21}$, NR$^{18}$C(O)R$^{21}$, C(O)NR$^{19}$R$^{21}$, NR$^{18}$C(O)NR$^{19}$R$^{21}$, NR$^{18}$C(O)OR$^{19}$, NR$^{19}$R$^{21}$, C(O)OR$^{19}$, C(O)R$^{19}$, SR$^{19}$, OR$^{19}$, oxo, CN, NO$_2$, halogen or a 3 to 14 membered heterocyclyl, wherein the heterocyclyl contains at least one heteroatom selected from N, O and S;
$R^{18}$ is independently H or $C_1$-$C_6$ alkyl;
$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; —($C_1$-$C_4$ alkyl)-carboxy; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclyl, the heterocyclyl including one or more heteroatoms selected from N, O and S, optionally substituted by one or more groups selected from halogen, oxo, $C_1$-$C_6$ alkyl and C(O)$C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl;
wherein the alkyl groups are optionally substituted by one or more halogen atoms, OH, $C_1$-$C_4$ alkoxy, C(O)NH$_2$, C(O)NHC$_1$-$C_6$ alkyl or C(O)N($C_1$-$C_6$ alkyl)$_2$; or $R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 27

The compound according to embodiment 1, wherein the compound is represented by formula (Ia)

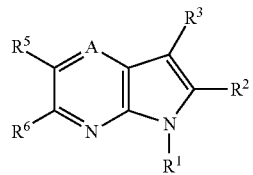

(Ia)

or a pharmaceutically acceptable salt thereof, wherein
A is N;
$R^1$ is —X—Y; or
$R^1$ is —$S(O)_2$—X—Y;
$R^2$ is selected from H; $C_1$-$C_8$ alkyl optionally substituted by one or more halogen atoms, OH or $C_1$-$C_4$ alkoxy; $C_1$-$C_4$ alkoxy; and $C_3$-$C_7$ cycloalkyl;
$R^3$ is independently selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —OH; —($C_0$-$C_4$alkyl)-$NR^{19}R^{21}$; CN; halogen; —($C_0$-$C_4$alkyl)-$C_6$-$C_{14}$aryl; —($C_0$-$C_4$alkyl)-4 to 14 membered heteroaryl; —C(=O)H; —C(=O)OH; —C(=O)$NR^{19}R^{21}$ and $C_3$-$C_7$ cycloalkyl, wherein the aryl and heteroaryl are optionally substituted by one or more substituents independently selected from OH, $C_1$-$C_4$ alkyl, $C_1$-$C_4$ alkoxy, halogens and $C_1$-$C_4$ haloalkyl;
$R^5$ and $R^6$ are independently selected from —($C_0$-$C_4$ alkyl)-$C_6$-$C_{14}$ aryl and —($C_0$-$C_4$ alkyl)-4 to 14 membered heteroaryl, wherein the aryl and heteroaryl are each optionally substituted by one or more Z substituents;
X is $C_1$-$C_8$ alkylene optionally substituted by hydroxy, halogens or $C_1$-$C_4$ alkyl;
Y is carboxy or $C_1$-$C_4$-alkoxycarbonyl;
Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$ alkoxy, $NR^{18}(SO_2)R^{21}$, $(SO_2)NR^{19}R^{21}$, $(SO_2)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclyl, wherein the heterocyclyl contains at least one heteroatom selected from N, O and S;
$R^{18}$ is independently H or $C_1$-$C_6$ alkyl;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; —($C_1$-$C_4$ alkyl)-carboxy; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclyl, the heterocyclyl including one or more heteroatoms selected from N, O and S, optionally substituted by one or more groups selected from halogen, oxo, $C_1$-$C_6$ alkyl and $C(O)C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or $C(O)C_1$-$C_6$ alkyl;
wherein the alkyl groups are optionally substituted by one or more halogen atoms, OH, $C_1$-$C_4$ alkoxy, $C(O)NH_2$, $C(O)NHC_1$-$C_6$ alkyl or $C(O)N(C_1$-$C_6$ alkyl)$_2$; or
$R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 28

The compound according to embodiment 1, wherein the compound is represented by formula (Ia)

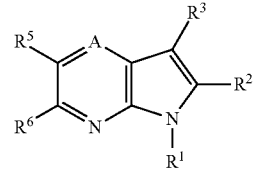

(Ia)

or a pharmaceutically acceptable salt thereof, wherein
A is N;
$R^1$ is —X—Y; or
$R^2$ is selected from H; $C_1$-$C_8$ alkyl optionally substituted by one or more halogen atoms, OH or $C_1$-$C_4$ alkoxy; $C_1$-$C_4$ alkoxy; and $C_3$-$C_7$ cycloalkyl;
$R^3$ is independently selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —OH; —($C_0$-$C_4$alkyl)-$NR^{19}R^{21}$; CN; halogen;
$R^5$ and $R^6$ are independently selected from —($C_0$-$C_4$ alkyl)-phenyl, wherein the phenyl is optionally substituted by one or more Z substituents;
X is $C_1$-$C_8$ alkylene optionally substituted by hydroxy, halogens or $C_1$-$C_4$ alkyl;
Y is carboxy or $C_1$-$C_4$-alkoxycarbonyl;
Z is independently OH, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, C₁-C₆ alkoxy optionally substituted by C₁-C₄ alkoxy.

Embodiment 29

The compound according to embodiment 1, wherein the compound is represented by formula (Ia)

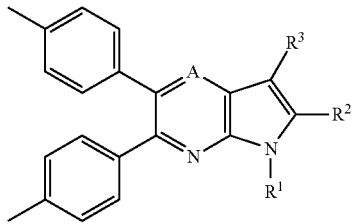

(Ia)

or a pharmaceutically acceptable salt thereof, wherein
A is N;
R¹ is —X—Y; or
R² is selected from H; C₁-C₈ alkyl optionally substituted by one or more halogen atoms, OH or C₁-C₄ alkoxy; C₁-C₄ alkoxy; and C₃-C₇ cycloalkyl;
R³ is independently selected from H; C₁-C₈ alkyl optionally substituted by one or more halogen atoms, OH, C₁-C₄ alkoxy, C₃-C₇ cycloalkyl or C₃-C₇ cycloalkyloxy; —OH; —(C₀-C₄alkyl)-NR¹⁹R²¹; CN; halogen;
X is C₄-C₇ alkylene;
Y is carboxy or C₁-C₄-alkoxycarbonyl.

Embodiment 30

The compound according to embodiment 1, the compound is selected from
7-(6-cyclopropyl-2,3-di-p-tolyl-5H-pyrrolo[2,3-b]pyrazin-5-yl)heptanoic acid;
ethyl 7-(6-cyclopropyl-2,3-di-p-tolyl-5H-pyrrolo[2,3-b]pyrazin-5-yl)heptanoate;
7-(6-isopropyl-2,3-di-p-tolyl-pyrrolo[2,3-b]pyrazin-5-yl)-heptanoic acid;
ethyl 7-(6-isopropyl-2,3-di-p-tolyl-5H-pyrrolo[2,3-b]pyrazin-5-yl)heptanoate;
7-(2,3-di-p-tolyl-pyrrolo[2,3-b]pyrazin-5-yl)-heptanoic acid ethyl ester;
7-(2,3-di-p-tolyl-pyrrolo[2,3-b]pyrazin-5-yl)-heptanoic acid;
7-(7-formyl-2,3-di-p-tolyl-5H-pyrrolo[2,3-b]pyrazin-5-yl) heptanoic acid;
7-(7-(hydroxymethyl)-2,3-di-p-tolyl-5H-pyrrolo[2,3-b] pyrazin-5-yl)heptanoic acid;
ethyl 7-(7-(hydroxymethyl)-2,3-di-p-tolyl-5H-pyrrolo[2,3-b]pyrazin-5-yl)heptanoate;
ethyl 7-(7-((isopropylamino)methyl)-2,3-di-p-tolyl-5H-pyrrolo[2,3-b]pyrazin-5-yl)heptanoate;
7-(7-((isopropylamino)methyl)-2,3-di-p-tolyl-5H-pyrrolo[2,3-b]pyrazin-5-yl)heptanoic acid;
7-(6-methoxy-2,3-di-p-tolyl-pyrrolo[2,3-b]pyrazin-5-yl)-heptanoic acid;
ethyl 7-(2,3-di-p-tolyl-6,7-dihydro-5H-pyrrolo[2,3-b] pyrazin-5-yl)heptanoate;
5-(2,3-di-p-tolyl-5H-pyrrolo[2,3-b]pyrazin-6-yl)-pentanoic acid;
2-(5-(2,3-di-p-tolyl-5H-pyrrolo[2,3-b]pyrazin-6-yl)pentanamido)acetic acid;
7-(6-methyl-2,3-di-p-tolyl-5H-pyrrolo[2,3-b]pyrazin-5-yl) heptanoic acid;
7-(6-cyclopropyl-2,3-diphenyl-pyrrolo[2,3-b]pyrazin-5-yl)-heptanoic acid;
7-(6-cyclopropyl-2-(4-methoxy-phenyl)-3-(p-tolyl)-5H-pyrrolo[2,3-b]pyrazin-5-yl)heptanoic acid;
7-(2,3-bis(4-chlorophenyl)-6-cyclopropyl-5H-pyrrolo[2,3-b]pyrazin-5-yl)heptanoic acid;
7-(6-cyclopropyl-2-(4-ethylphenyl)-3-(p-tolyl)-5H-pyrrolo [2,3-b]pyrazin-5-yl)heptanoic acid;
7-(6-cyclopropyl-2,3-di-m-tolyl-5H-pyrrolo[2,3-b]pyrazin-5-yl)heptanoic acid;
7-(6-cyclopropyl-3-(4-ethylphenyl)-2-(p-tolyl)-5H-pyrrolo [2,3-b]pyrazin-5-yl)heptanoic acid;
7-(6-cyclopropyl-3-(4-methoxyphenyl)-2-(p-tolyl)-5H-pyrrolo[2,3-b]pyrazin-5-yl)heptanoic acid;
7-(6-cyclopropyl-3-(m-tolyl)-2-(p-tolyl)-5H-pyrrolo[2,3-b] pyrazin-5-yl)heptanoic acid;
7-(6-cyclopropyl-2-(m-tolyl)-3-(p-tolyl)-5H-pyrrolo[2,3-b] pyrazin-5-yl)heptanoic acid;
7-(6-(2-Hydroxyethyl)-2,3-dip-tolyl-5H-pyrrolo[2,3-b] pyrazin-5-yl)heptanoic acid;
5-(6-Cyclopropyl-2,3-dip-tolyl-5H-pyrrolo[2,3-b]pyrazin-5-yl)pentanoic acid;
6-(6-Cyclopropyl-2,3-dip-tolyl-5H-pyrrolo[2,3-b]pyrazin-5-yl)hexanoic acid;
7-(7-(Methoxymethyl)-2,3-dip-tolyl-5H-pyrrolo[2,3-b] pyrazin-5-yl)heptanoic acid;
7-(6-oxo-2,3-dip-tolyl-6,7-dihydro-5H-pyrrolo[2,3-b] pyrazin-5-yl)heptanoic acid;
7-(2,3-Dip-tolyl-6-(trifluoromethyl)-5H-pyrrolo[2,3-b] pyrazin-5-yl)heptanoic acid; and
7-(6,7-Diethyl-2,3-di-p-tolyl-5H-pyrrolo[2,3-b]pyrazin-5-yl)heptanoic acid;
or a pharmaceutically acceptable salt thereof.

Embodiment 31

The compound according to embodiment 1, the compound is
7-(6-cyclopropyl-2,3-di-p-tolyl-5H-pyrrolo[2,3-b]pyrazin-5-yl)heptanoic acid;
ethyl 7-(6-cyclopropyl-2,3-di-p-tolyl-5H-pyrrolo[2,3-b] pyrazin-5-yl)heptanoate;
7-(6-isopropyl-2,3-di-p-tolyl-pyrrolo[2,3-b]pyrazin-5-yl)-heptanoic acid;
ethyl 7-(6-isopropyl-2,3-di-p-tolyl-5H-pyrrolo[2,3-b] pyrazin-5-yl)heptanoate;
7-(2,3-di-p-tolyl-pyrrolo[2,3-b]pyrazin-5-yl)-heptanoic acid ethyl ester;
7-(2,3-di-p-tolyl-pyrrolo[2,3-b]pyrazin-5-yl)-heptanoic acid;
7-(7-formyl-2,3-di-p-tolyl-5H-pyrrolo[2,3-b]pyrazin-5-yl) heptanoic acid;
7-(7-(hydroxymethyl)-2,3-di-p-tolyl-5H-pyrrolo[2,3-b] pyrazin-5-yl)heptanoic acid;
ethyl 7-(7-(hydroxymethyl)-2,3-di-p-tolyl-5H-pyrrolo[2,3-b]pyrazin-5-yl)heptanoate;
ethyl 7-(7-((isopropylamino)methyl)-2,3-di-p-tolyl-5H-pyrrolo[2,3-b]pyrazin-5-yl)heptanoate;
7-(7-((isopropylamino)methyl)-2,3-di-p-tolyl-5H-pyrrolo[2,3-b]pyrazin-5-yl)heptanoic acid;
7-(6-methoxy-2,3-di-p-tolyl-pyrrolo[2,3-b]pyrazin-5-yl)-heptanoic acid;
ethyl 7-(2,3-di-p-tolyl-6,7-dihydro-5H-pyrrolo[2,3-b] pyrazin-5-yl)heptanoate;

5-(2,3-di-p-tolyl-5H-pyrrolo[2,3-b]pyrazin-6-yl)-pentanoic acid;

2-(5-(2,3-di-p-tolyl-5H-pyrrolo[2,3-b]pyrazin-6-yl)pentanamido)acetic acid;

7-(6-methyl-2,3-di-p-tolyl-5H-pyrrolo[2,3-b]pyrazin-5-yl)heptanoic acid;

7-(6-cyclopropyl-2,3-diphenyl-pyrrolo[2,3-b]pyrazin-5-yl)-heptanoic acid;

7-(6-cyclopropyl-2-(4-methoxy-phenyl)-3-(p-tolyl)-5H-pyrrolo[2,3-b]pyrazin-5-yl)heptanoic acid;

7-(2,3-bis(4-chlorophenyl)-6-cyclopropyl-5H-pyrrolo[2,3-b]pyrazin-5-yl)heptanoic acid;

7-(6-cyclopropyl-2-(4-ethylphenyl)-3-(p-tolyl)-5H-pyrrolo[2,3-b]pyrazin-5-yl)heptanoic acid;

7-(6-cyclopropyl-2,3-di-m-tolyl-5H-pyrrolo[2,3-b]pyrazin-5-yl)heptanoic acid;

7-(6-cyclopropyl-3-(4-ethylphenyl)-2-(p-tolyl)-5H-pyrrolo[2,3-b]pyrazin-5-yl)heptanoic acid;

7-(6-cyclopropyl-3-(4-methoxyphenyl)-2-(p-tolyl)-5H-pyrrolo[2,3-b]pyrazin-5-yl)heptanoic acid;

7-(6-cyclopropyl-3-(m-tolyl)-2-(p-tolyl)-5H-pyrrolo[2,3-1)]pyrazin-5-yl)heptanoic acid;

7-(6-cyclopropyl-2-(m-tolyl)-3-(p-tolyl)-5H-pyrrolo[2,3-1)]pyrazin-5-yl)heptanoic acid;

or a pharmaceutically acceptable salt thereof.

Embodiment 32

The compound according to any one of embodiments 1 to 31, or a pharmaceutically acceptable salt thereof, for use as a medicament.

Embodiment 33

The compound according to any one of embodiments 1 to 31, or a pharmaceutically acceptable salt thereof, for use in the treatment of a disorder or disease mediated by the IP receptor.

Embodiment 34

The compound according to any one of embodiments 1 to 31, or a pharmaceutically acceptable salt thereof, for use in the treatment of a disorder or disease selected from PAH, disorders in need of antiplatelet therapy, atherosclerosis, asthma, COPD, hyperglycemia, inflammatory disease and fibrotic diseases.

Embodiment 35

The compound according to any one of embodiments 1 to 31, or a pharmaceutically acceptable salt thereof, for use in the treatment of a disorder or disease selected from PAH, atherosclerosis, asthma, COPD, hyperglycemia and fibrotic diseases.

Embodiment 36

The compound according to any one of embodiments 1 to 31, or a pharmaceutically acceptable salt thereof, for use in the treatment of a disorder or disease selected from PAH, asthma, COPD and cystic fibrosis.

Embodiment 37

The compound according to any one of embodiments 1 to 31, or a pharmaceutically acceptable salt thereof, for use in the treatment of a disorder or disease selected from PAH or COPD.

Embodiment 38

The compound according to any one of embodiments 1 to 31, or a pharmaceutically acceptable salt thereof, for use in the treatment of PAH.

Embodiment 39

A pharmaceutical composition, comprising:
a therapeutically effective amount of the compound according to any one of claims 1 to 31, or a pharmaceutically acceptable salt thereof, and
one or more pharmaceutically acceptable carriers.

Embodiment 40

A pharmaceutical combination, comprising:
a therapeutically effective amount of the compound according to any one of claims 1 to 31, or a pharmaceutically acceptable salt thereof, and
a second active agent.

Embodiment 41

Use of a compound according to any one of claims 1 to 26, or a pharmaceutically acceptable salt thereof, in the manufacture of a medicament for the treatment of a disorder or disease mediated by the IP receptor.

Embodiment 42

Use of a compound according to any one of claims 1 to 31, or a pharmaceutically acceptable salt thereof, in the manufacture of a medicament for the treatment of a disorder or disease selected from PAH, atherosclerosis, asthma, COPD, hyperglycemia and fibrotic diseases.

Embodiment 43

Use of a compound according to any one of claims 1 to 31, or a pharmaceutically acceptable salt thereof, in the manufacture of a medicament for the treatment of a disorder or disease selected from PAH, asthma, COPD and cystic fibrosis.

Embodiment 44

Use of a compound according to any one of claims 1 to 31, or a pharmaceutically acceptable salt thereof, in the manufacture of a medicament for the treatment of a disorder or disease selected from PAH or COPD.

Embodiment 45

Use of a compound according to any one of claims 1 to 31, or a pharmaceutically acceptable salt thereof, in the manufacture of a medicament for the treatment of PAH.

Embodiment 46

Use of a compound according to any one of claims 1 to 31, or a pharmaceutically acceptable salt thereof, for the treatment of pulmonary arterial hypertension.

Embodiment 47

A method for the prevention or treatment of a condition affected by activation of the IP receptor, comprising: administering an effective amount to activate the IP receptor of at least one compound according to any of claims 1 to 31 to a subject in need of such treatment.

Embodiment 48

A method of treating a disorder or disease selected from PAH, disorders in need of antiplatelet therapy, atherosclerosis, asthma, COPD, hyperglycemia, inflammatory disease and fibrotic diseases in a patient in need thereof, comprising: administering to the subject in need thereof a therapeutically effective amount of the compound according to any one of claims 1 to 31, or a pharmaceutically acceptable salt thereof.

We claim:
1. A compound represented by formula

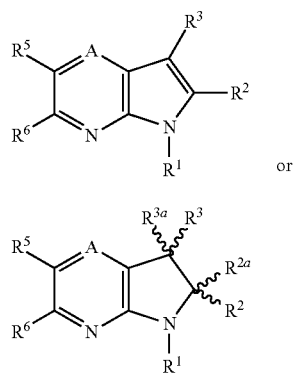

or a pharmaceutically acceptable salt thereof, wherein
A is N;
R' is H or $C_1$-$C_8$ alkyl optionally substituted by one or more halogen atoms;
$R^1$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —($C_2$-$C_4$ alkyl)-$NR^{19}R^{21}$ and $C_3$-$C_7$ cycloalkyl; or
$R^1$ is —X—Y; or
$R^1$ is —W—$R^7$—X—Y; or
$R^1$ is —S(O)$_2$—X—Y; or
$R^1$ is —S(O)$_2$—W—$R^7$—X—Y;
$R^2$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; $C_1$-$C_4$ alkoxy; —($C_0$-$C_4$ alkyl)-$NR^{19}R^{21}$ and $C_3$-$C_7$ cycloalkyl; or
$R^2$ is —X—Y; or
$R^2$ is —W—$R^7$—X—Y; or
$R^2$ is —S(O)$_2$—X—Y; or
$R^2$ is —S(O)$_2$—W—$R^7$—X—Y;
$R^{2a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or
$R^2$ and $R^{2a}$ taken together are oxo;
wherein one of $R^1$ and $R^2$ is —X—Y, —W—$R^7$—X—Y, —S(O)$_2$—X—Y; or —S(O)$_2$—W—$R^7$—X—Y;
$R^3$ is independently selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; —OH; OR'; —($C_0$-$C_4$alkyl)-$NR^{19}R^{21}$; CN; halogen; —($C_0$-$C_4$alkyl)-$C_6$-$C_{14}$aryl; —($C_0$-$C_4$alkyl)-4 to 14 membered heteroaryl; —C(=O)H; —C(=O)OH; —C(=O)$NR^{19}R^{21}$ and $C_3$-$C_7$ cycloalkyl, wherein the aryl and heteroaryl are optionally substituted by one or more substituents independently selected from OH, $C_1$-$C_4$ alkyl, $C_1$-$C_4$ alkoxy, halogens and $C_1$-$C_4$ haloalkyl;
$R^{3a}$ is selected from H; $C_1$-$C_8$ alkyl optionally substituted by one or more halogen atoms, OH, $C_1$-$C_4$ alkoxy, $C_3$-$C_7$ cycloalkyl or $C_3$-$C_7$ cycloalkyloxy; and $C_3$-$C_7$ cycloalkyl; or
$R^3$ and $R^{3a}$ taken together are oxo;
$R^5$ and $R^6$ are independently selected from —($C_0$-$C_4$ alkyl)-$C_6$-$C_{14}$ aryl and —($C_0$-$C_4$ alkyl)-4 to 14 membered heteroaryl, wherein the aryl and heteroaryl are each optionally substituted by one or more Z substituents;
W is $C_1$-$C_8$ alkylene optionally substituted by OH, halogens or $C_1$-$C_4$ alkyl;
X is $C_1$-$C_8$ alkylene optionally substituted by OH, halogens or $C_1$-$C_4$ alkyl;
Y is carboxy, $C_1$-$C_4$-alkoxycarbonyl, tetrazolyl, —C(=O)$NR^{19}R^{21}$ or —CONH—S(O)$_q$—$R^x$, wherein $R^x$ is phenyl, benzyl or —$NR^{19}R^{21}$;
q is 0, 1 or 2;
$R^7$ is a divalent moiety represented by —O—, —S—, —NHC(O)—, —$CH_2$—$CH_2$—, —$C_6$-$C_{14}$ aryl-D-; -3 to 14 membered heterocyclyl-D-, wherein the heterocyclyl contains at least one heteroatom selected from N, O and S, wherein D is O, S, NH or not present;
Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$ alkoxy, $NR^{18}S(O)_2R^{21}$, $S(O)_2NR^{19}R^{21}$; $S(O)_2R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclyl, wherein the heterocyclyl contains at least one heteroatom selected from N, O and S;
$R^{18}$ is independently H or $C_1$-$C_6$ alkyl;
$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; —($C_1$-$C_4$ alkyl)-carboxy; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclyl, the heterocyclyl including one or more heteroatoms selected from N, O and S, optionally substituted by one or more groups selected from halogen, oxo, $C_1$-$C_6$ alkyl and C(O)$C_1$-$C_6$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl; wherein the alkyl groups are optionally substituted by one or more halogen atoms, OH, $C_1$-$C_4$ alkoxy, C(O)NH$_2$, C(O)NH$C_1$-$C_6$ alkyl or C(O)N($C_1$-$C_6$ alkyl)$_2$; or $R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; S(O)$_2$-aryl; S(O)$_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and C(O)O$C_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

2. The compound or a pharmaceutically acceptable salt thereof according to claim 1, wherein $R^2$ is H; or $C_1$-$C_8$ alkyl optionally substituted by one or more halogen atoms, OH or $C_1$-$C_4$ alkoxy;

$R^{2a}$ is H; or $R^2$ and $R^{2a}$ together are oxo; and

R' is H or $C_1$-$C_8$ alkyl.

3. The compound or a pharmaceutically acceptable salt thereof according to claim 2, wherein $R^2$ is H or $C_1$-$C_8$ alkyl optionally substituted by one or more halogen atoms, $C_1$-$C_4$ alkoxy or OH.

4. The compound or a pharmaceutically acceptable salt thereof according to claim 1, wherein $R^5$ and $R^6$ are independently selected from $C_6$-$C_{14}$ aryl and 5 to 6 membered heteroaryl, wherein the heteroaryl contains at least one heteroatom selected from N, O and S, wherein the aryl and heteroaryl are each optionally substituted by one or more Z substituents.

5. The compound or a pharmaceutically acceptable salt thereof according to claim 4, wherein $R^5$ and $R^6$ are independently selected from phenyl optionally substituted by OH, $C_1$-$C_4$ alkyl optionally substituted by one or more OH groups or NH$_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; NR$^{19}$R$^{21}$; C(O)OR$^{19}$; C(O)R$^{19}$; SR$^{19}$; OR$^{19}$; CN; NO$_2$; and halogen.

6. The compound or a pharmaceutically acceptable salt thereof according to claim 1, wherein one of $R^1$ and $R^2$ is —X—Y, —W—$R^7$—X—Y, —S(O)$_2$—X—Y; or —S(O)$_2$—W—$R^7$—X—Y;

W is $C_1$-$C_6$ alkylene optionally substituted by OH, halogens or $C_1$-$C_4$ alkyl;

X is $C_1$-$C_6$ alkylene optionally substituted by OH, halogens or $C_1$-$C_4$ alkyl;

Y is carboxy, $C_1$-$C_4$-alkoxycarbonyl, tetrazolyl, —C(═O)NR$^{19}$R$^{21}$ or —CONH—S(O)$_q$—R$^x$, wherein R$^x$ is phenyl, benzyl or —NR$^{19}$R$^{21}$;

q is 2;

$R^7$ is a divalent moiety represented by —$C_6$-$C_{14}$ aryl-D-; -3 to 14 membered heterocyclyl-D-, wherein the heterocyclyl contains at least one heteroatom selected from N, O and S, wherein D is O; and $R^{19}$ and $R^{21}$ are each independently H or $C_1$-$C_8$ alkyl.

7. The compound or a pharmaceutically acceptable salt thereof according to claim 1, wherein one of $R^1$ and $R^2$ is —(CH$_2$)$_m$—C(O)OR";

m is 3, 4, 5, 6, 7 or 8; and

R" is H or $C_1$-$C_4$ alkyl optionally substituted by one or more halogen atoms.

8. The compound or a pharmaceutically acceptable salt thereof according to claim 1, selected from the group consisting of:

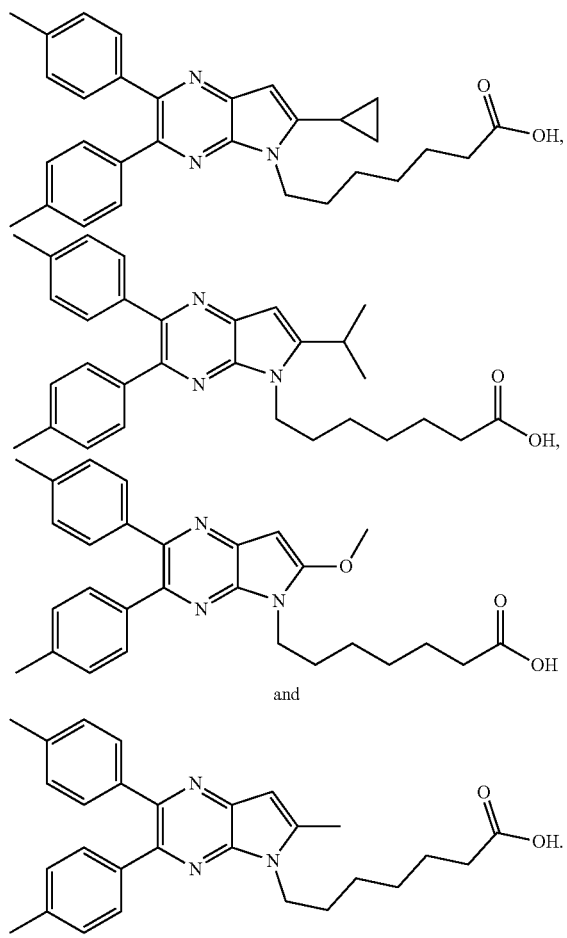

and

9. A pharmaceutical composition, comprising:

a therapeutically effective amount of the compound according to claim 1, or a pharmaceutically acceptable salt thereof, and one or more pharmaceutically acceptable carriers.

* * * * *